United States Patent [19]

Collington et al.

[11] 4,409,213

[45] Oct. 11, 1983

[54] PROSTANOID COMPOUNDS AND PHARMACEUTICAL COMPOSITIONS

[75] Inventors: Eric W. Collington, Welwyn; Harry Finch, Hitchin; Roger F. Newton, Melbourn; Christopher J. Wallis, Royston, all of England

[73] Assignee: Glaxo Group Limited, England

[21] Appl. No.: 440,622

[22] Filed: Nov. 10, 1982

Related U.S. Application Data

[60] Continuation of Ser. No. 232,363, Feb. 6, 1981, abandoned, which is a division of Ser. No. 56,416, Jul. 10, 1979, Pat. No. 4,265,891.

[30] Foreign Application Priority Data

Jul. 11, 1978 [GB] United Kingdom ............... 29403/78

[51] Int. Cl.³ ............... A61K 31/55; A61K 31/557; C07D 223/00; C07D 295/14
[52] U.S. Cl. ............... 424/244; 544/396; 544/399; 424/45; 544/400; 546/187; 424/246; 546/188; 546/190; 424/248.5; 546/208; 546/216; 424/248.53; 546/217; 546/230; 424/248.55; 546/232; 546/233; 424/250; 546/234; 546/235; 424/267; 546/238; 546/239; 424/274; 542/426; 560/10; 424/304; 560/16; 560/36; 424/309; 560/43; 560/121; 424/305; 562/426; 562/441; 424/319; 562/444; 562/448; 544/58.1; 562/452; 562/455; 544/58.2; 562/456; 562/457; 544/58.5; 562/433; 562/503; 544/58.6; 260/243.3; 260/244.4; 544/58.7; 260/245.7; 260/239 BF; 544/82; 260/330.6; 260/465 D; 544/85; 548/523; 548/566; 544/86; 548/567; 548/573; 544/87; 544/121; 544/130; 544/141; 544/160; 544/163; 544/165; 544/169; 544/171; 544/357; 544/360; 544/372

[58] Field of Search ............... 544/58.2, 58.5, 58.6, 544/58.1, 58.7, 121, 130, 141, 160, 163, 165, 169, 171, 360, 357, 372, 82, 85, 86, 87, 396, 399, 400; 546/187, 188, 190, 208, 217, 216, 230, 232, 233, 234, 235, 238, 239; 542/426; 548/523, 566, 567, 573; 260/243.3, 244.4, 245.7, 330.6, 239 BF, 465 D; 560/10, 16, 36, 43, 121; 562/426, 441, 444, 448, 452, 455, 456, 457, 433, 503; 424/45, 244, 246, 248.5, 248.53, 248.55, 250, 267, 274, 304, 309, 305, 319

[56] References Cited

U.S. PATENT DOCUMENTS

| | | | |
|---|---|---|---|
| 4,182,903 | 1/1980 | Favara et al. | 562/503 |
| 4,189,606 | 2/1980 | Favara et al. | 562/455 |
| 4,239,778 | 12/1980 | Venton et al. | 424/305 |

OTHER PUBLICATIONS

LeBreton et al, *Proc. Natl. Acad. Sci.*, USA, vol. 76 (1979) pp. 4097-4101.

*Primary Examiner*—Robert W. Ramsuer
*Attorney, Agent, or Firm*—Bernard, Rothwell & Brown

[57] ABSTRACT

Prostanoid compounds are described having the formula:

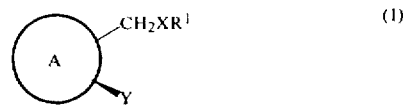

where A is a cyclopentane ring, which is substituted by oxo and/or hydroxy or etherified hydroxy and may be saturated or unsaturated; X is —CH=CH— or —(CH$_2$)$_2$—; R is alkyl having a terminal —COOH or ester group; and Y is amino or substituted amino, particularly heterocyclic amino.

The compounds have bronchodilator activity and/or inhibit blood platelet aggregation.

The preparation and pharmaceutical formulation of the compounds is also described.

7 Claims, No Drawings

PROSTANOID COMPOUNDS AND PHARMACEUTICAL COMPOSITIONS

This application is a continuation of U.S. patent application Ser. No. 232,363, filed on Feb. 6, 1981, now abandoned, which was a division of U.S. patent application Ser. No. 56,416, filed July 10, 1979 now U.S. Pat. No. 4,265,891.

This invention relates to prostanoid compounds.

Prostaglandins are a class of naturally occurring cyclopentane derivatives which are biologically active in many physiological systems and they and substances which antagonise their effects are therefore of considerable interest in both human and veterinary medicine.

Prostaglandins can generally be regarded as formal derivatives of prostanoic acid, which has the structure:

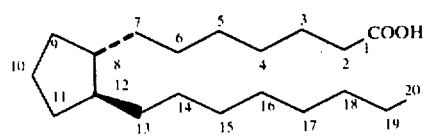

The side chain at the 8-position is sometimes referred to as the α-side chain, and the side chain at the 12-position as the β-side chain.

In the natural prostaglandins, the cyclopentane ring carries oxo and/or hydroxy substituents and it may also have a double bond, for example at the 10,11-position. According to the substitution pattern in the ring the prostaglandins are defined as being of the A, E, F etc. series (see for example "Prostaglandin Synthesis", J. S. Bindra and R. Bindra, Academic Press Inc. [New York], 1977). The two side chains may also be unsaturated, for example at the 5,6- or 13,14-positions, and the β-side chain frequently carries a hydroxy group at the 15-position.

The characteristic properties of natural prostaglandins include for example lowering or increasing blood pressure, stimulation or relaxation of smooth muscle, increase of blood flow, inhibition of lipolysis, inhibition of gastric secretion, inhibition of blood platelet aggregation and thrombus formation, stimulation of epidermal proliferation and keratinisation, induction of luteolysis in certain femal mammals, and induction of parturition in mammals. Prostaglandins have been suggested for use in a variety of ways on account of these properties.

In view of the activity found in the natural prostaglandins, considerable effort has been directed towards the preparation of synthetic analogues. Many such compounds have been described, and in general it has been reported that these compounds possess activity within the same spectrum as the natural compounds. The synthetic compounds can however have increased selectivity of action, longer duration of activity or different potency, and in some cases they can antagonise the activity of natural prostaglandins.

In most of the synthetic prostanoids previously reported, the side chains have been attached to the cyclopentane ring via carbon atoms, as in the natural prostaglandin structure. We have now found a new class of prostanoid compounds in which the α-side chain has the same or similar structure to that of the natural compounds, while the β-side-chain is attached to the ring via a nitrogen atom. The β-side chain in our compounds can be regarded as the residue of ammonia or a primary or secondary amine. Compounds in this class have shown prostanoid activity in our tests and in particular they inhibit blood platelet aggregation and have bronchodilatory action.

The invention provides prostanoids of the general formula (1)

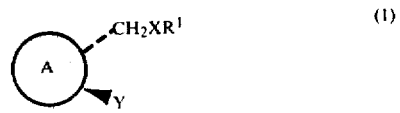

in which
A represents

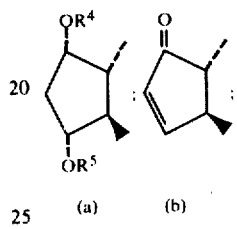

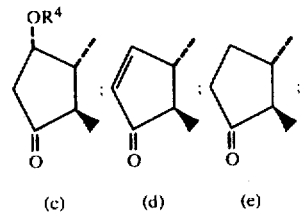

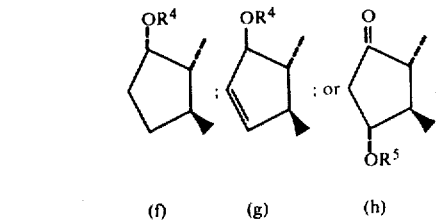

X is cis or trans —CH=CH— or —(CH$_2$)—;

R$^1$ is straight or branched C$_{1-7}$ alkyl bearing as a terminal substituent —COOR$^{10}$ where R$^{10}$ is a hydrogen atom, C$_{1-6}$alkyl or C$_{7-10}$aralkyl;

Y represents (i)-NR$^2$R$^3$ where R$^2$ and R$^3$ are the same or different and are each a hydrogen atom, aralkyl having a C$_{1-7}$alkyl portion or C$_{1-10}$alkyl, both alkyls being optionally substituted by one or more substituents —OR$^7$ (where R$^7$ is a hydrogen atom, C$_{1-7}$alkyl, aryl or aralkyl having a C$_{1-4}$alkyl portion) or —NR$^8$R$^9$ (where R$^8$ and R$^9$ are the same or different and are each a hydrogen atom or C$_{1-4}$alkyl, or where —NR$^8$R$^9$ is a saturated hterocyclic amine group as defined below for Y); any aryl group in R$^2$ or R$^3$ being optionally substituted by one or more C$_{1-4}$alkyl or trifluoromethyl groups; always provided that the total numbers of carbon atoms in the group —NR$^2$R$^3$ does not exceed 15;

or (ii) a saturated heterocyclic amino group which has 5-8 ring members and (a) optionally contains in the ring —O—, —S—, —SO$_2$—, —NR$^{14}$— (where R$^{14}$ is a hydrogen atom, C$_{1-7}$alkyl or aralkyl having a C$_{1-4}$alkyl portion), >C(OH)R$^6$ (where R$^6$ is a hydrogen atom, C$_{1-7}$alkyl, phenyl, or aralkyl having a C$_{1-4}$alkyl portion); and/or (b) is optionally substituted by one or more $C_{1-4}$alkyl groups;

$R^4$ is a hydrogen atom, $C_{1-6}$alkyl (optionally interrupted by one or two oxygen atoms), $C_{3-6}$alkenyl, $C_{2-4}$alkanoyl, aralkanoyl having a $C_{2-4}$alkanoyl portion, aryl or aralkyl having a $C_{1-3}$alkyl portion (the aryl portion being optionally substituted by one or more halogen, hydroxy, $C_{1-6}$alkyl, $C_{1-6}$alkoxy, $C_{1-4}$hydroxyalkoxy, trifluoromethyl, cyano, phenyl, aryloxy, $C_{5-7}$cycloalkyl, aralkoxy, dimethylaminomethyl, carboxamido (—$CONH_2$), thiocarboxamido (—$CSNH_2$), $C_{1-4}$alkanoyl or —$NR^8R^9$ groups as defined above);

$R^5$ is as defined above for $R^4$, excluding aryl and with the proviso that $R^5$ is not hydrogen when A is the group (h);

and the physiologically acceptable salts thereof; provided that when A is the group (a) in which both $R^4$ and $R^5$ are hydrogen atoms and Y is the group —$Nr^2R^3$ in which $R^2$ is a hydrogen atom or $C_{1-4}$alkyl, $R^3$ is not an alkyl group which is only substituted by a hydroxy group.

In the structural formulae herein, a broken line connected to a ring substituent means that, with the ring substantially in the plane of the page, the substituent lies below the plane of the ring; a wedge ⊸ connected to a ring substituent means that the substituent to which is is attached lies above the plane of the ring. A wavy line ⌇ connected to a ring substituent means that the substituent to which it is attached lies above and/or below the plane of the ring. Such formulae are to be understood to depict either or both optical isomers of each of the compounds concerned as well as mixtures of the isomers, including racemates, even though the precise structure as set out only relates to one optical isomer.

Generally, the cylopentane ring preferably has the substitution/unsaturation pattern (a), (c) or (g) shown above. Compounds having the ring type (c) are particularly important.

In the group —$CH_2XR^1$, the $R^1$ alkyl group preferably contains 3 carbon atoms in a straight chain. Examples of suitable $R^{10}$ groups are $C_{1-3}$alkyl and benzyl. $R_{10}$ is preferably a hydrogen atom or methyl. $R^1$ is preferably —$(CH_2)_3COOCH_3$ or —$(CH_2)_3COOH$.

When $R^1$ is terminally substituted by —COOH, the compounds are capable of salt formation with bases, examples of suitable salts being alkali metal (e.g. sodium and potassium), ammonium and substituted ammonium (e.g. tromethamine or dimethylaminoethanol) salts.

X is preferably a —$CH_2CH_2$— group or a cis —CH=CH— group.

When one of $R^2$ and $R^3$ is alkyl or substitued alkyl, the alkyl group preferably contains no more than 7 (e.g. 2-7) carbon atoms and preferably has a straight chain. Examples of such groups are n-hexyl and n-heptyl. In such compounds, the other group of $R^2$ or $R^3$ is preferably hydrogen or methyl. When $R^2$ or $R^3$ is an aralkyl group, it may for example be benzyl, phenethyl or phenpentyl.

In the optional substituent —$OR^7$ in $R^2$ or $R^3$, examples of $R^7$ are a hydrogen atom, methyl, n-butyl, phenyl, benzyl and phenethyl. The optional amino substituent —$NR^8R^9$ may for example be —$NH_2$, —NHMe, —NHEt, —$NMe_2$ or —$NEt_2$. These optional substituents may for example be carried at the β-position, as in β-hydroxyalkyl groups. Two —$OR^7$ groups may be present, particularly on an $R^2$ or $R^3$ alkyl group; for example, there may be a hydroxy group at the β-position and a second —$OR^7$ group at the terminal position.

Aryl (e.g. phenyl) groups in $R^2$ and $R^3$ may themselves be subsituted, e.g. by $C_{1-4}$alkyl or trifluoromethyl.

Compounds in which Y is a saturated heterocyclic amino grop are however preferred. The group may for example have a 5, 6 or 7-membered ring, e.g. pyrrolidino, piperidino, morpholino, piperazino, thiamorpholino, 1-dioxothiamorpholino, homomorpholino and hexamethyleneimino.

Examples of the optional subsituents which may be present on a second nitrogen atom in the ring are methyl, ethyl and benzyl. The carbon atoms of the heterocyclic rings may for example be substituted by methyl or ethyl. The group >C(OH)$R^6$ may for example be present in a piperidino ring and when $R^6$ is other than hydrogen it may for example be methyl, ethyl, or butyl.

Compounds in which Y is morpholino group are preferred, the group being either unsubstituted or substituted, e.g. by methyl at the 2- and/or 6-position.

The amino group in the β-side chain enables the compounds to form salts with inorganic or organic acids, e.g. hydrochlorides, sulphates, acetates, maleates and succinates.

$R^4$ may for example be a hydrogen atom, $C_{1-6}$alkyl (e.g. methyl, iso-propyl or pentyl), $C_{3-6}$alkenyl (e.g. allyl), alkyl having up to 6 carbon atoms interrupted by one or two oxygen atoms (e.g. methoxymethyl or methoxyethoxymethyl), $C_{2-4}$alkanoyl (e.g. acetyl), aryl (e.g. phenyl) or, preferably, aralkyl having a $C_{1-3}$ alkyl portion. The alkyl portion may carry one or more aryl groups and the aryl group may be mono- or bicyclic (e.g. phenyl). Examples of aralkyl groups are benzyl, phenethyl, α-methylbenzyl and benzhydryl. The aryl portions of the aralkyl groups may be substituted, preferably by halo, $C_{1-6}$alkyl, $C_{1-6}$alkoxy, trifluoromethyl, cyano, phenyl, $C_{5-7}$cycloalkyl, amino, dialkylamino, —$CONH_2$, —$CSNH_2$, dimethylaminomethyl or formyl. Specific examples of these optional substituents are chloro, bromo, methyl, methoxy, butyloxy cyclohexyl, amino, diaklylamino, and formyl. Substituted benzyl groups are particularly preferred, the substituent being for example in the para-position.

A particularly important group of compounds is those in which A is the group (c), X is cis —CH=CH— or —$CH_2CH_2$—, $R^1$ is —$(CH_2)_3COOCH_3$ or —$(CH_2)_3COOH$, Y is a heterocyclic amino group (particularly morpholino) and $R^4$ is alkyl, alkyl interrupted by one or two oxygen atoms, or substituted or unsubstituted aralkyl.

Compounds which are particularly preferred on account of the selective activity they have shown in our tests are those in which A is the group (c), X is cis —CH=CH—, $R^1$ is —$(CH_2)_3COOCH_3$, Y is morpholino and $R^4$ is 4-phenyl-benzyl, 4-dimethylaminobenzyl, 4-cyclohexylbenzyl, 4-aminobenzyl or 4-t-butylbenzyl; and those in which A is the group (c), X is cis —CH=CH—, $R^1$ is —$(CH_2)_3COOH$, Y is morpholino and $R^4$ is 4-phenylbenzyl or 4-cyclohexylbenzyl; and those in which A is the group (c), X is —$(CH_2)_2$—, Y is morpholino, $R^4$ is 4-phenylbenzyl and $R^1$ is —$(CH_2)_3COOCH_3$ or —$(CH_2)_3COOH$. These are the products of Examples 143, 144, 147, 175, 176, 177, 179, 199 and 208 below.

As indicated above, tests have shown that compounds of formula (1) inhibit blood platelet aggregation and/or have bronchodilatory activity. The test for potential bronchodilation is as described by K. M. Lulich, et al in British Journal of Pharmacology 58, 71–79, (1976) except guinea-pig lung is used instead of cat lung.

The test for inhibition of platelet aggregation is as described by G. V. Born in Nature 194, 927-929 (1962) except collagen is used instead of ADP as the proaggregatory agent.

The compounds are thus of interest in the treatment of asthma and as antithrombotic agents for use in the treatment and prevention of cardiovascular diseases or conditions such as arteriosclerosis, atherosclerosis and myocardial infarcts. They may be formulated for use in a conventional manner, with one or more pharmaceutical carriers. The comopunds may also be used as additives for preventing aggregation of whole blood, e.g. for storage purposes.

For oral administration, the pharmaceutical composition may take the form of, for example, tablets, capsules, powders, solutions, syrups, or suspensions prepared by conventional means with acceptable excipients.

The compounds may be formulated for parenteral administration by bolus injections or continuous infusion. Formulations for injections may be presented in unit dosage form in ampoules, or in multi-dose containers, with an added preservative. The compositions may take such forms as suspensions, solutions, or emulsions in oily or aqueous vehicles, and may contain formulatory agents such as suspending, stabilising and/or dispersing agents. Alternatively, the active ingredient may be in powder form for reconstitution before use with a suitable vehicle, e.g. sterile pyrogen-free water.

For administration by inhalation the compounds are conveniently delivered in the form of an aerosol spray presentation from pressurised packs or a nebuliser, or as a cartridge from which the powdered composition may be inhaled with the aid of a suitable device. In the case of a pressurised aerosol the dosage unit may be determined by providing a valve to deliver a metered amount.

For use in antithrombotic agents, the compounds are preferably administered orally, for example in amounts of 0.1 to 10 mg/kg body weight, 1 to 4 times daily. For use in the treatment of asthma, the compounds may also be administered orally in amounts of 0.1 to 10 mg/kg body weight, 1 to 4 times daily; preferably however they are administered by inhalation in the form of aerosols or solutions for nebulisers, at doses varying from 0.3 to 30 mg, 1 to 4 times daily. The compounds may be used in combination with other antiasthmatic agents. It will be appreciated that the precise dose administered will always depend on the aqueous and condition of the patient.

The compounds of formula (1) may be prepared by selection and adaptation of methods known in prostanoid chemistry (see for example "Prostaglandin Synthesis", J. S. Bindra and R. Bindra, Academic Press Inc. [New York], 1977) or by analogous methods. Methods (a) to (d) below are particularly important in forming certain prostanoids of the desired class, and these primary products (formulae 2, 8, 12 and 17, below) can then be converted into other members of the class by conventional techniques.

(a) Thus for example one method of preparing compounds of formula (2)

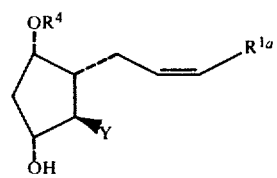

(where $R^{1a}$ is as defined above for $R^1$ where $R^1$ bears a terminal —COOH group, Y and $R^4$ are as defined above) is by reacting lactols of formula (3) or their aldehyde isomers

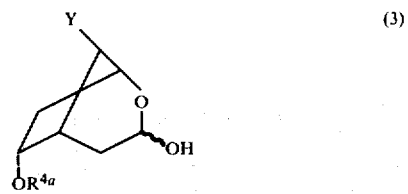

(where Y is as defined above and —$OR^{4a}$ is as defined above for —$OR^4$ or is a protected hydroxy group) with appropriate Wittig reagents, e.g. a phosphorane of formula $R_3^{11}P\!=\!CHR^{1a}$ or a salt thereof (where $R^{1a}$ is as defined above and $R^{11}$ is $C_{1-6}$ alkyl or aryl, e.g. monocyclic aryl such as phenyl), followed, where $R^4$ is hydrogen, by removal of the protecting group —$R^{4a}$. Suitable reaction solvents include hydrocarbons (e.g. benzene and toluene), ethers (e.g. tetrahydrofuran), dialkylsulphoxides (e.g. dimethylsulphoxide), alcohols and halogenated hydrocarbons. The reaction may be carried out at any suitable temperature up to 50° C., preferably at room temperature.

The reaction is particularly suitable for the preparation of compounds in which $R^1$ is terminally substituted by —COOH (in salt form). If compounds in which $OR^4$ represents a hydroxy group are required, the hydroxy group should preferably be in a protected state prior to the reaction. Any hydroxy group in Y should preferably also be in a protected state prior to this reaction. Suitable hydroxy protecting groups are described below. Any —$NH_2$ group present should also be protected, e.g. by t-butoxycarbonyl.

This reaction, as will be appreciated, is the last step in a multi-stage sequence related to that described in Belgain Patent Specification No. 848992 for the introduction of carbon-attached β-side chains, and the intermediates required may be prepared by the methods described therein, modified as necessary for the introduction of the nitrogen-linked β-side chain.

The intermediates of formula (3) may thus be prepared by the following sequence (where $Y^a$ is as defined for Y above, other than —$NH_2$):

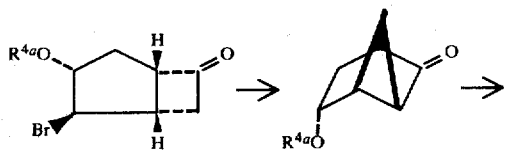

-continued

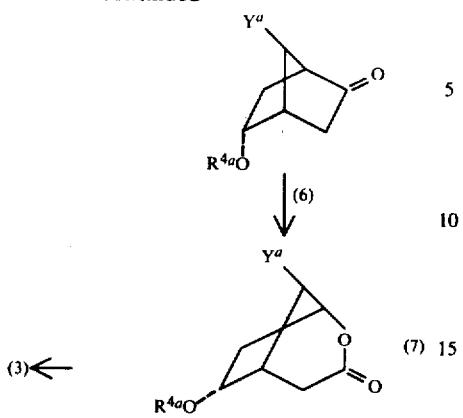

It should be noted that the tricyclic intermediates of formula (5) are not usually isolated; the norbornanones of formula (6) can be obtained directly by treatig compounds of formula (4) with amines Y$^a$H in the presence of a non-nucleophilic base (e.g. potassium t-butoxide, sodium hydride or sodium metal). It should also be noted that the significant difference in the method as compared with that of Belgian Specification No. 848992 lies in the use of the amines Y$^a$H to introduce the Y$^a$ groups; these replace the organometallic reagents used in the method of the Belgian Specification to introduce β-side chains attached via a carbon atom. In some circumstances (when Y$^a$H is sufficiently basic) no extra base needs to be added in the first stage, but in other respects the sequence leading to the lactols of formula (3) can be performed as described in the Belgian Specification. Thus, the Baeyer-Villiger oxidation of the norbornanones of formula (6) to lactones of formula (7) may for example be effected with peracetic acid at a low temperature, using aqueous acetic acid or $CH_2Cl_2$ as solvent: and lactones of formula (7) can be reduced to give the mixed epimers of lactols of formula (3) with di-isobutyl aluminium hydride in a hydrocarbon solvent, at a low temperature e.g. about $-70°$ C.

When it is desired to isolate an intermediate of formula (5), it can be formed (as described in the Belgian Specification) by treatig a ketone of formula (4) with a non-nucleophilic base. A compound of formula (6) can then be prepared in a separate step, by treatment of a compound of formula (5) with an amine Y$^a$H in the presence or absence of the base. In circumstances where Y$^a$ contains an optional hydroxy substituent, this should preferably be protected in the preparation of compounds of formula (6).

Compounds of formula (4), particularly whre R$^4$ is aralkyl, may also be prepared by treating the compound of formula (4) in which R$^4$ is hydrogen with a compound R$^4$OH in the presence of an acid catalyst.

Compounds of formula (2) in which Y is —NH$_2$ may be prepared as follows. A compound of formula (4) is first treated with a phthalimide to give a compound of formula (6) in which Y$^a$ is phthalimido. After the Baeyer-Villiger oxidation, treatment with hydrazine gives a compound of formula (7) in which Y$^a$ is —NH$_2$. The amino group is then protected (e.g. as (t-but-)OCONH—) and the compound then reduced to give a lactol (3) and its aldehyde isomer. Protection of the free hydroxy group of the latter (e.g. as the tetrahydropyranyl ether) allows the Wittig reaction to be performed. The hydroxy and amino protecting groups are then removed by acid hydrolysis e.g. with trifluoroacetic acid. This reaction sequence is particularly suitable for compounds in which R$^4$ is aralkyl.

(b) An alternative method of forming the general prostanoid structure of compounds of formula (1) has as its last step the preparation of compounds of formula (8)

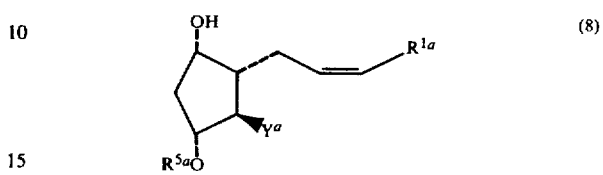

(where R$^{1a}$, R$^5$ and Y$^a$ are as defined above) by reaction of compounds of formula (9)

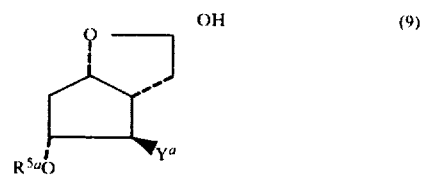

(where Y$^a$ is as defined above and —OR$^{5a}$ is as defined above for —OR$^5$ or is a protected hydroxy group) with appropriate Wittig reagents, in the same manner as described above for the preparation of the compounds of formula (2) followed where R$^5$ is hydrogen by removal of the protecting group —R$^{5a}$. Any hydroxy group in R$^{1a}$ or Y$^a$ should preferably be in a protected state prior to the Wittig reaction. Again, suitable protecting groups are as described below.

The intermediates of formula (9) may be prepared from compounds of formula (7) as shown in the following sequence:

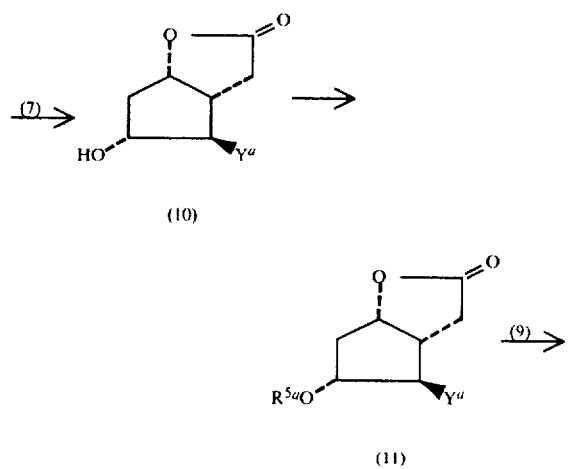

In the compounds of formula (7) used in this reaction sequence, the group R$^{4a}$ should be capable of ready and selective removal, and thus generally R$^{4a}$ O is a protected hydroxy group, e.g. a tetrahydropyranyloxy group or a carboxylic acyloxy, tri(hydrocarbyl) silyloxy or arylmethoxy group such as described below generally with reference to protected hydroxy groups. R$^{4a}$ is preferably a tetrahydropyranyl, acetyl or benzyl group. The formation of the compounds of formula (10) can occur spontaneously on removal of the group $R^{4a}$, e.g. by the methods described below.

The rearrangement of the deprotected compound of formula (7) does not, however, always occur spontaneously, and in these cases the step of removing the $R^{4a}$ group may be followed by treatment with base (e.g. dilute sodium hydroxide) and then acd (e.g. dilute hydrochloric acid).

The hydroxy group of lactones of formula (10) may then be protected (e.g. as the tetrahydropyran-2-yl ether) to give lactones of formula (11) which are then reduced to give lactols of formula (9), e.g. with diisobutyl aluminium hydride in the same manner as described above for the reduction of formula (7).

(c) Compounds of formula (12)

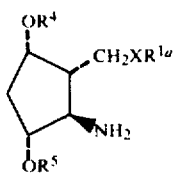

(12)

(where $R^{1a}$, $R^4$, $R^5$ and X are as defined above) may alternatively be prepared by reducing compounds of formula (13)

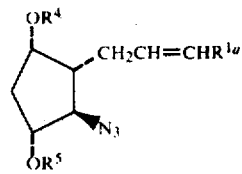

(13)

Compounds of formula (12) in which X is —$(CH_2)_2$— may be prepared by catalytic hydrogenation of the starting materials of formula (13) using for example platinum or palladium on carbon as the catalyst. However, when compounds of formula (12) in which X is —CH=CH— are required, selective reduction methods specific for the azide function should be used with compounds of formula (13). Examples of suitable reagents are zinc and sodium dihydrogen phosphate in a suitable solvent (e.g. tetrahydrofuran); zinc and methanol/sulphuric acid; or triphenylphosphine followed by methanol/sulphuric acid.

The starting materials of formula (13) may be prepared in the same manner as generally described above for the preparation of compounds of formulae (2) and (8), except that azide ion is used in the preparation of compounds of formula (6) instead of reagents $Y^aH$. The norbornanone intermediates in this sequence thus have the formula (14)

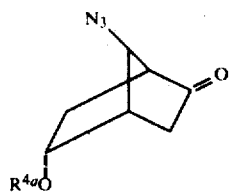

(14)

and may be prepared by reacting ketones of formula (5) with azides (e.g. an alkali metal azide such as $NaN_3$), for example in a two phase reaction medium (e.g. water and a halogenated hydrocarbon, e.g. $CH_2Cl_2$) in the presence of a base e.g. sodium hydroxide. A phase transfer catalyst (e.g. benzyl triethylammonium chloride) is advantageously used. The compounds of formula (14) may then be converted into intermediates of formulae (15) or (16)

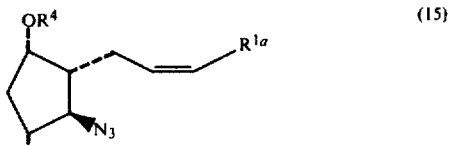

(15)

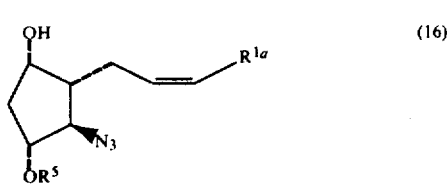

(16)

by the methods described above for reactions (1) and (2).

The compounds of formulae (15) and (16) may be reduced directly to compounds of formula (12).

The hydroxy groups, the group $R^{1a}$ or the configuration of X may be modified, or a double bond introduced into the ring, after the formation of the amino group. The amino group may need to be protected in such transformations. The hydroxy groups may also be modified before the reduction of compounds of formula (13).

(d) Compounds of formula (17)

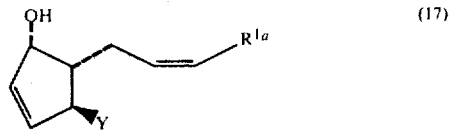

(17)

(where $R^{1a}$ and Y are as defined above) can also be prepared by treatment of compounds of formula (18)

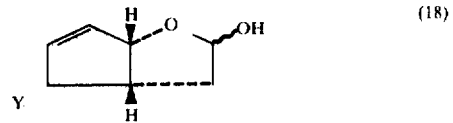

(18)

with appropriate Wittig reagents, in the same manner as described above for the preparation of compounds of formulae (2) and (8). In this instance, the starting materials of formula (18) may be prepared by first treating a compound of formula (19)

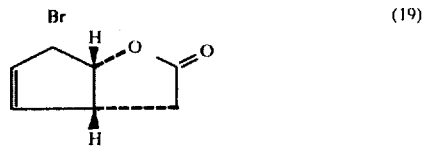

(19)

with amines of formula YH (e.g. at room temperature in a suitable solvent, e.g. acetonitrile) to form compounds of formula (20)

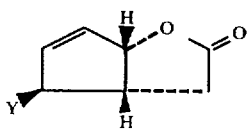

(20)

and then reducing the latter, for example as described above for the reduction of the lactones of formula (7).

Some methods, which are generally conventional in prostanoid chemistry (see for example "Prostaglandin Synthesis" J. S. Bindra and R. Bindra, as above) will now be described briefly for the modification of prostanoids produced by methods (a)-(d) above or by other methods. It will be appreciated that the following reactions will frequently require the use of (or will conventionally be applied to) starting materials having protected functional groups (e.g. hydroxy). The protection and deprotection of the groups is discussed separately below, but it is to be understood that in the following methods references to the use of starting materials of corresponding structure to the desired product are intended to include starting materials having protected functional groups. It will also be appreciated that certain of the reactions described below are capable of affecting other groups in the starting material which are desired in the end product; care must therefore be taken, in accordance with conventional practice, to perform multi-stage reactions in a sequence which does not modify groups which are to be retained in the end products.

(e) Compounds in which $R^1$ is terminally substituted by an esterified carboxyl group can be prepared by esterification of the corresponding carboxylic acid. Conventional esterification techniques may be used, reaction with a diazoalkane being preferred. The alkyl esters may also be formed by reaction with an appropriate alcohol in the presence of a mineral acid, e.g. hydrochloric or sulphuric acid. Esterification (e.g. with methanol) is often useful in isolating compounds in which $R^1$ bears a terminal —COOH group, subsequent de-esterification liberating the acid if desired. Also, one ester may be converted into another, for example by treatment with the appropriate alcohol.

(f) Compounds in which $R^1$ is terminally substituted by a —COOH group can be prepared by saponifying a corresponding ester, e.g. using KOH or Na OH in methanol.

(g) Compounds in which X is trans —CH═CH— may be prepared by isomerising the corresponding cis compound. The isomerisation may for example be effected by treatment with azobisisobutyronitrile and thiophenol, using for example a hydrocarbon solvent and any suitable temperature up to reflux. Where an oxo group is desired in the end product, it should be introduced after this reaction.

(h) Compounds in which X is —(CH$_2$)$_2$— may be prepared by catalytic hydrogenation of a corresponding compound in which X is —CH═CH—. Conventional catalysts may be used, preferably palladium or platinum on carbon, in a suitable solvent (e.g. an alcohol such as methanol) e.g. at room temperature.

(i) Compounds in which $R^4$ or $R^5$ is alkyl, alkenyl or aralkyl may be prepared by etherification of a corresponding hydroxy compound, for example by reaction with an appropriate halide, for example by reaction at room temperature in the presence of a suitable base (e.g. sodium hydride) in a suitable solvent (e.g. dimethylformamide).

(j) Compounds in which $R^4$ or $R^5$ is alkanoyl or aralkanoyl can be prepared by esterification of a corresponding hydroxy compound, for example with the appropriate acid or anhydride or halide thereof.

(k) Compounds in which $R^4$ or $R^5$ is a hydrogen atom can be prepared from the corresponding compounds in which the $R^{4a}O$— or $R^{5a}O$— group is a protected hydroxyl group, for example by reduction or acid or alkaline hydrolysis. The formation of hydroxy compounds in this way is discussed more fully below in connection with hydroxy group protection.

(l) Compounds having a 9- or 11-oxo group may be prepared by oxidizing the corresponding hydroxy compound, for example with a $Cr^{III}$ oxidising reagent, e.g. Jones reagent. Other conventional methods can also be used, for example using dimethylsulphoxide and a suitable electrophilic reagent, such as acetyl bromide, oxalyl chloride, thionyl chloride, or dicyclohexylcarbodiimide. With the latter reagent, the reaction is preferably carried out in the presence of trifluoroacetic acid or its pyridinium salt.

Any free hydroxy group present should be protected in this reaction.

(m) Compounds in which A is the group (d) or (b) may be prepared by elimination of $R^{4a}OH$ or $R^{5a}OH$ from a corresponding compound possessing the cyclopentanoid substitution pattern (c) or (h). The elimination may be effected in the presence of an acid (e.g. an organic acid such as acetic acid) at temperatures of 20°-60° C., or by means of an acid anhydride in pyridine, e.g. at room temperature.

(n) Compounds in which A is the group (e) or (f) may be prepared by catalytic hydrogenation of a corresponding compound in which A is the group (d) or (g). Conventional catalysts may be used, particularly platinum or palladium on carbon.

(o) Compounds in which Y is a mono- or disubstituted amino group may be prepared by modifying a corresponding primary or secondary amino compound, with protection of hydroxyl groups where appropriate.

These reactions may be performed by reacting compounds of formula (1) in which for example Y represents $NHR^3$ where $R^3$ is as defined above with compounds of formula $R^2X$ where $R^2$ is as defined above other than hydrogen and where X is readily displaceable group such as halide (e.g. iodide) or a hydrocarbylsulphonyloxy group, e.g. a toluene-p-sulphonyloxy group. The reactions may be carried out in solvents (such as acetonitrile) in the presence of potassium carbonate.

When a primary amine is used as starting material [Y is —NH$_2$ in formula (1)] the reaction can produce either N-mono or N, N-di-substituted products, and when a secondary amine of formula (1) is used as starting material the reaction can produce tertiary amines of the invention in which $R^2$ and $R^3$ are either the same or different. Compounds in which Y is a cyclic amino group may similarly be prepared by reaction of a compound in which Y is —NH$_2$ with a compound $XR^{15}X$, where $R^{15}$ is the appropriate divalent group.

Alternatively, this process may be performed by reacting primary amino or secondary amino compounds of formula (1) appropriate mono- or di-carbonyl compounds in the presence of a reducing agent in reductive amination procedures. For example with starting materials in which Y is —NH$_2$, the use of aldehydes or ketones may give the corresponding N-mono or N,N-disubstituted compound (depending partly on the proportion of aldehyde or ketone used), whereas a dialdehyde or diketone may give compounds in which Y is a cyclic amino group (e.g. glutardialdehyde may be used to form a piperidino group). When secondary amines are used as starting materials, mono-carbonyl compounds only will be used. The reducing agents which may be used are those generally known for the reduction of imines, e.g. formic acid, or an alkali metal borohydride or cyanoborohydride (e.g. sodium borohydride or potassium cyanoborohydride, using an alcohol such as ethanol as solvent, suitably at room temperature, preferably at pH4-6), or hydrogen in the presence of a metal catalyst, e.g. palladium.

Compounds in which $R^2$ or $R^3$ possesses a $\beta$-hydroxy substituent are conveniently prepared by reacting appropriate compounds of formula (1) in which Y is a mono- substituted amino group (particularly —NHCH$_3$) or a primary amino group with an appropriate 1,2-epoxide.

Suitable primary amino starting materials may be prepared by reaction (c) above. Secondary amino starting materials may be prepared by reactions (a) and (b) above, but in some instances they are more conveniently prepared by dealkylation or de-aralkylation of a compound of formula (1) in which Y is —NH$^{12}$R$^{13}$, where R$^{12}$ and R$^{13}$ are alkyl or aralkyl and may be the same or different. The dealkylation or dearalkylation may be effected by treating the disubstituted amine with 2,2,2-trichloroethyl chloroformate to form a carbamate in which Y is

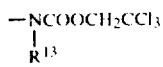

which on treatment with zinc dust gives the required starting material in which Y is —NHR$^{13}$.

(p) Compounds in which R$^4$ is aralkyl substituted by amino may be prepared by reduction of the corresponding azide, in the same manner as generally described above for process (c).

(q) Compounds in which R$^4$ is aralkyl substituted by —CH$_2$N(CH$_3$)$_2$ may be prepared by treatment of the corresponding formyl compound with dimethylamine in the presence of a reducing agent, as generally described above for process (o).

(r) Compounds in which R$^4$ is aralkyl substituted by —CONH$_2$ or —CSNH$_2$ may be prepared from the corresponding cyano compound by hydrolysis or hydrosulphidation, e.g. with sulphur in the presence of a reducing agent.

Where salts of compounds of formula (1) are desired such salts may be formed by conventional methods, for example by treating acids of formula (1) with appropriate bases such as dilute alkali-metal hydroxides. Where the compound contains a basic amino group, salts may also be formed with acids.

As indicated above, hydroxy groups will necessary or conveniently be protected in the reactions described above. The last step in the preparative sequence is thus frequency the liberation of a free hydroxy group from the protected form. Suitable methods of protection and deprotection are described below.

A protected hydroxyl group (OR$^h$) may, for example, be a carboxylic acyloxy, tetrahydropyranyloxy, tri(hydrocarbyl)silyloxy or arylmethoxy group. Where OR$^h$ is acyloxy it may be alkanoyloxy, preferably containing not more than 7 carbon atoms (e.g. acetoxy). The protected group may also be a C$_{2-7}$alkoxycarbonyloxy group, which can be optionally substituted (e.g. by halo), as in a trichloroethoxycarbonyloxy group.

Where OR$^h$ is tri(hydrocarbyl)silyloxy the hydrocarbyl substituents may be the same or different, e.g. C$_{1-6}$alkyl, C$_{2-6}$alkenyl, C$_{3-7}$cycloalkyl, C$_{7-20}$aralkyl and C$_{6-20}$aryl groups. Such groups include methyl, ethyl, n-propyl, isopropyl, n-butyl, isobutyl, t-butyl, allyl, phenyl and benzyl. Preferred hydrocarbyl groups and C$_{1-4}$alkyl, e.g. methyl and t-butyl. Trimethylsilyl and t-butyldimethylsilyl ethers are particularly preferred.

When OR$^h$ is an arylmethoxy group it may contain up to 20 carbon atoms, e.g. benzyloxy, diphenylmethoxy or triphenylmethoxy.

Particularly useful groups OR$^h$ include tri(hydrocarbyl)silyloxy groups, especially t-butyldimethylsilyloxy, and tetrahydropyranyloxy.

Deprotection of the protected hydroxy group will depend on the nature of R$^h$. Where appropriate, deprotection may be carried out in the presence of either an acid or a base or by reduction. Thus, for example, an acyl group may be removed by alkaline hydrolysis. A tri(hydrocarbyl)silyl group may, for example, be removed by acid hydrolysis, e.g. with dilute mineral acid or trifluoroacetic acid or by treatment with fluoride ions (e.g. from a quaternary ammonium fluoride such as tetra-n-butyl ammonium fluoride). Tetrahydropyranyl groups may for example be cleaved by acid hydrolysis, e.g. with a dilute mineral acid or trifluoroacetic acid. Arylmethyl groups may be removed by reduction, e.g. with an alkali metal such as sodium dissolved in liquid ammonia or by hydrogenolysis, e.g. with a noble metal catalyst such as platinum or palladium. Halogenated alkoxycarbonyl e.g. trichloroethoxycarbonyl groups may be removed by treatment with metallic zinc, e.g. in a suitable solvent such as tetrahydrofuran.

The following examples illustrate the invention. The synthesis of the itermediates required is described in the Preparations. Temperatures are in °C. "Petroleum ether" refers to the fraction boiling at 40°-60°.

The following abbreviations are used:
DMSO—dimethylsulphoxide
DMF—dimethylformamide
THF—tetrahydrofuran
PyTFA—pyridinium trifluoroacetate
Py—pyridine
Ac$_2$O—acetic anhydride
IPA—isopropanol
Dibal-diisobutyl aluminium hydride
Phos.salt—(4-carboxybutyl)triphenylphosphonium bromide
TLC—thin layer chromatography

PREPARATIONS 1-17

5,7-Disubstituted bicyclo[2.2.1]heptan-b 2-ones

Table 1 summarises the preparation of the title compounds by the following methods:

A. The appropriate amine was added to a stirred solution of the appropriate bicyclo[3.2.0]heptan-6-one in acetone at 0°14 10°. The solution was allowed to attain room temperature and stirring was continued for the time specified. Ether was added and stirring was continued for 30 mins, whereupon the mixture was filtered and the filtrate evaporated in vacuo. The residue was dissolved in ether and extracted with water followed by 5 N hydrochloric acid. The acidic extract was cooled and made basic by the addition of 5 N sodium hydroxide solution. The basic solution was extracted with dichloromethane and the combined extracts dried and evaporated.

B. A solution of the appropriate bicyclo[3.2.0]heptan-6-one in dichloromethane was added to a mixture of 5 N sodium hydroxide, benzyl triethylammonium chloride and the appropriate amine in dichloromethane at room temperature and stirring continued for the time specified. The reaction mixture was poured into water and extracted with dichloromethane. The combined extracts were washed, dried and evaporated. The material obtained was purified either by chromotagraphy on silica gel or by crystallisation.

C. To a stirred solution of potassium tert-butoxide in dry tetrahydrofuran under nitrogen at −70° was added dropwise a solution of the appropriate bicyclo[3.2.0-]heptan-6-one in dry tetrahydrofuran. Stirring was continued for 30 mins whereupon dry ether and charcoal were added. The mixture was filtered and the filtrate evaporated to a volume of about 150–200 ml. To the resulting solution of the 3-endo-substituted tricyclo[3.2.0.0$^{2,7}$]heptan-6-one at 0° was added the appropriate amine and the mixture was then stirred at room temperature for the time specified. The solvent was removed in vacuo and the residue purified by chromatography on silica gel.

TABLE I

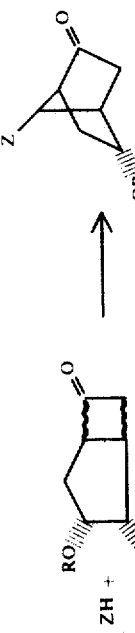

ZH + [bromo-hydroxy cyclopentane structure] → [bicyclic ketone structure]

| Prep. No. | Starting material R | Wt (g) | Amine Z | Wt (g) | Method | Acetone vol. (ml) | CH₂Cl₂ vol. (ml) | THF Total vol. (ml) | 5N NaOH Vol. (ml) | Benzyl triethyl ammonium chloride wt (g) | KO$^t$Bu wt (g) | Time (hr) | Chromatography Solvent | Yield (g) | IR >C=O cm$^{-1}$ | m.p. |
|---|---|---|---|---|---|---|---|---|---|---|---|---|---|---|---|---|
| 1 | —COCH₃ | 14.9 | morpholine (O) | 25 | C | — | — | 400 | — | — | 8.2 | 18 | ether | 12.1 | (Neat) 1755, 1740 | — |
| 2 | —CH₂—Ph | 118 | morpholine (O) | 139 | A | 1000 | — | — | — | — | — | 18 | — | 114.5 | (CHBr₃) 1744 | 139–140.5° from ethyl acetate-cyclohexane |
| 3 | —CH₂—Ph | 5.9 | piperidine | 5 | A | 35 | — | — | — | — | — | 24 | — | 5.26 | (CHBr₃) 1740 | 106–7° from petroleum ether |
| 4 | —CH₂—Ph | 8.85 | N-methylpiperazine | 9 | A | 100 | — | — | — | — | — | 18 | — | 9.3 | (CHBr₃) 1740 | 107–8° from petroleum ether |
| 5 | —CH₂—Ph | 8.11 | thiomorpholine (S) | 4 | B | — | 60 | — | 25 | 0.65 | — | 48 | 9:1 CH₂Cl₂–ether | 7.35 | (CHBr₃) 1740 | 136–40° from CH₂Cl₂–ether |
| 6 | —CH₂—Ph | 29.5 | N-methyl-N-benzylamine | 26.6 | A | 250 | — | — | — | — | — | 3 | — | 18.71 | (CHBr₃) 1743 | 59–60° from isopropanol |

TABLE I-continued

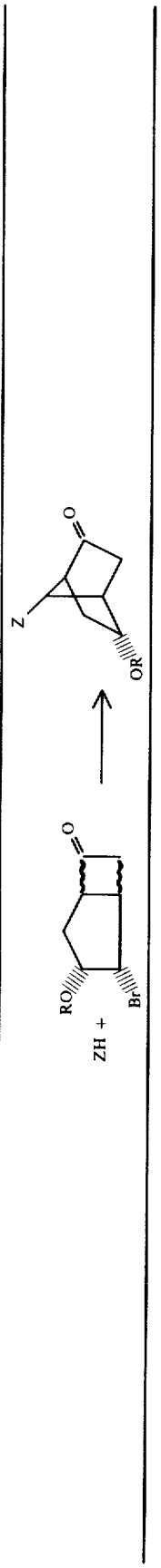

| Prep. No. | Starting Material R | Wt (g) | Amine Z | Wt (g) | Method | Acetone Vol (ml) | CH$_2$Cl$_2$ Vol (ml) | THF Total Vol (ml) | 5N NaOH Vol (ml) | Benzyl triethyl ammonium chloride wt (g) | KO$^t$Bu (wt) (g) | Time hr | Chromatography Solvent | Yield (g) | IR >=O cm$^{-1}$ | | m.p. |
|---|---|---|---|---|---|---|---|---|---|---|---|---|---|---|---|---|---|
| 7 | —CH$_3$ | 43.8 | CH$_3$—N—CH$_2$—C$_6$H$_5$ | 100 | A | 150 | — | — | — | — | — | 5 | 1:1 ether-petroleum ether | 39.8 | (CHBr$_3$) | 1745 | 58–62° |
| 8 | —CH$_2$—C$_6$H$_5$ | 44.4 | CH$_3$—N—CH$_2$CH$_2$—C$_6$H$_5$ | 41 | C | — | — | 800 | — | — | 21.9 | 21 | ether | 40 | (CHBr$_3$) | 1740 | — |
| 9 | —CH$_2$—C$_6$H$_5$ | 5.9 | OH—OCH$_2$CH—CH$_2$—N—CH$_3$—C$_6$H$_5$ | 5.43 | B | — | 40 | — | 20 | 0.59 | — | ? | ether | 6.6 | (Neat) | 1748 | — |
| 10 | —CH$_3$ | 65.7 | morpholinyl (N—O) | 130.5 | A | 375 | — | — | — | — | — | 1.5 | — | 53.8 | (CHBr$_3$) | 1745 | 86–7° from petroleum ether |
| 11 | —CH(CH$_3$)$_2$ | 5.0 | morpholinyl (N—O) | 8.81 | A | 30 | — | — | — | — | — | 4.5 | — | 3.8 | | 1740 | 82–3° from petrol. ether |
| 12 | tetrahydropyranyl | 8.67 | CH$_3$—N—CH$_2$CH$_2$—C$_6$H$_5$ | 8.6 | B | — | 60 | — | 30 | 0.87 | — | 20 | ether | 8.9 | | 1740 | b.p. 180° at 0.1 mm Hg |

TABLE I-continued

ZH + [bromoketone structure: RO, Br on cyclopentanone] → [bicyclic ketone with Z and OR]

| # | R | | ZH | | | | | | | | | | | | m.p./recryst. |
|---|---|---|---|---|---|---|---|---|---|---|---|---|---|---|---|
| 13 | —CH$_2$—Ph | 11.8 | HO—[4-hydroxy-4-(CH$_3$(CH$_2$)$_3$)piperidine]— | 9.4 | B | 30 | — | 30 | 1.18 | 18 | — | 12.7 | 1742 | 126–7° from isopropanol |
| 14 | —CH$_2$—Ph | 5.9 | CH$_3$—N—CH$_2$CHCH$_2$OCH$_2$Ph, OH | 5.4 | B | 40 | — | 20 | 0.59 | 2 | ether | 6.6 | 1743 | — |
| 15 | —CH$_2$—Ph | 3 | [azepan-1-yl] | 2.02 | B | 30 | — | 20 | 0.3 | 20 | ether-petroleum ether 2:3 | 2.3 | 1740 | 35.5–7° from petroleum ether |
| 16 | —CH$_2$—Ph | 10 | cis:trans 83:17 [2,6-dimethylmorpholin-4-yl, CH$_3$] | 11.9 | A | 50 | — | — | — | 4.5 | — | 9.5 | 1740 | 108–8.5° from petroleum ether |
| 17 | —CH(CH$_3$)$_2$ | 5 | [piperidin-1-yl] | 4.3 | A | 80 | — | — | — | 18 | ether | 5.0 | 1742 | 54–5° from methanol-water |

PREPARATION 18

(±)-7-anti-(4-Morpholinyl)-5-endo-(2-phenylethoxy)-bicyclo[2.2.1]heptan-2-one, hydrochloride N-Bromosuccinimide (26.6 g) was added in portions over 1.5 h to a cooled (−5°) solution of bicyclo[3,2,0]hept-2-en-6-one (10.8 g) in 2-phenylethanol (54.9 g) and stirring continued for a further 21 h. The mixture was diluted with dichloromethane (150 ml) and then washed with water (200 ml). The aqueous phase was extracted with dichloromethane (2×80 ml). The combined organic phases were washed successively with sodium sulphite (80 ml), water (2×100 ml) and brine, then dried (MgSO₄) and concentrated to afford a viscous oil. This was dissolved in acetone (50 ml), cooled (0°) and treated with morpholine (26.1 g). After 3 h at room temperature the mixture was poured into 2 N hydrochloric acid (60 ml) and extracted with ether (100 ml). The acidic layer was basified with 2 N sodium hydroxide and extracted into ether (3×100 ml). The combined extracts were washed with brine, dried (MgSO₄) and concentrated to afford a viscous oil. The product was dissolved in dry ether and treated with ethereal hydrogen chloride. The title compound was purified from isopropanol as an off-white solid (11.3 g) m.p. 156°–158°.

PREPARATION 19

(±)-2-exo-Bromo-3-endo-(1-methylethoxy)bicyclo[3,2,0]heptan-6-one

N-Bromoacetamide (83 g) was added portionwise to a cold (0°) solution of bicyclo[3,2,0]hept-2-en-6-one (54 g) in isopropanol (500 ml). The mixture was stirred overnight, poured into water (1 liter) and extracted into ether (2×500 ml). The combined extracts were washed with sodium sulphite solution, followed by brine, dried (over MgSO₄) and filtered and evaporated to afford a viscous oil (111 g). The crude product was chromatographed on silica gel (3.5 kg) using 1:4 ether-petroleum ether (b.g. 40°-60°) as eluent. The title compound was obtained as a solid (33.8 g) which was further purified by crystallisation from petroleum ether (b.p. 60°-80°) giving m.p. 36°-37°.

PREPARATION 20

(±)-5-endo-(2-Phenylethoxy)-7-anti-(1-piperidinyl)-bicyclo[2,2,1]heptan-2-one

The title compound (19.3 g) was prepared from bicyclo[3.2.0]hept-2-en-6-one (20 g) by the method described for Preparation 18. A sample was purified from petroleum ether as colourless microcrystals m.p. 72°–74°.

PREPARATION 21

(±)-1-(Methylamino)-3-phenoxy-2-propanol

To a solution of 1,2-epoxy-3-phenoxypropane (15 g), in ethanol (50 ml) was added 25–30% methylamine in water (50 ml) and the mixture heated under reflux for 1 h. The ethanol was removed in vacuo and the residue acidified with 2 N hydrochloric acid. The aqueous solution was extracted with ether acetate then made alkaline with 2 N sodium hydroxide and extracted into ether. The combined ethereal extracts were dried (Na₂SO₄), filtered and evaporated to give a semi-solid (14.8 g). The product was distilled in vacuo to give the title compound as white crystals b.p. 110°/0.07 mm, m.p. 74°–77° (9 g).

PREPARATION 22

(±)-7-anti-Azido-5-endo-(phenylmethoxy)bicyclo[2.2.1]heptan-2-one 2-exo-Bromo-3-endo-(phenylmethoxy)bicyclo[3,2,0]heptan-2-one (25 g) in dichloromethane (85 ml) was added dropwise to a rapidly stirred mixture of sodium azide (6.9 g), benzyl triethylammonium chloride (2.5 g), 5 N sodium hydroxide (85 ml) and dichloromethane (85 ml). The resultant mixture was stirred at room temperature for 18 h and then treated with water (700 ml). The separated aqueous phase was extracted with dichloromethane (2×600 ml) and the combined organic phases dried (MgSO₄) and evaporated to afford an oil which crystallised on seeding (21.5 g). Trituration with petroleum ether gave the title comopund as a white solid m.p. 37°–39° (20.0 g).

PREPARATION 23

(±)-2-anti-(4-Morpholinyl)-5-endo-(1-phenylethoxy)-bicyclo[2.2.1]heptan-2-one

A mixture of 2-bromo-3-hydroxybicyclo[3.2.0]heptan-6-one (15 g), α-methylbenzyl alcohol (36 g) and p-toluenesulphonic acid (1 g) was heated at 90° for 6 h. The solution was poured into 8% sodium bicarbonate (300 ml) and extracted with ether (4×150 ml). The combined extracts were washed with brine (300 ml), dried (MgSO₄) and evaporated to afford crude 2-bromo-3-(1-phenylethoxy)bicyclo[3.2.0]heptan-6-one as a pale yellow oil (29.1 g). The crude product (28.1 g) was dissolved in acetone (50 ml) and treated with morpholine (19 ml). The mixture was stirred for 3 h, poured into water (200 ml) and extracted with ether (4×150 ml). The combined extracts were washed with brine (200 ml), dried (MgSO₄) and evaporated. The product was purified by chromatography on silica eluting with ether-petroleum ether (7:3) to give the title compound as a waxy solid (15.7 g). I.R. (CHBr₃) 1745 cm⁻¹.

PREPARATION 24

(±)-(5-endo,7-anti)-N-[5-Phenylmethoxy)-2-oxobicyclo[2.2.1]hept-7-yl]phthalimide To a stirred solution of 2-exobromo-3-endo-(phenylmethoxy)bicyclo[3.2.0]heptan-6-one (1 g) in dimethyl sulphoxide (10 ml) was added potassium phthalimide (2 g) and the suspension stirred for 3 days. The mixture was poured into water (100 ml) and extracted with ethyl acetate (4×30 ml). The combined organic phase were washed successively with 2 N sodium hydroxide solution (2×30 ml) and brine, dried (MgSO₄) and concentrated. The residual oil crystallised slowly on standing. Recrystallisation from iso-propanolmethanol gave the title compound as colourless needles (0.8 g) m.p. 130°–31°.

PREPARATION 25

(±)-5-endo[[(1,1'-Biphenyl)-4-yl]methoxy]-7-anti-(4-morpholinyl)bicyclo[2.2.1]heptan-2-one The title compound (0.42 g) was prepared from 2-bromo-3-hydroxybicyclo[3.2.0]heptan-6-one (0.5 g), 4-phenylbenzyl alcohol (0.75 g) and morpholine (5 ml) according to the method of Preparation 23. The oily product was purified using ether-petroleum ether 4:1 as eluent. I.R. (Neat) 1750 cm⁻¹.

PREPARATION 26-46

6,8-Disubstituted 2-oxabicyclo[3.2.1]octan-3-ones

Table 2 summarises the preparation of the title compounds by the following methods:

A. To a stirred solution of the appropriate bicyclo[2.2.1]heptan-2-one in glacial acetic acid at 5° was added dropwise 6.12 M peracetic acid.

B. As described in Method A with sodium acetate and water added.

The solutions obtained from methods A and B were slowly allowed to attain ambient temperature when stirring was continued for the time specified. Excess peracid was destroyed by the addition of saturated sodium sulphite solution whilst maintaining the temperature below 20°. The acetic acid was removed in vacuo and the residue diluted with water, basified with 8% sodium bicarbonate solution and extracted with the solvent indicated. The combined organic extracts were washed, dried and evaporated. The product obtained was purified by crystallisation or by chromatography on silica gel.

TABLE 2

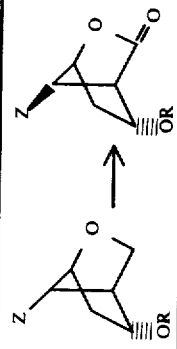

| Prep. No. | Starting Material Z | R | Wt (g) | Product Z | Method | Acetic acid vol. (ml) | Peracetic acid vol. (ml) | Sodium acetate wt (g) | Water vol. (ml) | Time hr | Extraction solvent | Chromatography solvent | Yield (g) | IR >C=O cm$^{-1}$ | m.p. |
|---|---|---|---|---|---|---|---|---|---|---|---|---|---|---|---|
| 26 | morpholine (O in ring) | —COCH$_3$ | 13.5 | morpholine | A | 70 | 40.5 | — | — | 18 | ethyl acetate | — | 10.1 | (CHBr$_3$) 1740 | 163–4° from ethyl acetate cyclohexane |
| 27 | morpholine | —CH$_2$—Ph | 24 | morpholine | A | 200 | 50 | — | — | 18 | ethyl acetate | — | 18.3 | (CHBr$_3$) 1733 | 164–5° from ethyl acetate cyclohexane |
| 28 | piperidine | —CH$_2$—Ph | 74.8 | piperidine | B | 450 | 204 | 102.5 | 187 | 24 | ethyl acetate | ether | 28 | (CHBr$_3$) 1728 | 105.5–107° |
| 29 | N-methylpiperazine | —CH$_2$—Ph | 13.6 | N-methylpiperazine | B | 160 | 51 | 24.9 | 16 | 30 | ethyl acetate | — | 5.7 | (CHBr$_3$) 1730 | 104–5° from 119 isopropanol petroleum ether |
| 30 | thiomorpholine-S,S-dioxide | —CH$_2$—Ph | 1 | thiomorpholine-S,S-dioxide | B | 10 | 4 | 1.3 | 1 | 20 | dichloromethane | — | 0.47 | (CHBr$_3$) 1736 | 181–4° from ethyl acetate |
| 31 | N(CH$_3$)(CH$_2$Ph) | —CH$_2$—Ph | 10 | N(CH$_3$)(CH$_2$Ph) | B | 40 | 28 | 12 | 16 | 21 | ethyl acetate | 65:35 ether-petroleum ether | 3.41 | (CHBr$_3$) 1730 | 52° |

TABLE 2-continued

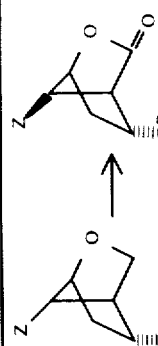

| Prep. No. | Z | R | Ketone Wt (g) | Method | Acetic Acid Vol. (ml) | Peracetic Acid Vol. (ml) | Sodium Acetate Wt. (g) | Water Vol. (ml) | Time (hr) | Extraction Solvent | Chromatography Solvent | Yield (g) | IR >=O cm⁻¹ | m.p. |
|---|---|---|---|---|---|---|---|---|---|---|---|---|---|---|
| 32 | CH₃—N—CH₂—C₆H₅ | —CH₃ | 5.2 | B | 20 | 8.2 | 4.1 | 100 | 24 | 10 | ethyl acetate | ether | 2 | (CHBr₃) 1730 | 48-9° from ethanol |
| 33 | CH₃—N—CH₂CH₂—C₆H₅ | —CH₂—C₆H₅ | 2.4 | A | 32 | 3.45 | — | — | — | ethyl acetate | — | 0.95 | (CHBr₃) 1730 | 82-3° from chloroform-petroleum ether |
| 34 | CH₃—N—OCH₂CHCH₂OH—C₆H₅ | —CH₂—C₆H₅ | 9 | B | 50 | 17.5 | — | 9.41 | 20 | 48 | ethyl acetate | ether | 3.21 | (Neat) 3450, 1740 | — |
| 35 | phthalimide-like N | —CH₂—C₆H₅ | 50 | B | 750 | 140 | — | — | 60 | 48 | ethyl acetate | — | 22.3 | (CHBr₃) 1780, 1786, 1710 | 111-112° from methanol |
| 36 | morpholino | —CH₃ | 2.25 | B | 10 | 8.2 | — | — | 25 | ethyl acetate | — | 0.77 | 1730 | 122-4° from ethyl acetate petrol.ether |
| 37 | morpholino | —CH₂CH₂—C₆H₅ | 14 | B | 100 | 59.1 | 25.5 | 40 | 25 | ethyl acetate | 95:5 ether-petroleum ether | 5.77 | 1730 | 82.5-83.5° from petroleum ether |

TABLE 2-continued

| | | | | | | 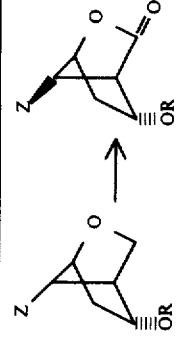 → 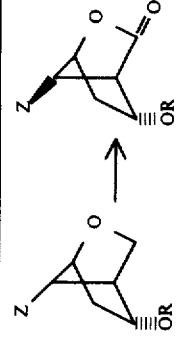 | | | | | | |
|---|---|---|---|---|---|---|---|---|---|---|---|---|
| 38 | 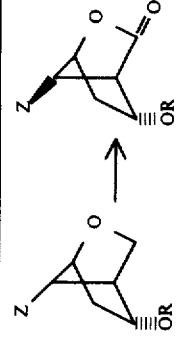 | —CH(CH$_3$)$_3$ | 3.3 | B | 26.7 | 12.4 | 5.3 | 10.7 | 24 | ethyl acetate | — | 1.28 | 1730 | 107–9° from ethyl acetate-petroleum |
| 39 | CH$_3$—N—CH$_2$CH$_2$— | 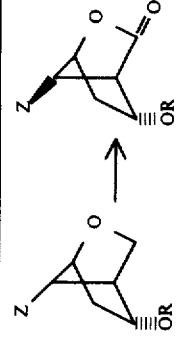 | 5.0 | A | 25 | 11 | — | — | 19 | ethyl acetate | ether | 1.45 | 1730 | ether |
| 40 | N$_3$— | —CH$_2$— phenyl | 40 | B | 200 | 59.1 | 31.9 | 100 | 67 | ethyl acetate | — | 11.4 | 1740 | 39–43° from isopropanol |
| 41 | HO— CH$_3$(CH$_2$)$_3$ piperidine | —CH$_2$— phenyl | 10.5 | B | 50 | 26.9 | 11.6 | 20 | 24 | ethyl acetate | ethyl acetate | 2.4 | 1730 | 112° from isopropanol |
| 42 | 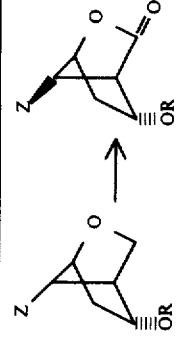 | —CH$_2$— phenyl | 10 | B | 64 | 24.2 | 13.1 | 26 | 20 | ethyl acetate | 7:3 ether-petroleum ether | 1.9 | 1730 | 74–5° from ethyl acetate-petroleum ether |
| 43 | 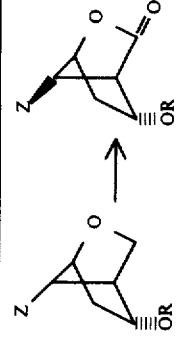 | —CH$_2$— phenyl | 9.5 | B | 59 | 23.6 | 11.8 | 24 | 24 | ether | — | 4.1 | 1738 | 93° from petroleum ether |

TABLE 2-continued

| | | | | | | | | | | |
|---|---|---|---|---|---|---|---|---|---|---|
| 44 | ![morpholine] —N⟩O | 5.4 | B | 50 | 13.5 | 7.1 | 20 | 72 | ether | ether | 2.4 | 1733 | — |
| 45 | ![piperidine] —N⟩ | 5.64 | B | 40 | 9 | 9.2 | 17 | 24 | ether | 1:1 ether-petroleum ether | 1.0 | 1730 | — |
| 46 | ![piperidine] —N⟩ | 10 | B | 80 | 26.1 | 13.1 | 40 | 24 | dichloromethane | 1:1 ether-petroleum ether | 2.2 | 1740 | — |

—CH(CH₃) (row 44)
—CH(CH₃)₂ (row 45)
—CH₂CH₂ (row 46)

PREPARATIONS 47-66

6,8-Disubstituted-2-oxabicyclo[3.2.1]octan-3-ols

Table 3 summarises the preparation of the title compounds by the following procedure:

A solution of di-isobutyl aluminium hydride (2.02 M in hexane) was added dropwise to a stirred solution of the appropriate 2-oxa-bicyclo[3.2.1]octan-3-one in the dry solvent specified at $-78°$ under nitrogen. After the time specified methanol was carefully added and the mixture then allowed to attain room temperature. Filtration and evaporation in vacuo gave the product usually as an oil or foam. Where necessary purification was effected by chromatography on silica gel.

PREPARATION 67

(±)-3-endo-Hydroxy-2-exo-(4-morpholinyl)bicyclo[3.2.0]heptan-6-one

A mixture of $(1\alpha,2\alpha,4\alpha,6\alpha)$-3-oxatricyclo[4,2,0,0$^{2,4}$]octan-7-one (5.3 g) and morpholine (20 g) was allowed to stand at room temperature for 3 days. The morpholine was removed in vacuo and the residue was chormatographed on silica gel using ether-methanol (17:3) as eluent to give the tilte compound as a solid (5.58 g). Crystallisation from ethyl acetate gave material of m.p. 102°-104.5°.

TABLE 3

| Prep. No. | Starting material Z | Starting material R | Wt (g) | Di-bal vol. (ml) | Solvent | Vol. (ml) | Time (hr) | Methanol vol. (ml) | Chromatography solvent | Yield (g) | IR cm$^{-1}$ |
|---|---|---|---|---|---|---|---|---|---|---|---|
| 47 | O-morpholinyl | —CH$_2$—Ph | 0.4 | 4.8 | 1,2-dimethoxyethane | 30 | 1 | 10 | 5% methanol ethyl acetate | 0.3 | (CHBr$_3$) 1715 |
| 48 | piperidinyl | —CH$_2$—Ph | 10 | 31.4 | 1,2-dimethoxyethane | 500 | 3 | 500 | — | 10.0 | (Neat) 3400(br) 1718 |
| 49 | CH$_3$N-piperazinyl | —CH$_2$—Ph | 4.25 | 19.1 | Dichloromethane | 120 | 2 | 120 | — | 4.25 | (CHBr$_3$) 3540, 1717 |
| 50 | O$_2$S-morpholinyl | —CH$_2$—Ph | 0.5 | 1.4 | Dichloromethane | 20 | 0.5 | 20 | — | 0.45 | (CHBr$_3$) 1716, 1040, 1330 |
| 51 | CH$_3$(PhCH$_2$)N— | —CH$_2$—Ph | 5.86 | 17.1 | 1,2-Dimethoxyethane | 75 | 2 | 75 | — | 5.98 | (CHBr$_3$) 3420, 1720 |
| 52 | CH$_3$(PhCH$_2$)N— | —CH$_3$ | 4.13 | 22.3 | 1,2-Dimethoxyethane | 200 | 1.5 | 200 | — | 4.2 | (Neat) 3400, 1720 |
| 53 | CH$_3$(PhCH$_2$CH$_2$)N— | —CH$_2$—Ph | 1.46 | 5.94 | 1,2-Dimethoxyethane | 100 | 2 | 100 | — | 1.42 | (Neat) 1720 |
| 54 | $^t$BuOCONH— | —CH$_2$—Ph | 2.27 | 8 | Dichloromethane | 80 | 1.2 | 100 | — | 2.3 | |

TABLE 3-continued

| Prep. No. | Starting material Z | R | Wt (g) | Dibal vol. (ml) | Solvent | Vol. (ml) | Time (hr) | Methanol vol. (ml) | Chromatography solvent | Yield (g) | IR cm$^{-1}$ |
|---|---|---|---|---|---|---|---|---|---|---|---|
| 55 |  | —CH$_3$ | 5.0 | 20.5 | 1,2 dimethoxyethane | 250 | 3 | 250 | — | 5.03 | (CHBr$_3$) 3590, 1715 |
| 56 |  | —CH$_2$CH$_2$ | 3.0 | 9.0 | dichloromethane | 70 | 2 | 130 | — | 2.57 | (CHBr$_3$) 3540, 1715 |
| 57 |  | —CH(CH$_3$)$_2$ | 6.0 | 16.55 | dichloromethane | 120 | 0.75 | 130 | — | 5.6 | (CHBr$_3$) 3520, 1716 |
| 58 | 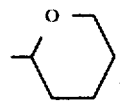 |  | 1.5 | 11.2 | 1,2 dimethoxyethane | 75 | 2 | 75 | — | 1.3 | (CHBr$_3$) 3500(br), 1715 |
| 59 |  | —CH$_2$ | 2.9 | 13.5 | 1,2 dimethoxyethane | 75 | 2.5 | 150 | — | 2.7 | (Neat) 3440, 1720 |
| 60 | H$_3$— | —CH$_2$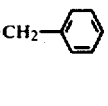 | 6.5 | 30 | 1,2 dimethoxyethane | 300 | 1.5 | 300 | — | 6.0 | (CHBr$_3$) 3580, 2100, 1720 |
| 61 |  | —CH$_2$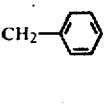 | 1.74 | 8.9 | dichloromethane | 40 | 2.5 | 80 | — | 1.65 | (CHBr$_3$) 3590, 1710 |
| 62 |  | —CH$_2$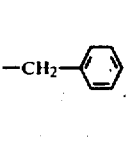 | 2.8 | 8.4 | dichloromethane | 50 | 1.0 | 50 | — | 2.8 | (CHBr$_3$) 3560, 1710 |
| 63 |  | —CH$_2$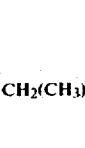 | 3.9 | 8.3 | dichloromethane | 60 | 2.5 | 165 | — | 4.1 | (Neat) 3430, 1720 |
| 64 |  | —CH$_2$(CH$_3$) | 2.2 | 6.5 | dichloromethane | 50 | 2.5 | 75 | — | 2.0 | (Neat) 3420, 1720 |

TABLE 3-continued

| Prep. No. | Starting material Z | R | Wt (g) | Di-bal vol. (ml) | Solvent | Vol. (ml) | Time (hr) | Methanol vol. (ml) | Chromatography solvent | Yield (g) | IR cm⁻¹ |
|---|---|---|---|---|---|---|---|---|---|---|---|
| 65 | piperidin-N— | —CH(CH₃)₂ | 1.34 | 6 | dichloromethane | 60 | 2 | 60 | — | 1.34 | (CHBr₃) 3550(br) 1715 |
| 66 | piperidin-N— | —CH₂CH₂—Ph | 1.9 | 7 | dichloromethane | 70 | 2 | 70 | — | 1.62 | (Neat) 3400, 1720 |

PREPARATION 68

3aα,4β,5α,6aα)-(±)-Hexahydro-5-hydroxy-4-(4-morpholinyl)-2-H-cyclopenta-(b)furan-2-one (a) A solution of the product for Preparation 26 (8 g) in methanol (100 ml) containing conc. sulphuric acid (10 ml) was heated under reflux for 5 hr. The solution was cooled and made alkaline by the addition of solid sodium bicarbonate. The resulting suspension was filtered and the residue washed with chloroform (100 ml). The filtrate was evaporated and the residue taken up on chloroform (100 ml). Filtration and evaporation gave the title compound as a solid which was recyrstallised from isopropanol (4.85 g) m.p. 146°-8°.

(b) A solution of the product of Preparation 67 (0.5 g) in dichloromethane (8 ml) containing sodium acetate (0.58 g) was cooled to −10° with stirring and peracetic acid (0.44 ml, 6.1 M) was added dropwise over about 1 min. stirring at 10° was contained for a further 10 min. when an excess of saturated sodium sulphite solution was added. Adjustment of the pH to 8 by solid sodium bicarbonate followed by extraction with dichloromethane, drying (MgSO₄), filtration and concentration gave the title compound as a solid (0.2 g).

PREPARATION 69

(3aα,4β,5α,6aα)-(±)-Hexahydro-5-hydroxy-[N-methyl-N-(2-hydroxy-3-phenoxy-propyl)amino]-2H-cyclopenta(b)furan-2-one A rapidly stirred solution of the product from Preparation 34 (2.04 g) in ethanol (30 ml) and 2 N hydrochloric acid (10 ml) was hydrogenated over pre-reduced 10% palladium oxide on charcoal (0.35 g) at atmospheric pressure. The catalyst was filtered off and the filtrate evaporated. The residue was diluted with brine, neutralised with aqueous sodium bicarbonate solution and extracted with ethyl acetate. The combined extracts were dried and concentrated. The material obtained was chromatographed on silica gel using 10% methanol in ether as eluent to yield the title compound as an oil (1.11 g) IR (Neat) 3400, 1765 cm⁻¹.

PREPARATION 70

(3aα,4β,5α,6aα)-(±)-Hexahydro-4-(4-morpholinyl)-5-(tetrahydro-2H-pyran-2-yl)oxy-2H-cyclopenta(b)furan-2-one To a solution of the product from Preparation 68 (10 g) and 2,3-dihydropyran (25 ml) in dioxan (300 ml) at 0° was added p-toluene-sulphonic acid monohydrate (8.83 g). The solution was gradually allowed to attain ambient temperature when stirring was continued for 3 hr. The solvent was evaporated in vacuo and the residue treated with 8% sodium bicarbonate solution (250 ml). Extraction with dichloromethane, drying and evaporation gave an oil. The material was purified by column chromatography on silica gel using 7:3 ether-methanol as eluent. The title compound crystallised on standing and was recrystallised from isopropanol-cyclohexane (8.63 g) m.p. 103°-4°.

PREPARATION 71

(3aα,4β,5α,6aα)-(±)-Hexahydro-4-[N-methyl-N-[3-phenoxy-2-[(tetrahydro-2H-pyran-2-yl)oxy]propyl]amino]-5-(tetrahydro-2H-pyran-2-yl)oxy-2H-cyclopenta(b)furan-2-one The title compound was prepared from the product of Preparation 69 according to the method of Preparation 70. IR (Neat) 1770 cm⁻¹.

PREPARATION 72

(3aα,4β,5α,6aα)-(±)-Hexahydro-5-hydroxy-4-(4-morpholinyl)-2H-cyclopenta(b)furan-2-ol The title compound was prepared from the product of Preparation 26 (538 mg) in dry 1,2-dimethoxyethane (35 ml) by the method of Preparations 47-66. Purification by chromatography on silica gel using 4:1 ethyl acetate-methanol as eluent gave a solid (305 mg). Recrystallisation from ethyl acetate-methanol gave the title compound, m.p. 136°-7°.

PREPARATION 73

(3aα,4β,5α,6aα)-(±)-Hexahydro-4-(4-morpholinyl)-5-(tetrahydro-2H-pyran-2-yl)oxy-2H-cyclopenta(b)furan-2-ol A solution of the product of Preparation 70 (6.3 g) in dry 1,2-dimethoxyethane (300 ml) was treated with a hexane solution of di-isobutylaluminium hydride and methanol according to the method of Preparations 47–66. Charcoal (2 g) was then added, the suspension allowed to attain room temperature and stirred for a further 1 hr. The mixture was filtered and the filtrate evaporated. The residue was treated with dichloromethane (250 ml), the solution dried, filtered and evaporated in vacuo to yield an oil (6.25 g), which slowly crystallised. Recrystallisation from ethyl acetate-petroleum ether gave the title compound m.p. 125°–6°.

PREPARATION 74

(3aα,4β,5α,6aα)-(±)-Hexahydro-4-[N-methyl-N-[3-phenoxy-2-[(tetrahydro-2H-pyran-2-yl)oxy]propyl]amino]-5-(tetrahydro-2H-pyran-2-yl)oxy-2H-cyclopenta(b)furan-2-ol The title compound was prepared from the product of Preparation 71 according to the method of Preparation 73. Purification was by chromatography on silica gel using 96:4 ether-methanol as eluent. IR (Neat) 3410 cm$^{-1}$.

PREPARATION 75

(±)-1-(methylamino)-2-heptanol

To a stirred solution of m-chloroperbenzoic acid (100 g) in dichloromethane (900 ml) was added a solution of 1-heptene (44.8 g) in dichloromethane (50 ml) and the mixture stirred overnight at room temperature. The excess peracid was destroyed with 10% aqueous sodium sulphite solution, the organic layer separated, washed with 8% aqueous sodium bicarbonate solution and dried. The solvent was evaporated in vacuo and the residue dissolved in ethanolic methylamine (30% w/w, 340 ml), and stirred at room temperature for 48 hr. Evaporation of the solvent gave an oil which was purified by distillation (b.p. 94°–6°/2 mm) to give the title compound as a solid, m.p. 40°–3°.

PREPARATION 76

(3aα,4β,6aα)-(±)-4-[N-(2-Hydroxyheptyl)-N-methylamino]-3,3a,4,6a-tetrahydro-2H-cyclopenta(b)furan-2-one A mixture of (3aα,6β,6aα)-6-bromo-3,3a,6,6a-tetrahydro-2H-cyclopenta(b)furan-2-one (2.03 g) and 1-methylamino-2-heptanol (3 g) in dry acetonitrile (20 ml) was stirred at ambient temperature for 24 hr. The solvent was evaporated in vacuo and the residue chromatographed on silica gel. Elution with ether-methanol (19:1) increasing to (4:1) gave the title compound as an oil (1.95 g). IR (Neat) 3450, 1775 cm$^{-1}$.

PREPARATION 77

(3aα,4β,6aα)-(±)-4-[N-(2-Hydroxyheptyl)-N-methylamino]-3,3a,4,6a-tetrahydro-2H-cyclopenta(b)furan-2-ol To a stirred solution of the product of Preparation 76 (1.95 g) in dry 1,2-dimethoxyethane (50 ml) at −78° under nitrogen was added dropwise a hexane solution of di-isobutyl aluminium hydride (8.9 ml, 2.02 M). The solution was stirred for 1 hr and then treated with a further aliquot of di-isobutyl aluminium hydride (2.0 ml). After stirring for a further 1 hr methanol (150 ml) was carefully added and the mixture then allowed to attain room temperature. Filtration and evaporation gave the title compound as a gum (1.7 g). IR (Neat) 3400 cm$^{-1}$.

PREPARATION 78

(3aα,4β,5α,6aα)-(±)-Hexahydro-5-[[(1,1-dimethylethyl)dimethylsilyl]oxy]-4-(4-morpholinyl)-2H-cyclopenta(b)furan-2-one A mixture of Preparation 68 (454 mg), dimethyltertiary butyl silyl chloride (302 mg) and imidazole (340 mg) in dry dimethylformamide (3 ml) was stirred at room temperature for 20 h. Excess solvent was removed under high vacuum. The residual oil was treated with water (20 ml) and extracted with ether (3×50 ml). The organic phase was then dried ($K_2CO_3$) and evaporated to afford a solid (430 mg). The title compound was purified from petroleum ether (b.p. 60°–80°) as colourless platelets (320 mg) m.p. 88°–90°.

PREPARATION 79

(3aα,4β,5α,6aα)-(±)-Hexahydro-5-[[(1,1-dimethylethyl)dimethylsilyl]oxy]-4-(4-morpholinyl)-2H-cyclopenta(b)furan-2-ol The title compound was prepared from the product of Preparation 78 (1.7 g) in dry dichloromethane (50 ml) by the method of Preparations 47–66. The product (1.61 g) was purified from isopropanol/cyclohexane as fine colourless platelets, m.p. 88°–89°.

PREPARATION 80

(3aα,4α,6aα)-(±)-Tetrahydro-4-(4-morpholinyl)-2H-cyclopenta(b)furan-2-one

A solution of (3aα,6α,6aα)-(±)-6-bromo-tetrahydro-2H-cyclopenta(b)furan-2-one (2.02 g) in dry acetone (60 ml) containing morpholine (8 ml) was stirred at room temperature for 24 h. The hydrobromide was filtered off and the solvent removed in vacuo. The residue was dissolved in dichloromethane and the organic phase was extracted with water (3×) to remove the excess of morpholine. The dichloromethane solution was washed with brine, dried ($MgSO_4$) and evaporated to give a solid. The residue was triturated with ether to give an off-white solid which was purified from ethyl acetate-petroleum ether as tan microcrystals (1.43 g) m.p. 96°–98°.

PREPARATION 81

(3aα,4α,6aα)-(±)-Tetrahydro-4-(4-morpholinyl)-2H-cyclopenta(b)furan-2-ol

A solution of the product of Preparation 80 (3 g) in dry dichloromethane (100 ml) was cooled to −70° under nitrogen. A solution of diisobutyl aluminium hydride (Dibal) in hexane (1.0 molar, 30 ml) was added dropwise with stirring. The reaction mixture was stirred at −70° for 1 h. Cold methanol (100 ml) was added cautiously at −70° and then the mixture was allowed to warm to room temperature, with further stirring for 1 h. The mixture was filtered (hyflo) and the solvents were removed in vacuo. The residue was dissolved in dry dichloromethane and the solution was dried ($MgSO_4$) and evaporated to give a solid (3.0 g). A portion (470 mg) was purified from ethyl acetate-petrol as a white solid (332 mg) m.p. 100°–103°.

PREPARATION 82

(3aα,4α,6aα)-(±)-Hexahydro-4-(4-morpholinyl)-2H-cyclopenta(b)furan-2-one

A solution of the product of Preparation 80 (1 g) in ethyl acetate (30 ml) was hydrogenated over pre-reduced 5% rhodium on charcoal (250 mg) in ethyl acetate (20 ml), at atmospheric pressure for 30 min. The catalyst and the solvent were removed and the residue in dichloromethane was washed with 8% sodium bicarbonate solution. The solvent was dried and evaporated to give a solid (583 mg, m.p. 59°–61°) which was purified from ether-light petroleum to give the title compound (380 mg) m.p. 65°–67°.

PREPARATION 83

(3aα,4α,6aα)-(±)-Hexahydro-4-(4-morpholinyl)-2H-cyclopenta(b)furan-2-ol

The title compound (2.2 g) was prepared from the product of Preparation 82 (2.11 g) in dichloromethane (75 ml) by the method of Preparations 47–66. I.R. (Neat) 3400 cm$^{-1}$.

PREPARATION 84

(3aα,4α,5β,6aα)-(±)-Hexahydro-5-[[(1,1'-biphenyl)-4-yl]methoxy]-4-(4-morpholinyl)cyclopenta(b)furan-2-one The product of Preparation 68 (1.85 g) was alkylated with biphenylmethyl bromide (4.02 g) as described for Examples 60–66 (Table 8)(Method B). The title compound was obtained as a pale yellow gum (1.87 g). A portion of the base was treated with ethereal hydrogen chloride to give the salt which as purified from ethyl acetate m.p. 231°–2°.

PREPARATION 85

(3aα,4α,5β,6aα)-(±)-Hexahydro-5-[[(1,1'-biphenyl)-4-yl]methoxy]-4-(4-morpholinyl)cyclopenta(b)furan-2-ol The title compound (1.21 g) was prepared from the product of Preparation 84 (1.47 g) in dichloromethane (70 ml) by the method of Preparations 47–66 I.R. (CHBr$_3$) 3580 cm$^{-1}$.

PREPARATION 86

(±)-8-anti-[N-Methyl-N-[3-phenoxy-2[(tetrahydro-2H-pyran-2-yl)oxy]propyl]amino]-6-endo-(phenylmethoxy)-2-oxabicyclo[3,2,1]octan-3-one Dihydropyran (4.9 g) was added dropwise to a stirred mixture of the product of Preparation 34 (Table 2)(2.4 g) and p-toluenesulphonic acid (1.11 g) in dioxan (15 ml). After 1.5 h the reaction mixture was quenched with sodium bicarbonate solution, extracted with ether (3×50 ml), dried (MgSO$_4$) and evaporated to give an oil. The product was chromatographed on silica gel and elution with ether:petroleum ether b.p. 40°–60° 4:1 gave the title compound as a yellow viscous oil (2.43 g). I.R. (CHBr$_3$) 1730 cm$^{-1}$.

PREPARATION 87

(3aα,4α,6aα)-(±)-Tetrahydro-4-[N-methyl-N-(phenylmethyl)amino]-2H-cyclopenta(b)furan-2-one A solution of (3aα,6α,6aα)-(±)-6-bromo-tetrahydro-2H-cyclopenta(b)furan-2-one (2.03 g) and N-methylbenzylamine (2.42 g) in acetone (40 ml) was stirred at ambient temperature for 3.5 days. The reaction mixture was diluted with ether (50 ml) and filtered to remove the precipitated N-methylbenzylamine hydrobromide. The solvent was removed and the residue in ether (60 ml) was washed with water (2×30 ml). The ethereal layer was extracted with 2 N hydrochloric acid (2×30 ml) and the combined extracts washed with ether (2×30 ml). The aqueous acidic layer was cooled to 0° (ice-water bath) and basified with concentrated ammonium hydroxide. The resultant aqueous mixture was extracted with ether (2×30 ml) and the organic phase washed with brine (30 ml). Drying (MgSO$_4$) and removal of the solvent gave an oil (2.0 g). Chromatography on silica gel with ether as eluent gave the product as a pale yellow oil (1.65 g) which was purified from isopropanol to give the title compound as white crystals m.p. 52°–52.5°.

PREPARATION 88

(3aα,4α,6aα)-(±)-Tetrahydro-4-[N-methyl-N-(phenylmethyl)amino]-2H-cyclopenta(b)furan-2-ol The title compound (10.25 g) was prepared from the product of Preparation 87 (10 g) in 1,2-dimethoxyethane (100 ml) by the method of Preparations 47–66. I.R. (CHBr$_3$) 3580 cm$^{-1}$.

PREPARATION 89

[3aα,4α,5β,6aα]-(±)-Hexahydro-5-hydroxy-4-(1-piperidinyl)-2H-cyclopenta(b)furan-2-one The product of Preparation 28 (15.1 g) in water (60 ml), concentrated hydrochloric acid (60 ml) and ethanol (160 ml) was added to prehydrogenated 10% palladium oxide on charcoal (3.75 g) in ethanol (150 ml) and stirred under a hydrogen atmosphere until the theoretical volume of hydrogen had been taken up (1214 ml at 21°). The mixture was filtered and the filtrate evaporated in vacuo. The residue was basified with 8% sodium bicarbonate solution and the solvent removed in vacuo. The residue was dried by addition of anhydrous potassium carbonate and the resultant slurry washed with dichloromethane (6×100 ml). The combined washings were evaporated to give the title compound (9.64 g). A sample (223 mg) was purified from ethyl acetate:petroleum ether (b.p. 60°–80°) to give colourless prisms m.p. 106°–106.5° (176 mg).

PREPARATION 90

[3aα,4α,5β,6aα]-(±)-Hexahydro-4-(1-piperidinyl)-5-[(tetrahydro-2H-pyran-2-yl)oxy]-2H-cyclopenta(b)furan-2-one Dihydropyran (15.1 g) was added to the product of Preparation 89 (10.1 g) and toluene-p-sulphonic acid monohydrate (10.23 g) in dichloromethane (730 ml) at 0° and the mixture then stirred at 0° for 2.5 h. The mixture was stirred at room temperature for 16 h, basified with 8% sodium bicarbonate solution (100 ml) and the basic layer extracted with dichloromethane (2×100 ml). The combined organic layers were dried (MgSO$_4$) and evaporated in vacuo to give an oil (27.7 g). Chromatography on silica with methanol:ether 3:17 as eluent gave the title compound as an orange oil (10.64 g). IR (CHBr$_3$) 1760 cm$^{-1}$.

PREPARATION 91

[3aα,4α,5β,6aα]-(±)-Hexahydro-4-(1-piperidinyl)-5-[(tetrahydro-2H-pyran-2-yl)oxy]-2H-cyclopenta(b)furan-2-ol

The title compound (11.4 g) was prepared from the product of Preparation 90 (10.5 g) in dichloromethane (210 ml) by the method of Preparations 47-66, Table 3. IR (CHBr$_3$) 3590, 3380 cm$^{-1}$.

PREPARATION 92

(±)-8-anti-Amino-6-endo-(phenylmethoxy)-2-oxabicyclo[3,2,1]octan-3-one

Hydrazine hydrate (0.99 ml) was added dropwise to a stirred solution of the product of Preparation 35 (7 g) in ethanol (75 ml) and the mixture heated under reflux for 9 h. The mixture was concentrated and the residue chromatographed on silica gel using 4:1 ether-methanol as eluent to give the title compound as a viscous oil (3.8 g). I.R. (CHBr$_3$) 3380 cm$^{-1}$.

PREPARATION 93

(±)-6-endo-8-anti-N-[3-Oxo-6-(phenylmethoxy)-2-oxabicyclo[3,2,1]oct-8-yl]carbamic acid, (1,1-dimethylethyl)ester

2-[1,1-Dimethylethoxy)carbonyloxyamino]-2-phenyl acetonitrile (0.142 g) was added dropwise to a stirred mixture of the product of Preparation 92 (0.13 g), dioxan (4 ml), water (2 ml) and triethylamine (0.08 g), and after the addition stirring was continued at room temperature for 22 h. The solution was treated with saturated ammonium chloride solution (50 ml) and extracted with dichloromethane (2×60 ml). The combined organic extracts were dried (MgSO$_4$) and concentrated, and the residue purified by chromatography on silica gel using 85:15 ether-petroleum ether as eluent to give the title compound as white needles (0.12 g), m.p. 102°-3°.

PREPARATION 94

(1α,2β,3β,5β)-(±)-N-[2-(2-Oxoethyl)-3-(phenylmethoxy)-5-[(tetrahydro-2H-pyran-2-yl)oxy]cyclopentyl]-carbamic acid, (1,1-dimethylethyl)ester

Dihydropyran (1.37 g) was added dropwise to a solution of the product of Preparation 54 (1.9 g) and pyridinium p-toluene sulphonate (2.05 g) in dry dichloromethane (100 ml) and the solution stirred at room temperature for 1 h. The mixture was treated with 8% aqueous sodium bicarbonate solution (100 ml) and extracted with dichloromethane. The combined organic extracts were washed with brine, dried (MgSO$_4$) and concentrated. The product was purified by chromatography on silica gel using 3:2 ether-petroleum ether as eluent to give the title compound as a solid (1.7 g), m.p. 50°-54°.

PREPARATIONS 95-98

7-(2,3,5-Trisubstituted)cyclopentyl-5-heptenoic acid, methyl esters

Table 4 summarises the preparation of the title compounds from 2H-cyclopenta(b)furan-2-ols by the following method:

Dry (4-carboxybutyl)triphenyl phosphonium bromide was added to a stirred solution of potassium tert-butoxide in dry tetrahydrofuran at room temperature under nitrogen and stirring continued for 15-30 mins. A solution of the appropriate 2H-cyclopenta(b)furan-2-ol in dry tetrahydrofuran was added dropwise and stirring continued at room temperature for the time specified. Ice was added to the reaction mixture followed by 2 M NaHSO$_4$ solution until pH 6 was attained. The mixture was then extracted with ethyl acetate or dichloromethane and the combined extracts washed and dried. The solution was treated with diazomethane in ether. The solvents were removed in vacuo and the product purified by chromatography on silica gel using ether as eluent.

TABLE 4

| | Starting Material | | | Product | | Phos. Salt Wt (g) | KO$^t$Bu Wt (g) | THF Total Vol (ml) | Time (hr) | Extraction Solvent | Yield Wt (g) | IR (Neat) cm$^{-1}$ |
|---|---|---|---|---|---|---|---|---|---|---|---|---|
| Prep No | Z | R | Wt (g) | R | R' | | | | | | | |
| 95 | (tetrahydropyranyl-O with phenyl-OCH$_2$CHCH$_2$-N(CH$_3$)- substituent) | O⟨⟩ | 2.27 | O⟨⟩ | H | 8.19 | 4.14 | 130 | 2 | Ethyl acetate | 2.2 | 3400, 1735 |
| 96 | (morpholine O⟨⟩N—) | —SiMe$_2^t$Bu | 18.9 | —SiMe$_2^t$Bu | H | 48.9 | 24.73 | 400 | 48 | Dichloromethane | 9.03 | 3505, 1740 |

TABLE 4-continued

[Structure: Starting material cyclopentane with OH, O-(tetrahydropyran), RO, Z substituents → Product cyclopentane with OR', RO, Z, and pentenyl-CO2CH3 chain]

| Prep No | Starting Material Z | R | Wt (g) | Product R | R' | Phos. Salt Wt (g) | KO'Bu Wt (g) | THF Total Vol (ml) | Time (hr) | Extraction Solvent | Yield Wt (g) | IR (Neat) cm⁻¹ |
|---|---|---|---|---|---|---|---|---|---|---|---|---|
| 97 | O⟨ ⟩N— (morpholinyl) | —SiMe₂ᵗBu | 18.9 | H | —SiMe₂ᵗBu | 48.9 | 24.73 | 400 | 48 | Dichloromethane | 5.16 | 3460, 1740 |
| 98 | ⟨ ⟩N— (piperidinyl) | O⟨ ⟩ (THP) | 10.63 | O⟨ ⟩ (THP) | H | 45.45 | 23 | 310 | 1.5 | Dichloromethane | 6 | 3540, 3480, 1742 |

PREPARATION 99

[1α(Z),2β,3α,5α]-(±)-7-[5-Acetoxy-2-(4-morpholinyl)-3-[(tetrahydro-2H-pyran-2-yl)oxy]cyclopentyl]-5-heptenoic acid, methyl ester 4-Carboxybutyltriphenyl phosphonium bromide (175.4 g) was added to potassium tert-butoxide (88.7 g) in dry tetrahydrofuran (500 ml). After 20 minutes the product of Preparation 73 (62 g) in dry tetrahydrofuran (200 ml) was added and stirring maintained for 4 hr. Water (100 ml) was added and the solvents were removed in vacuo. The residue was treated with ice/water (200 ml) and carefully adjusted to pH 7 by adding sodium bisulphate solution. The mixture was extracted with dichloromethane. The aqueous phase was brought to pH 6 using sodium bisulphite and re-extracted with dichloromethane. This process was repeated twice more. The combined extracts were treated with excess ethereal diazomethane dried, evaporated.

The residue was dissolved in acetic anhydride (200 ml) and pyridine (100 ml) and left at room temperature overnight. The solvents were removed in vacuo and the residue in dichloromethane was washed with 8% sodium bicarbonate solution. The organic layer was dried (MgSO₄) and evaporated. The residue was purified by chromatography on silica eluting with 9:1 ether-petroleum ether to give the title compound as a pale yellow oil (49.2 g).

T.L.C. Silica-ether Rf 0.36
I.R. (CHBr₃) 1725 cm⁻¹.

PREPARATION 100

[1α,(Z),2β,3α,5α]-(±)-7-[5-Hydroxy-2-(4-morpholinyl)-3-[(tetrahydro-2H-pyran-2-yl)oxy]cyclopentyl]-5-heptenoic acid, methyl ester To a solution of sodium methoxide (404 mg) in dry methanol (50 ml) was added a solution of the product of Preparation 99 (2.3 g) in dry methanol (50 ml). The mixture was allowed to stand at room temperature for 4 hr then poured into saturated ammonium chloride and rapidly extracted with dichloromethane (4×50 ml). The combined organic phases were washed with brine, dried and evaporated under reduced pressure to afford an oil. The product was subjected to column chromatography on silica gel. Eluting with 95:5 ether-methanol gave the title compound as an oil (1.83 g). IR (Neat) 3530, 3460, 1740 cm⁻¹.

PREPARATION 101

[1α(Z),2β,3α,5α]-(±)-7-[2-azido-3-hydroxy-5-(phenylmethoxy)cyclopentyl]-5-heptenoic acid, methyl ester 4-Carboxybutyl triphenyl phosphonium bromide (21.1 g) was added to a solution of potassium tert-butoxide (10.66 g) in dry tetrahydrofuran (300 ml) under dry nitrogen. The resultant deep orange suspension was stirred at room temperature for 30 min and then treated with a solution of the product of Preparation 60 Table 3 (6.0 g) in dry tetrahydrofuran (50 ml) over 1 min. A slight exothermic reaction was noted at this stage. The reaction mixture was diluted with water (300 ml) after 10 min and the resultant red solution extracted with ether (2×150 ml). The ether layers were extracted with 2 N sodium hydroxide (150 ml) and the combined aqueous phases acidified with concentrated hydrochloric acid. The resultant aqueous mixture was extracted with ether (4×150 ml) and the combined ether layers washed with brine (150 ml) and dried (MgSO₄). Removal of the solvent gave the crude acid which was dissolved in methanol (20 ml) and treated with ethereal diazomethane to yield the crude methyl ester as an oil (10.0 g). Purification by chromatography on silica using ether:petroleum ether (40°-60°) 1:1 as eluent gave the title compound as a pale yellow oil (3.0 g). I. R. (Neat) 3450, 2100, 1736 cm⁻¹.

PREPARATION 102

[1α(Z),2β,3α,5α]-(±)-7-[2-[1,1-Dimethylethoxy)carbonylamino]-5-(phenylmethoxy)-3-[(tetrahydro-2H-pyran-2-yl)oxy]cyclopentyl]-5-heptenoic acid, methyl ester 4-Carboxybutyltriphenylphosphonium bromide (2.58 g) was added to a solution of potassium tert-butoxide (1.3 g) in dry tetrahydrofuran (30 ml) under nitrogen and stirring continued for 20 mins. A solution of the product of Preparation 94 (0.84 g) in tetrahydrofuran (20 ml) was then added dropwise. After 40 min. the mixture was treated with saturated ammonium chloride solution until pH 6 and then extracted with dichloromethane (3×100 ml). The combined organic extracts were treated with ethereal diazomethane and then concentrated. The product was purified by column chromatography on silica gel using 3:2 ether-petroleum ether as eluent to give the title compound as a solid (0.59 g). m.p. 59°-61°.

PREPARATION 103

1-Azido-4-(bromomethyl)benzene

A mixture of p-azidotoluene (3.9 g), N-bromosuccinimide (5.5 g) and azobisisobutyronitrile (1.0 g) in carbon tetrachloride (30 ml) was heated under reflux in the dark under nitrogen for 18 h. The reaction mixture was allowed to cool to room temperature and the solvent was removed in vacuo. The residue was dissolved in ether (50 ml) and filtered. Evaporation of solvent gave an oil (6.5 g) which was chromatographed on silica gel (200 g, Merck 7734). Elution with petroleum ether (b.p.40°-60°) gave the title compound as an oil (2.37 g). I.R. (Neat) 2120 cm$^{-1}$.

PREPARATION 104

2-(4-Bromomethyl)phenyl-1,3-dioxolane

4-Bromomethyl benzaldehyde (1.0 g), ethylene glycol (0.42 ml) and p-toluenesulphonic acid (catalytic amount) in benzene (100 ml) were heated under reflux overnight. The mixture was poured into 8% sodium bicarbonate solution (200 ml) and extracted into ether (2×100 ml). The combined extracts were washed with sodium sulphite solution (200 ml), dried (MgSO$_4$), filtered and evaporated to afford a solid. Purification from ether-petroleum ether gave the title compound as yellow needles (0.767 g) m.p. 41°-42°.

PREPARATION 105

[1α(Z),2β,3α,5α]-(±)-7-[3-[(1,1-Dimethylethyl)dimethylsilyl]oxy-5-methoxymethoxy-2-(4-morpholinyl)cyclopentyl]-5-heptenoic acid, methyl ester The product of Preparation 96 (1.02 g) in N,N-di-isopropylethylamine (2 ml) was treated dropwise with chloromethylmethyl ether (0.29 ml) and stirred for 10 hr. The reaction mixture was quenched with aqueous sodium bicarbonate (30 ml) and extracted with ethyl acetate (2×30 ml). The combined organic extracts were washed with brine, dried (MgSO$_4$) and concentrated to afford a mobile liquid (1.06 g). The product purified by chromatography on silica eluting with 30% petroleum ether in ethyl acetate to give the title compound as a pale yellow oil (0.9 g).
I.R. (CHBr$_3$) 1730 cm$^{-1}$.

PREPARATION 106

[1α(Z),2α,3α,5α]-(±)-7-[3-[(1,1-Dimethylethyl)dimethylsilyl]oxy]-5-(2-methoxyethoxy)methoxy-2-(4-morpholinyl)cyclopentyl]-5-heptenoic acid, methyl ester The title compound (1.33 g) was prepared from the product of Preparation 96 (1.32 g) and methoxyethoxymethylchloride (1.02 ml) by the procedure described for Preparation 105. Chromatography on silica eluting with 4:1 ether-petroleum ether gave the title compound as a yellow oil. I.R. (CHBr$_3$) 1728 cm$^{-1}$.

PREPARATION 107

[1α(Z),2β,3α,5α]-(±)-7-[(2-[N-Methyl-N-(phenylmethyl)amino]-5-(phenylmethoxy)-3-[[tetrahydro-2H-pyran-2-yl]oxy]cyclopentyl]-5-heptenoic acid methyl ester Dry p-toluenesulphonic acid (0.95 g) was added to a cold (−10°) mixture of the product of Example 5, Table 5 (1.5 g) and dihydropyran (0.84 g) in dichloromethane (30 ml) which was then stirred for 3.5 h at −10°. A further quantity of dihydropyran (1 ml) was added and the mixture stirred for a further 0.5 h. It was then poured into 8% sodium bicarbonate (100 ml), extracted with dichloromethane (3×75 ml), dried (MgSO$_4$) and evaporated, affording a dark oil (3.5 g). Chromatography on silica gel using ether and petroleum ether (b.p. 40°-60°) 1:1 as eluent gave the title compound (1.73 g). I.R. (CHBr$_3$) 1725 cm$^{-1}$.

PREPARATION 108

(1α,2β,5α)-(±)-2-(Methylamino)-5-(phenylmethoxy)-3-](tetrahydro-2H-pyran-2-yl)oxy]cyclopentane heptanoic acid, methyl ester The product of Preparation 107 (0.9 g) in ethyl acetate (60 ml) was hydrogenated over pre-reduced 10% palladium on charcoal (150 mg) for 20 h. The catalyst and the solvent were removed and the residue was purified by chromatography on silica eluting with ether-methanol 1:2 to give the title compound as a viscous oil (0.348 g). I.R. (CHBr$_3$) 1728 cm$^{-1}$.

PREPARATION 109

[1α,2β,3α,5α]-(±)-2-[N-(2-Hydroxyethyl)-N-methylamino]-5-(phenyl-methoxy)-3-[(tetrahydro-2H-pyran-2-yl)oxy]cyclopentane heptanoic acid, methyl ester A solution of the product of Preparation 108 (2.85 g) in toluene (30 ml) was treated with ethylene oxide (25% in toluene, 70 ml). The mixture was heated (90°) in an autoclave overnight and evaporated under reduced pressure to afford an oil (3.5 g). Column chromatography on silica gel with methanol as eluent gave the title compound (2.5 g) as a colourless oil. I.R. (Neat) 3460, 1740 cm$^{-1}$.

PREPARATION 110

[1α,2β,3α,5α]-(±)-2-[N-(2-Chloroacetyloxyethyl)-N-methylamino]-5-(phenylmethoxy)-3-[[tetrahydro-2H-pyran-2-yl]oxy]cyclopentane heptanoic acid, methyl ester Chloroacetyl chloride (0.55 ml) was added to a cold (−10°) stirred solution of the product of Preparation 109 (2.25 g) and pyridine (1.11 ml) in dichloromethane (25 ml). After 45 min the mixture was poured into 8% sodium bicarbonate solution (100 ml) and extracted into dichloromethane (3×50 ml). The combined extracts were dried (MgSO$_4$), filtered and evaporated to afford an oil (3.05 g). Column chromatography on silica gel with 20% petroleum ether (40°-60°) in ether as eluent gave the title compound (2.03 g). I.R. (Neat) 1763, 1740 cm$^{-1}$.

PREPARATION 111

[1α,2β(2±),3α,5α]-(±)-2-[N-(2-Hydroxyheptyl)-N-methylamino]-5-(phenylmethoxy)-3-[[tetrahydro-2H-pyran-2-yl]oxy]cyclopentane heptanoic acid, methyl ester A mixture of the product of Preparation 108 (0.2 g) and 1,2-epoxy-heptane (0.153 g) in dry methanol (10 ml) was heated under reflux for 20 h. The solvent was evaporated to afford an oil. Column chromatography on silica eluting with petroleum ether:ether (2:3) gave the title compound as an oil (0.18 g). I.R. (Neat) 3470, 1745 cm$^{-1}$.

PREPARATION 112

[1α,2β(2±),3α,5α]-(±)-2-[N-(2-Chloroacetyloxyheptyl)-N-methylamino]-5-(phenylmethoxy)-3-[[tetrahydro-2H-pyran-2-yl]oxy]cyclopentane heptanoic acid, methyl ester.

Chloroacetyl chloride (0.63 ml) was added dropwise to a cold (−10°) solution of the product of Preparation 111 (3 g) and pyridine (1.26 g) in dry dichloromethane (30 ml). The mixture was stirred for 1.5 h then poured into 8% sodium bicarbonate soluton and extracted with dichloromethane (3×100 ml). The combined extracts were washed with sodium acetate solution (100 ml), dried (MgSO$_4$) and concentrated to afford a dark red oil. the product was purified by chromatography on silica. Elution with ether:petroleum 3:7 gave the title compound as a yellow oil (2.24 g). I.R. (Neat) 1760 (sh.) 1740 cm$^{-1}$.

PREPARATION 113

[1α(Z),2β,3α]-(±)-7-[[3-((1,1-Dimethylethyl)dimethylsilyl]oxy]-2-(4-morpholinyl)-5-oxocyclopentryl]-5-heptanoic acid, methyl ester.

To a stirred solution of the product of Preparation 97 (882 mg) and dicyclohexyl carbodiimide (1.648 g) in dimethylsulphoxide (20 ml) was added pyridinium trifluoroacetate (578 mg). Stirring was maintained for 1 h, the suspension poured into water (100 ml) and extracted into ether (3×50 ml). The combined ethereal layers were filtered (to remove dicyclohexyl urea), washed with water (2×50 ml), washed with brine (50 ml), dried (MgSO$_4$) and evaporated. The residual solid was triturated with ether/petroleum ether 40°-60° (25 ml, 1:1) and filtered. The filtrate was evaporated to afford the title compound as a colourless semi-solid (0.81 g). T.l.c. (Silica) Rf. 0.37 (ether).

PREPARATION 114

[1α(Z),2β,3α,5α]-(±)-7-[N-methyl-N-(2,2,2-trichloroethoxycarbonyl)amino]-5-(phenylmethoxy)-3-[(tetrahydro-2H-pyran-2-yl)oxy]cyclopentyl]-5-heptanoic acid, methyl ester The title compound (2.4 g) was prepared from the product of Preparation 107 (4.3 g) using the method described for Example 39. Chromatography on silica, eluting with etherpetroleum ether (1:1), gave the product as an oil. I.R. (Neat) 1735 (sh.), 1720 cm$^{-1}$.

PREPARATION 115

[1α(Z),2β,3α,5α]-(±)-7-[(2-Methylamino)-5-(phenylmethoxy)-3-[(tetrahydro-2H-pyran-2-yl)oxy]cyclopentyl]-5-heptanoic acid, methyl ester The title compound (3.2 g) was prepared from the product of Preparation 114 (10.0 g) using the method described for Example 40. Chromatography on silica, eluting with ethermethanol (4:1), gave the product as an oil, I.R. (Neat) 1738 cm$^{-1}$.

PREPARATION 116

[1α,(Z),2β,3α,5α]-(±)-7-[2-[N-Methyl-N-[2-(phenylmethoxy)ethyl]amino]-5-(phenylmethoxy)-3-[(tetrahydro-2H-pyran-2-yl)oxy]cyclopentyl]-5-heptenoic acid, methyl ester A mixture of the product of Preparation 115 (1 g), 2-(phenylmethoxy)-3 ethyl bromide (0.54 g), potassium carbonate (0.47 g) and sodium iodide (0.37 g) in acetonitrile (30 ml) was heated under reflux for 20 hr. The mixture was poured into saturated ammonium chloride solution and extracted with dichloromethane. The combined extracts were dried and evaporated to give the title compound as a brown oil (1.48 g). T.l.c. (Silica) Rf. 0.72 and 0.64 (ether-methanol, 9:1).

PREPARATION 117

[1α(Z),2β,3α,5α]-(±)-7-[2-[N-Methyl-N-(4-phenoxybutyl)amino]-5-(phenylmethoxy)-3-[(tetrahydro-2H-pyran-2-yl)oxy]cyclopentyl]-5-heptenoic acid, methyl ester The title compound (1.37 g) was prepared from the product of Preparation 115 (1 g) and 4-phenoxybutyl bromide (0.57 g) using the procedure described for Preparation 116. T.l.c. (Silica) Rf. 0.69 (ether-methanol, 9:1).

PREPARATION 118

[1α(Z),2β,3α,5α]-(±)-7-[2-[N-Methyl-N-(5-phenylpentyl)amino]-5-(phenylmethoxy)-3-[(tetrahydro-2H-pyran-2-yl)oxy]cyclopentyl]-5-heptenoic acid, methyl ester The title compound (1.5 g) was prepared from the product of Preparation 115 (1 g) and 5-phenylpentyl bromide (0.61 g) using the procedure described for Preparation 116. T.l.c. (Silica) Rf. 0.47 (ether-methanol, 95:5)

PREPARATION 119

(3aα,4α,6aα)-(±)-Tetrahydro-4-[N-methyl-N-[2-(tetrahydro-2H-pyran-2-yl)oxy]heptyl]amino]-2H-cyclopenta(b)furan-2-one The title compound (1.0 g) was prepared from the product of Preparation 76 (2.2 g) using the method of Preparation 107. Chromatography on silica, eluting with ether-petroleum ether (4:1), gave the product as an oil. I.R. (Neat) 1775 cm$^{-1}$.

PREPARATION 120

(3aα,4α,6aα)-(±)-Tetrahydro-4-[N-methyl-N-[2-[(tetrahydro-2H-pyran-2-yl)oxy]heptyl]amino]-2H-cyclopenta(b)furan-2-ol.

The title compound (2.1 g) was prepared from the product of Preparation 119 (2.1 g) in dry dichloromethane (50 ml) by the method of Preparation 47-66. I.R. (Neat) 3420 cm$^{-1}$.

PREPARATION 121

[1α(Z),2,3,5α]-(±)-7-[5-Hydroxy-2-[N-methyl-N-[2-[(tetrahydro-2H-pyran-2H-pyran-2-yl)oxy]heptylamino]-3-cyclopenten-1-yl]-5-heptenoic acid, methyl ester.

The title compound (10.83 g) was prepared from the product of Preparation 120 (18 g) using the procedure described for Examples 95-98 Table 4. Chromatography on silica, eluting with ether-petroleum ether (9:1), then ether, gave the product as an oil. I.R. (Neat) 3540, 1740 cm$^{-1}$.

EXAMPLES 1-15

(±)-7-(2,3,5-Trisubstituted)cyclopentyl-5-heptenoic acid, methyl esters

Table 5 summarises the preparation of the title compounds from 2-oxabicyclo [3,2,1]octan-3-ols by the method of Preparation 95-98. The reaction mixture was then worked up by one of the following methods:

A. The reaction mixture was treated with methanol followed by concentrated sulphuric acid until acidic and left to stir at room temperature for the time specified. After removal of solvents in vacuo the residue was basified by the addition of 8% aqueous sodium bicarbonate solution and/or solid sodium bicarbonate. Extraction with ethyl acetate, followed by washing of the combined extracts, drying and evaporation gave an oil. Purification was by chromatography on silica gel or alumina.

B. Isolation of the crude ester was as described in Method A. The resulting oil was treated with acetic anhydride and pyridine and stirred at room temperature for the time specified. The solvent was removed in vacuo and the product purified by chromatography on silica gel.

C. Ice was added to the reaction mixture followed by the careful addition of 2 N hydrochloric acid until neutral. The mixture was then poured into water, extracted with ethyl acetate, washed with brine, dried and concentrated. The crude material was dissolved in dichloromethane and treated with freshly distilled diazomethane in ether. The solution was concentrated and the product purified by chromatography on silica gel.

TABLE 5

Reaction scheme: Starting bicyclic phosphorus-containing compound → cyclopentane product with OR, OR substituents and side chain bearing CO₂CH₃.

| Ex. No. | Starting Material R | Starting Material Z | Wt (g) | Product R' | Phos. salt wt (g) | KO'Bu (Wt) (g) | THF Total vol. (ml) | Time hr | Method of work-up | MeOH Vol. (ml) | cH₂SO₄ Vol. (ml) | Time hr | Ac₂O Vol. (ml) | Py. Vol. (ml) | Time hr | Chromatography System | Yield (g) | I.R. (CHBr)₃ cm⁻¹ | Tlc (silica) Rf (solvent) |
|---|---|---|---|---|---|---|---|---|---|---|---|---|---|---|---|---|---|---|---|
| 1 | —CH₂—C₆H₅ | morpholine-N— | 5 | —COCH₃ | 28.53 | 14.04 | 170 | 20 | B | 300 | 20 | 72 | 120 | 50 | 3 | 9:1 ether-petroleum ether Silica | 3.1 | (Neat) 1736 | 0.46 ether |
| 2 | —CH₂—C₆H₅ | piperidine-N— | 10.9 | —COCH₃ | 21.06 | 10.65 | 250 | 3 | B | 300 | 25 | 18 | 50 | 50 | 16 | ether | 9.95 | 1750 (sh) 1720 | 0.57 ether |
| 3 | —CH₂—C₆H₅ | CH₃N-piperazine-N— | 1.8 | H | 6 | 3 | 40 | 1.5 | A | 150 | 20 | 16 | — | — | — | 94:6 ether-methanol (Alumina) | 1.05 | 3520, 1728 | 0.3 (94:6 ether-petroleum ether) (Alumina) |
| 4 | —CH₂—C₆H₅ | thiomorpholine-S,S-dioxide-N— | 3 | H | 7.3 | 3.68 | 175 | 2 | A | 150 | 25 | 90 | — | — | — | ethyl acetate | 3.11 | 3600, 1730 | 0.35 (ethyl acetate) |
| 5 | —CH₂—C₆H₅ | CH₃(CH₂C₆H₅)N— | 6.44 | H | 11.52 | 5.9 | 150 | 3 | A | 200 | 6 | 18 | — | — | — | ether | 5 | 3580 (sh), 3520, 1729 | 0.48 (ether) |
| 6 | —CH₃ | CH₃(CH₂C₆H₅)N— | 4.2 | H | 26.6 | 13.44 | 250 | 3 | A | 200 | 25 | 24 | — | — | — | ether | 3.7 | 3580-3500 1725 | 0.3 (ether) |

TABLE 5-continued

Starting Material → Product (scheme with bicyclic ether starting material giving cyclopentane diol with $CO_2CH_3$ side chain)

| Ex. No. | Starting Material Z | Starting Material R | Wt (g) | Product R' | Phos. salt wt (g) | KO'Bu (Wt) (g) | THF Total vol. (ml) | Time hr | Method of work-up | MeOH Vol. (ml) | cH$_2$SO$_4$ Vol. (ml) | Time hr | Ac$_2$O Vol. (ml) | Py. Vol. (ml) | Time hr | Chromatography System | Yield (g) | I.R. (CHBr$_3$) cm$^{-1}$ | Tlc (silica) Rf (solvent) |
|---|---|---|---|---|---|---|---|---|---|---|---|---|---|---|---|---|---|---|---|
| 7 | $CH_3$–N–$CH_2CH_2$–(phenyl) | —CH$_2$—(phenyl) | 2.3 | H | 11.16 | 5.62 | 120 | 2 | C | — | — | — | — | — | — | ether Silica | 1.42 | (Neat) 3540, 3450, 1733 | 0.3 (ether) |
| 8 | morpholine-N | —CH$_3$ | 5.03 | —COCH$_3$ | 37.6 | 18.54 | 300 | 3 | B | 300 | 20 | 18 | 30 | 30 | 18 | ether | 5.95 | | 0.63 (ether) |
| 9 | morpholine-N | —CH$_2$CH$_2$—(phenyl) | 2.57 | H | 7.98 | 4.04 | 120 | 3 | A | 100 | 15 | 18 | — | — | — | 97:3 ethyl acetate-methanol | 0.94 | 3540, 1728 | 0.37 (94:6 ether-methanol) |
| 10 | morpholine-N | —CH(CH$_3$)$_2$ | 5.2 | —COCH$_3$ | 17 | 8.6 | 130 | 1.2 | B | 100 | 20 | 18 | 24 | 40 | 3 | ether | 3.23 | 1725 | 0.39 (ether) |
| 11 | morpholine-N | —CH$_2$—(phenyl) | 6.3 | —COCH$_3$ | 16.8 | 8.5 | 210 | 3 | B | 200 | 40 | 18 | 50 | 100 | 3 | 3:2 ethyl acetate-petroleum ether | 5.65 | 1725 | 0.48 (3:2 ethyl acetate-petroleum ether) |
| 12 | azepane-N | —CH$_2$—(phenyl) | 2.8 | —COCH$_3$ | 9.5 | 4.74 | 80 | 1.5 | B | 100 | 10 | 20 | 25 | 50 | 3 | 3:2 ether-petroleum ether | 2.2 | 1723 | 0.74 (ether) |

TABLE 5-continued

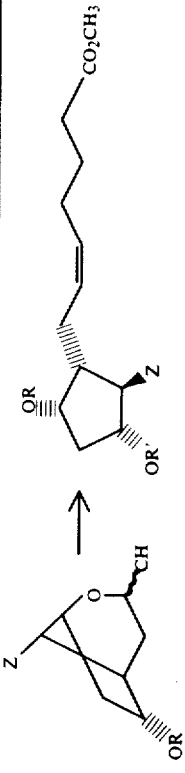

| Ex. No. | Starting Material Z | R | Wt (g) | Product R' | Phos. salt wt (g) | KO'Bu (Wt) (g) | THF Total vol. (ml) | Time hr | Method of work-up | MeOH Vol. (ml) | cH$_2$SO$_4$ Vol. (ml) | Time hr | Ac$_2$O Vol. (ml) | Py. Vol. (ml) | Time hr | Chromatography System Silica | Yield (g) | I.R. (CHBr$_3$) cm$^{-1}$ | Tlc (silica) Rf (solvent) |
|---|---|---|---|---|---|---|---|---|---|---|---|---|---|---|---|---|---|---|---|
| 13 | CH$_3$—⟨O⟩—CH$_3$ N— | —CH$_2$—Ph | 3.96 | H | 12.6 | 6.4 | 100 | 1 | A | 75 | 15 | 16 | — | — | — | 4:1 ether-petroleum ether | 1.97 | 3580, 3540, 1730 | 0.5 (95.5 ether-methanol) |
| 14 | ⟨N—⟩ | —CH(CH$_3$)$_2$ | 1.34 | H | 6.6 | 3.34 | 110 | 0.5 | A | 36 | 4 | 18 | — | — | — | 5:1 ether-methanol | 0.94 | 3520, 1728 | 0.44 (5:1 ether-methanol) |
| 15 | ⟨N—⟩ | —CH$_2$CH$_2$—Ph | 1.6 | H | 6.4 | 3.24 | 150 | 0.5 | A | 36 | 4 | 18 | — | — | — | 5:1 ether-methanol | 1.03 | 2540, 1730 | 0.55 (5:1 ether-methanol) |

EXAMPLES 16-19

Deacetylation of 7-(3 or 5-acetoxy-2,5 or 2,3-disubstituted cyclopentyl)-5-heptenoic acid, methyl esters Table 6 summarises the deacetylation of the title compounds by the following method.

To a solution of the appropriate acetate in methanol at room temperature was added either sodium methoxide or potassium carbonate. The mixture was stirred for the time specified then poured into saturated ammonium chloride solution and extracted with dichloromethane. The combined extracts were dried ($MgSO_4$), filtered and concentrated, and the product purified by short path column chromatography on silica gel.

Analysis Found: C, 62.1; H, 9.3; N, 4.2; $C_{17}H_{29}NO_5$ requires: C, 62.4; H, 8.9; N, 4.3%.

EXAMPLE 21

[1α(E),2β,3α,5α]-(±)-7-[3-Hydroxy-2-(4-morpholinyl)-5-(phenylmethoxy)cyclopentyl]-5-heptenoic acid, methyl ester A solution of the product of Example 16 (2.5 g), thiophenol (7.5 ml) and azobisisobutyronitrile (1.5 g) in benzene (10 ml) was heated at 70° for 6 hr. The reaction mixture was applied directly to a silica gel column and eluted with diethyl ether to remove the thiophenol. Elution with 30% methanol in diethyl ether gave the crude trans ester (2.46 g). The product was further subjected to column chromatography on silica gel whereupon elution with 3% methanol in ether gave the title compound as an oil (1.48 g). IR (Neat) 3450, 1730 $cm^{-1}$.

Analysis Found: C, 68.4; H, 8.3; N, 3.3; $C_{24}H_{35}NO_5$ requires: C, 69.0; H, 8.5; N, 3.4%.

TABLE 6

| Ex. No. | Starting Material Z | Starting Material R | Wt (g) | MeOH Vol. (ml) | NaOMe Wt (g) | $K_2CO_3$ Wt (g) | Time (hr) | Chromatography System | Yield (g) | IR ($CHBr_3$) $cm^{-1}$ | Tlc silica Rf (solvent) |
|---|---|---|---|---|---|---|---|---|---|---|---|
| 16 | morpholinyl | $-CH_2-C_6H_5$ | 19.52 | 200 | 3.4 | — | 3 | 93:7 ether-methanol | 15.68 | 3520, 1725 | 0.63 (9:1 ethyl acetate-methanol) |
| 17 | morpholinyl | $-CH_3$ | 4.7 | 10 | 0.66 | — | 4.5 | acetone | 3.95 | 3520, 1725 | 0.11 (ether) |
| 18 | morpholinyl | $-CH(CH_3)_2$ | 6.8 | 140 | — | 3.42 | 4 | 95:5 ether-methanol | 5.2 | (Neat) 3450, 1730 | 0.45 (95:5 ether-methanol) |
| 19 | hexamethyleneimino | $-CH_2-C_6H_5$ | 2.1 | 40 | 0.72 | — | 5 | 95:5 ether-methanol | 1.2 | 3600, 3500, 1725 | 0.43 (95:5 ether-methanol) |

EXAMPLE 20

[1α(Z),2β,3α,5α]-(±)-7-[3,5-Dihydroxy-2-(4-morpholinyl)cyclopentyl]-5-heptenoic acid, methyl ester The product of Preparation 72 (2.3 g) was treated with (4-carboxybutyl) triphenyl phosphonium bromide (17.7 g) according to the method of Preparations 95-98. The reaction mixture was then worked up as follows:

The reaction mixture was treated with methanol (100 ml) followed by saturated ethereal HCl (75 ml) and the suspension allowed to stand at 5° for 2 days. Water was added and the mixture carefully made alkaline by the addition of solid $NaHCO_3$. Extraction with ethyl acetate, followed by washing of the combined extracts drying and evaporation gave an oil which was purified by chromatography on silica gel, using 85:15 ethyl acetate-methanol as eluent, to yield the title compound (1.82 g), IR (Neat) 3420, 1735 $cm^{-1}$.

EXAMPLE 22

[1α(Z),2β,3α,5α]-(±)-7-[5-Acetoxy-3-hydroxy-2-(4-morpholinyl)cyclopentyl]-5-heptenoic acid, methyl ester A solution of the product from Preparation 99 (2.51 g) in acetone (100 ml) containing 2 N hydrochloric acid (25 ml) was allowed to stand at room temperature for 5 hr. The mixture was poured into 8% aqueous sodium bicarbonate (200 ml) and extracted into dichloromethane (4×50 ml). The combined extracts were washed with brine, dried and evaporated under reduced pressure. The residue was purified by column chromatography on silica gel eluting with 3% methanol in ether to give the title compound as an oil (1.95 g). IR (Neat) 3450, 1738 cm$^{-1}$.

Analysis Found: C, 62.09; H, 8.93; N, 3.76; $C_{19}H_{31}NO_6$ requires: C, 61.76; H, 8.46; N, 3.79%.

EXAMPLE 23

[1α(Z),2β,3α,5α]-(±)-7-[3-Hydroxy-5-(phenylmethoxy)-2-(1-piperidinyl)cyclopentyl]-5-heptenoic acid, methyl ester Sodium methoxide (0.889 g) was added to the product of Example 2 (7.56 g) in dry methanol (25 ml) at −10°. The reaction mixture was stirred at room temperature for 20 hr. Sodium methoxide (0.889 g) was added and the stirring continued for a further 6 hr. The mixture was poured into 8% aqueous sodium bicarbonate solution (100 ml) and water (50 ml) and extracted with ether (3×135 ml). The dried organic layers were evaporated in vacuo. Silica gel chromatography on the residue with acetone as eluent gave the title compound as an oil (5.1 g) IR (Neat) 3500, 3440, 1738 cm$^{-1}$.

Analysis Found: C, 71.83; H, 8.82; N, 3.41; $C_{25}H_{37}NO_4$ requires: C, 72.25; H, 8.98; N, 3.37%.

EXAMPLE 24

[1α(Z),2β,3α,5α]-(±)-7-[3-Acetoxy-2-(N-benzyl-N-methylamino)-5-methoxy-cyclopentyl]-5-hetpenoic acid, methyl ester The product of Example 6 (25.25 g) was dissolved in a mixture of dry pyridine (20 ml) and $Az_2O$ (20 ml) and the resultant solution allowed to stand at room temperature for 18 hr. Removal of the solvent in vacuo and chromatography of the residue on silica gel using ether as eluent gave the title compound as an oil (5.7 g), IR (Neat) 1737 cm$^{-1}$.

Analysis Found: C, 69.07; H, 8.38; N, 3.30; $C_{24}H_{35}NO_5$ requires: C, 69.03; H, 8.45; N, 3.35%.

EXAMPLE 25

[1α(Z),2β,3α,5α]-(±)-7-[3-Hydroxy-2-[N-methyl-N-2-phenylethyl)amino]-5-(phenylmethoxy)cyclopentyl]-5-heptenoic acid, monohydrate The product from Example 7 (1.0 g) was dissolved in a solution of potassium hydroxide (360 mg) and methanol (30 ml) and the solution allowed to stand at room temperature for 2 days. The methanol was then removed in vacuo and the residue dissolved in water (20 ml). The resultant solution was neutralised carefully with 2 N hydrochloric acid and then extracted with ethyl acetate (3×40 ml). The combined organic phases were washed with brine (20 ml), dried and the solvent removed to yield a viscous oil. Chromatography on silica gel using 4:1 ethyl acetate-methanol as eluent gave the title compound as an oil (513 mg). IR (Neat) 1720 cm$^{-1}$.

Analysis Found: C, 71.94; H, 8.57; N, 2.87; $C_{28}H_{37}NO_4H_2O$ requires: C, 71.61; H, 8.37; N, 2.98%.

EXAMPLE 26

[1α(Z),2β,3α,5α]-(±)-7-[3,5-Dihydroxy-2-[N-methyl-N-(2-hydroxy-3-phenoxy-propyl)amino]cyclopentyl]-5-heptenoic acid, methyl ester 2 N Hydrochloric acid (15 ml) was added dropwise to a solution of the product of Preparation 95 (2.01 g) in acetone (15 ml) at room temperature. After 20 mins the solution was neutralised with aqueous sodium bicarbonate, diluted with brine, extracted with ethyl acetate, dried and concentrated to give a viscous liquid. The crude material was purified by column chromatography on silica gel eluting with 5% methanol in ether to yield the title compound as a viscous oil (0.81 g), IR (Neat) 3400, 1736 cm$^{-1}$.

Analysis Found: C, 65.41; H, 8.87; N, 3.32; $C_{23}H_{35}NO_6$ requires: C, 65.53; H, 8.37; N, 3.32%.

EXAMPLE 27

[1α(Z),2β,5α]-(±)-7-[5-Hydroxy-2-[N-(2-hydroxyheptyl)-N-methylamino]-3-cyclopenten-1-yl]-5-heptenoic acid, methyl ester Dry (4-carboxybutyl) triphenyl phosphonium bromide (8.4 g) was added to a stirred solution of potassium tertbutoxide (4.23 g) in dry tetrahydrofuran (50 ml) at room temperature under nitrogen and stirring continued for 30 mins. A solution of the product of Preparation 77 (1.7 g) in dry tetrahydrofuran (20 ml) was added dropwise and stirring continued at room temperature for 30 mins. The reaction mixture was treated with methanol (150 ml) followed by concentrated sulphuric acid until acidic and then stirred at room temperature for 18 hr. The mixture was concentrated in vacuo and the residue treated with water (100 ml) and extracted into ether (3×50 ml). The acidic aqueous layer was basified with 8% aqueous sodium bicarbonate solution and extracted with ethyl acetate (3×60 ml). The combined organic extracts were dried, filtered and evaporated.

The crude product was treated with acetic anhydride (10 ml) and left to stand at ambient temperature for 18 hr. Evaporation in vacuo gave a residue which was chromatographed on silica gel using ether as eluent. The diacetate, isolated as an oil (1.6 g), was dissolved in dry methanol (25 ml) and treated with anhydrous potassium carbonate (1 g). After stirring for 18 hr. at room temperature the reaction mixture was diluted with water (50 ml) and extracted with ether (3×50 ml). The combined extracts were washed, dried and evaporated and the residue was chromatographed on silica gel. Elution with 9:1 ether-methanol gave the title compound as an oil (1.13 g). IR (Neat) 3420, 1740 cm$^{-1}$.

Analysis Found: C, 68.37; H, 10.27; N, 3.82; $C_{21}H_{37}NO_4$ requires: C, 68.63; H, 10.15; N, 3.81%.

EXAMPLE 28

[1α(Z),2β,3α,5α]-(±)-7-[2-Amino-3-hydroxy-5-(phenylmethoxy)cyclopentyl]-5-heptenoic acid, methyl ester (a) The product of Preparation 101 (1 g) in tetrahydrofuran (10 ml) was treated sequentially with zinc dust (2.0 g) and 1 M potassium dihydrogen phosphate (2.0 ml) and the resultant slurry stirred rapidly for 1 hr. A second aliquot of 1 M potassium dihydrogen phosphate (2.0 ml) was then added and the reaction stirred for a further 2 hr and then filtered. The filtrate was diluted with ether (25 ml) and extracted with 2 N hydrochloric acid (3×15 ml). The combined acidic layers were washed with ether (20 ml) and then basified with concentrated ammonia solution at 0°. The resultant basic solution was extracted with dichloromethane (3×20 ml) and the combined organic phases washed with brine (2×15 ml) and dried (MgSO$_4$). Removal of the solvent gave the product as a colourless oil (300 mg). IR (CHBr$_3$) 3680, 3500, 1728 cm$^{-1}$.

Analysis Found: C, 68.4; H, 9.0; N, 4.2 $C_{20}H_{31}NO_4$ requires: C, 68.7; H, 8.9; N, 4.0%.

(b) Trifluoro acetic acid (1 ml) was added dropwise to the product of Preparation 102 (0.323 g) stirred at −5°. After 10 min. the mixture was treated with 8% sodium bicarbonate solution until pH 7, followed by extracted with dichloromethane (2×50 ml). The combined organic extracts were washed (8% NaHCO₃), dried (MgSO₄) and concentrated. The product was purified by chromatography on silica gel using 1:1 ether-petroleum ether as eluent to give the title compound as a viscous oil (0.122 g).

EXAMPLE 29

[1α(Z),2β,3α,5α]-(±)-7-[2-(Hexahydro-1,4-oxazepin-4-yl)-3-hydroxy-5-(phenylmethoxy) cyclopentyl]-5-heptenoic acid, methyl ester The product of Example 28 (1.0 g), 1-chloro-3-(2-chloroethoxy) propane (452 mg) and sodium bicarbonate (484 mg) in dry methanol (5 ml) were heated in an autoclave at 125° for 18 hr. The mixture was filtered and the solvent removed in vacuo to give an oil (1.44 g), which was chromatographed on slica. Elution with methanol/ether 1:9 gave the title compound as a straw coloured oil (400 mg).

Analysis Found: C, 69.7; H, 8.4; N, 3.45; $C_{25}H_{37}NO_5$ requires: C, 69.6; H, 8.6; N, 3.25%.

IR (CHBr₃) 3550, 1730 cm⁻¹.

EXAMPLE 30

[1α(Z),2β,3α,5α]-(±)-7-[3-Hydroxy-2-(4-morpholinyl)-5-(phenylmethoxy) cyclopentyl]-5-heptenoic acid To a stirred solution of potassium hydroxide (1.25 g) in methanol (10 ml) was added a solution of the product of Example 16 (766 mg) in methanol (10 mg). The resultant solution was stirred for 1 hr. then allowed to stand overnight. The solvent was removed by evaporation under reduced pressure and the residue dissolved in water (7 ml). Hydrochloric acid (5 N) was added until the solution attained pH7. The solution was extracted with dichloromethane (5×10 ml). The combined organic extracts were washed with brine, dried (sodium sulfate) and evaporated under reduced pressure to afford a foam (625 mg). The product was subjected to short path column chromatography on silica gel (50 g). Eluting with 12% methanol in ether gave the title compound as a glass (383 mg). IR (CHBr₃) 3600, 1720 cm⁻¹.

Analysis Found: C, 67.8; H, 8.3; N, 3.2; $C_{23}H_{33}NO_5$ requires: C, 68.5; H, 8.2; N, 3.5%.

EXAMPLE 31

[1α(Z),2β,3α, 5α]-(±)-7-[1-(4-Butyl-4-hydroxy) piperidinyl]-3-hydroxy-5-(phenylmethoxy)cyclopentyl]-5-heptenoic acid, methyl ester, hydrochloride The title compound base (0.98 g) was prepared from the product of Preparation 61 (Table 3) (1.65 g) by the method described for Examples 1–15, Table 5. A sample of the base was dissolved in ether and treated with ethereal hydrogen chloride. The resulting oil was purified from ethyl acetate to give the title compound as a white solid m.p. 132°–132.5°.

Analysis Found: C, 66.3; H, 9.1; N, 2.7; $C_{29}H_{45}NO_5$ HCl requires: C, 66.45; H, 8.85; N, 2.7%.

EXAMPLE 32

[1α(Z),2β,3α,5α]-(±)-7-[5-Hydroxy-2-[N-methyl-N-(phenylmethyl)amino]-3-cyclopentenyl]-5-heptenoic acid, methyl ester The title compound (8.0 g) was prepared from the product of Preparation 88 (10.2 g) by the method described for Examples 1–15 (Method A). The reaction mixture was chromatographed on silica eluting with ether. A portion was subjected to molecular distillation b.p. 148° at 0.05 mm Hg.

Analysis Found: C, 73.05; H, 8.6; N, 4.1; $C_{21}H_{29}NO_3$ requires: C, 73.4; H, 8.5; N, 4.1%.

EXAMPLE 33

[1α(Z),2α,5β]-(±)-7-[2-Hydroxy-5-(4-morpholinyl)-3-cyclopenten-1-yl]-5-heptenoic acid, methyl ester The title compound (4.55 g) was prepared from the product of Preparation 81 (4.6 g) by the method described for Examples 1–15. Method A. The reaction mixture was chromatographed on silica eluting initially with ethyl acetate and then 9:1 ethyl acetate-methanol m.p. 37°–40°.

Analysis Found: C, 66.6; H, 9.0; N, 4.6; $C_{17}H_{27}NO_4$ requires: C, 66.0; H, 8.8; N, 4.5%.

EXAMPLE 34

[1α(Z), 2β,3α,5α]-(±)-7-[3-[[(1.1'-Biphenyl)-4-yl]methoxy]-5-hydroxy-2-(4-morpholinyl)cyclopentyl]-5-heptenoic acid, methyl ester The title compound (1.04 g) was prepared from the product of Preparation 85 (1.16 g) by the method described for Examples 1–15, Method A. The reaction mixture was chromatographed on silica eluting with ethyl acetate. A portion was purified from ether as needles m.p. 91°–91.5°.

Analysis Found: C, 73.25; H, 8.05; N, 2.8; $C_{30}H_{39}NO_5$ requires: C, 73.0; H, 8.0; N, 2.85%.

EXAMPLE 35

[1α(Z),2α,5β]-(±)-7-[2-Hydroxy-5-(4-morpholinyl)cyclopentyl]-5-heptenoic acid, methyl ester, hydrochloride The title compound base was prepared from the product of Preparation 83 (2.13 g) by the method described for Examples 1–15, Method A. After removal of the solvents in vacuo the residue in water (150 ml) was extracted with ethyl acetate (2×100 ml). The combined organic extracts were back-extracted with 2 N sulphuric acid. The combined acidic aqueous layers were basified with solid sodium bicarbonate and extracted with ethyl acetate (3×100 ml). The combined organic extracts were dried and evaporated to give an oil which was purified by chromatography on silica, eluting initially with ethyl acetate and then 19:1 ethyl acetatemethanol (2.06 g). A portion (800 mg) was converted into the hydrochloride salt (800 mg) which was purified from methanol-ethyl acetate to give the title compound (695 mg) m.p. 141°–143°.

Analysis Found: C, 58.55; H, 9.1; N, 4.0; $C_{17}H_{29}NO_4$ HCl requires: C, 58.7; H, 8.7; N, 4.0%

EXAMPLE 36

[1α(Z),2β,3α,5α]-(±)-7-[3,5-Dihydroxy-2-[N-methyl-N-(2-phenylethyl)amino]cyclopentyl]-5-heptenoic acid, methyl ester The title compound (385 mg) was prepared from the product of Preparation 58 (Table 3) (1.2 g) by the method of Preparations 95–98. The reaction mixture was treated with methanolic hydrogen chloride (50 ml) and the resultant suspension stirred for 19 hr. at ambient temperature. The methanolic mixture was neutralised with 8% sodium bicarbonate solution and treated with ethyl acetate (100 ml) and brine (100 ml). The phases were separated and the aqueous solution extracted with ethyl acetate (2×50 ml). The combined organic extracts were washed with brine (100 ml), dried (MgSO$_4$) and the solvent removed to yield an oil (6.25 g). Chromatography on silica eluting with methanolethyl acetate 3:17 gave the title compound as a pale yellow oil.

Analysis Found: C, 70.3; H, 8.7; N, 3.7; $C_{22}H_{33}NO_4$ requires: C, 70.4; H, 8.6; N, 3.7%.

IR(CHBr$_3$) 3590, 3530, 1725 cm$^{-1}$.

EXAMPLE 37

[1α(Z),2β,3α,5α]-(±)-7-[3-Hydroxy-2-[N-methyl-N-(2-hydroxy-3-phenoxypropyl)amino]-5-(phenylmethoxy)-cyclopentyl]-5-heptenoic acid, methyl ester The product of Preparation 59 (Table 3) (2.6 g) was subjected to a Wittig reaction as described for Preparations 95–98 (Table 4).

2 N Hydrochloric acid (10 ml) was added to a solution of the product (2.17 g) in acetone (15 ml) at room temperature. After 3 hr. the solution was neutralised with aqueous sodium bicarbonate, extracted with ether, dried (Na$_2$SO$_4$) and concentrated to give a gum (2.1 g). The crude material was purified by chromatography on silica gel eluting with 4% methanol in either to yield the title compound a pale yellow viscous oil (1.07 g). IR CHBr$_3$) 3590, 1725 cm$^{-1}$.

Analysis Found: C, 70.07; H, 8.27; N, 2.63; $C_{30}H_{41}NO_6$ requires: C, 70.42; H, 8.08; N, 2.74%.

EXAMPLE 38

[1α(Z),2β,3α,5α]-(±)-7-[3-Acetoxy-2-[N-methyl-N-(phenylmethyl)amino]-5-(phenylmethoxy)cyclopentyl]-5-heptenoic acid, methyl ester The product of Example 5 (Table 5) (8.04 g) was treated with acetic anhydride (35 ml) and pyridine (35 ml). The resulting solution was stirred for 24 hr. at ambient temperature. The solvent was removed to yield an oil. This crude product was chromatographed on silica gel (500 g) with ether as eluent giving the title compound as a yellow oil (7.01 g). Distillation at 180°/0.1 mm Hg gave the title compound. IR (CHBr$_3$) 1723 cm$^{-1}$.

EXAMPLE 39

[1α(Z),2β,3α,5α]-(±)-7-[3-Acetoxy-2-[N-methyl-N-(2,2,2-trichloroethoxycarbonyl)amino]-5-(phenylmethoxy)cyclopentyl]-5-heptenoic acid, methyl ester The product of Example 38 (6.2 g) was added to trichloroethylchloroformate (2.2 ml). The reaction mixture was heated with stirring at 90° for 1.25 hr. after which time potassium carbonate (2.5 g) was added and the stirring continued for a further 1 hr. The excess trichloroethylchloroformate was removed by distillation (80°/1 mm Hg). The product was diluted with ether (50 ml) and filtered. Removal of the solvent gave the crude product which was chromatographed on silica gel (850 g) with ether-petroleum ether 2:1 as eluent. The product was recovered as a yellow oil (6.47 g). Distillation at 170°/0.05 mm Hg gave the title compound. IR (Neat) 1733, 1718 cm$^{-1}$.

EXAMPLE 40

[1α(Z),2β,3α,5α]-(±)-7-[3-Acetoxy-2-(methylamino)-5-(phenyl-methoxy)cyclopentyl]-5-heptenoic acid, methyl ester Potassium dihydrogen phosphate solution (1 M, 30 ml) was added dropwise to a cold (0°) stirred mixture of the product of Example 39 (4.0 g) and activated zinc dust (15.0 g) in tetrahydrofuran (50 ml). The mixture was stirred at room temperature for 7 hr. then poured into 8% sodium bicarbonate solution (400 ml), filtered and extracted into ethyl acetate (3×200 ml). The combined extracts were dried (MgSO$_4$), filtered and evaporated to afford an oil (2.7 g). Chromatography on silica gel (50 g) with 20% methanol in ether as the eluent gave the title compound (2.05 g). IR (CHBr$_3$) 1725 cm$^{-1}$.

Analysis Found: C, 68.2; H, 8.3; N, 3.5; $C_{23}H_{33}NO_5$ requires: C, 68.5; H, 8.2; N, 3.5%.

EXAMPLE 41

[1α(Z),2β,3α,5α]-(±)-7-[3-Hydroxy-2-(methylamino)-5-(phenylmethoxy)cyclopentyl]-5-heptenoic acid, methyl ester Potassium carbonate (1.74 g) was added to a stirred solution of the product of Example 40 (4.24 g) in dry methanol (50 ml). The mixture was stirred for 4.5 hr., poured into ammonium chloride solution (125 ml) and extracted dichloromethane (3×60 ml). The combined extracts were dried (MgSO$_4$), filtered and evaporated to afford the title compound as a viscous oil (4.0 g). IR (CHBr$_3$) 3680, 3510, 1730 cm$^{-1}$. Tlc (Silica) R$_{71}$ 0.16 (4:1 Ether-methanol).

EXAMPLE 42

[1α(Z),2β,3α,5α]-(±)-7-[2-N-Heptyl-N-methylamino)-3-hydroxy-5-(phenylmethoxy)cyclopentyl]-5-heptenoic acid, methyl ester A mixture of bromoheptane (0.605 g), potassium carbonate (0.627 g), sodium iodide (0.55 g) and the product of Example 41 (1.1 g) in acetonitrile (55 ml) was heated under reflux for 24 hr. The suspension was diluted with ethyl acetate (50 ml), filtered and evaporated to afford a viscous oil (1.73 g). Chromatography on silica gel (50 g) with 10% methanol in ether as the eluent gave the title compound (0.73 g).

IR (CHBr$_3$) 3540, 1730 cm$^{-1}$.

Analysis Found: C, 73.3; H, 10.0; N, 3.1; $C_{28}H_{45}NO_4$ requires: C, 73.2; H, 9.9; N, 3.1%.

EXAMPLE 43

[1α(Z),2β,3α,5α]-(±)-7-[2-N-(2-butoxyethyl)-N-methylamino]-3-hydroxy-5-(phenylmethoxy)cyclopentyl]-5-heptenoic acid, methyl ester A mixture of 2-bromoethylbutyl ether (0.48 g), potassium carbonate (0.5 g), sodium iodide (0.4 g) and the product of Example 41 (0.87 g) in acetonitrile (30 ml) was heated under reflux for 20 hr. The mixture was poured into a saturated solution of ammonium chloride (75 ml) and extracted into dichloromethane (3×50 ml).

The combined extracts were dried (MgSO$_4$), filtered and evaporated to afford a viscous oil (1.2 g). Chromatography on silica gel with 1:9 methanol-ether as the eluent gave the title compound (0.74 g).

IR (CHBr$_3$) 3540–3360, 1730 cm$^{-1}$.

Analysis Found: C, 70.0; H, 9.8; N, 3.2; C$_{27}$H$_{43}$NO$_5$ requires: C, 70.2; H, 9.4; N, 3.0%.

EXAMPLE 44

[1α(E),2β,3α,5α]-(±)-7-[3-Hydroxy-5-(phenylmethoxy)-2-(1-piperidinyl)cyclopentyl]-5-heptenoic acid, methyl ester A solution of thiophenol (2 ml), azobisisobutyronitrile (0.4 g) and the product of Example 23 (1.27 g) in benzene (6 ml) was maintained at 65° for 4 hr. The benzene was removed and the product was isolated directly by chromatography on silica eluting firstly with ether and then with acetone containing triethylamine (1%). The crude product was purified by chromatography on slica eluting with acetone containing triethylamine (1%) to give the title compound as a yellow oil (0.9 g).

IR (CHBr$_3$) 3520, 1724 cm$^{-1}$.

Analysis Found: C, 71.9; H, 9.3; N, 3.4; C$_{25}$H$_{37}$NO$_4$ requires: C, 72.2; H, 9.0; N, 3.35%.

EXAMPLE 45

[1α(Z),2β,3α,5α]-(±)-7-[3-Acetoxy-2-(4-morpholinyl)-5-(1-phenylethoxy)cyclopentyl]-5-heptenoic acid, methyl ester To a stirred solution of potassium t-butoxide (4.0 g) in dry tetrahydrofuran (50 ml) under nitrogen was added 4-carboxybutyl triphenyl phosphonium bromide (7.98 g). The dark red suspension was stirred for 30 min. whereupon a solution of the product of Preparation 56, Table 3 (2 g) in dry tetrahydrofuran (20 ml) was added. After 2 hr. excess ethereal hydrogen chloride (100 ml) was added and the mixture evaporated under reduced pressure (finally at 2 mm). The residue was dissolved in dichloromethane (200 ml) and treated with excess ethereal diazomethane. Acetic acid was added cautiously to decompose unreacted diazoalkane. The solution was washed with 8% sodium bicarbonate (100 ml) and the phases separated. The aqueous layer was washed with dichloromethane (150 ml). The combined organic extracts were dried (MgSO$_4$) and evaporated. The residue was taken up in acetic anhydride (25 ml) and pyridine (50 ml), left over night and then evaporated in vacuo (2 mm). The crude product was treated with 8% sodium bicarbonate (100 ml) and extracted into dichloromethane (4×75 ml). The combined organic layers were dried (MgSO$_4$) and evaporated. The residual oil was purified by chromatography on silica. Eluting with ether/petroleum ether 4:1 gave the title compound as a colourless oil (2.34 g). IR (CHBr$_3$) 1726 cm$^{-1}$.

Analysis Found: C, 68.1; H, 8.3; N, 3.0; C$_{27}$H$_{39}$NO$_6$ requires: C, 68.5; H, 8.3; N, 3.0%.

EXAMPLE 46

[1α(Z),2β,3α,5α]-(±)-7-[3-Hydroxy-2-(4-morpholinyl)-5-(1-phenylethoxy)cyclopentyl]-5-heptenoic acid, methyl ester To a stirred solution of the product of Example 45 (2.2 g) in anhydrous methanol (25 ml) was added dry potassium carbonate (770 mg). After 4 h the suspension was poured into saturated ammonium chloride (100 ml) and extracted with dichloromethane (4×50 ml). The combined extracts were dried (MgSO$_4$) and evaporated. The residual oil was purified by chromatography on silica. Eluting with 4% methanol in ether gave the title compound (1.6 g) as a straw coloured oil.

Analysis Found: C, 69.0; H, 8.5; N, 3.2; C$_{25}$H$_{37}$NO$_5$ requires: C, 69.6; H, 8.6; N, 3.3%.

I.R.(CHBr$_3$) 3520, 1730 cm$^{-1}$.

EXAMPLE 47

[1α(Z),2β,3α,5α]-(±)-7-[2-(2,6-trans-Dimethyl-4-morpholinyl)-3-hydroxy-5-(phenylmethoxy)cyclopentyl]-5-heptenoic acid, methyl ester The title compound was isolated from the experiment described in Example 13 Table 5. Chromatography of the crude reaction product on silica as described gave the title compound as a brown oil (135 mg).

I.R. (CHBr$_3$) 3540, 1730 cm$^{-1}$

Tlc (Silica) R$_f$0.59 (95:5 Ether-methanol)

EXAMPLE 48–73

7-(3-Hydroxy-2,5-disubstituted)cyclopentyl-5-heptenoic acid, methyl ester

Tables 7–9 summarise the preparation of the title compounds from 7-(5-hydroxy-2,3-disubstituted)-cyclopentyl-5-heptenoic acid, methyl esters by the following methods:

A. Without characterisation of the 7-(2,3,5-trisubstituted)cyclopentyl-5-heptenoic acid, methyl esters 1. To a cold (0°) stirred solution of the appropriate alcohol and halide* in dry dimethylformamide under nitrogen was added sodium hydride (80%) dispersion in oil). After ½–2 h the mixture was poured into saturated ammonium chloride solution and extracted with ether. The combined extracts were dried, filtered and evaporated. The residual oil was dissolved in methanol and conc. sulphuric acid carefully added. The solution was allowed to stand for 1 h at room temperature, poured into 8% sodium bicarbonate solution and extracted into ether. The combined ethereal layers were washed with brine, dried (over MgSO$_4$) and concentrated. The product was purified by short path column chromatography on silica gel.

2. The procedure is essentially as described under A1 except that the crude reaction mixture is poured into methanol and conc. sulphuric acid carefully added.

3. The procedure is essentially as described under A.2 except that 5 N HCl is used instead of c. H$_2$SO$_4$.

4. The procedure is essentially as described under A.1 except that methanolic HCl is used.

B. With isolation of the 7-(2,3,5-trisubstituted)cyclopentyl-5-heptenoic acid, methyl ester To a cold (0°) stirred solutation of the appropriate alcohol and halide* in dry dimethylformamide under nitrogen was added either sodium hydride (80% dispersion in oil) or potassium tert-butoxide. After 1 h at 0°and 0.5–1.5 h at room temperature the mixture was poured into saturated ammonium chloride solution and extracted with ether. The combined extracts were dried, filtered and evaporated. The residual oil was purified by column chromatography on silica gel.

C. Deprotection of the 7-(2,3,5-trisubstituted)cyclopentyl-5-heptenoic acid, methyl esters The prostanoids are then deprotected by one of the following methods:

1. A solution of the prostanoid in methanol at room temperature was treated with ethereal HCl. After 0.5 h the solvent was removed in vacuo and the residue dissolved in dichloromethane and washed with 8% aqueous sodium bicarbonate solution. The combined organic extracts were dried, filtered and concentrated. The residue was purified by column chromatography on silica gel.

2. A solution of the prostanoid in methanol at room temperature was treated with methanolic sulphuric acid. After 0.5–1 h the solution was poured into 8% aqueous sodium bicarbonate solution with the remaining work-up as described in procedure C.I.

TABLE 7
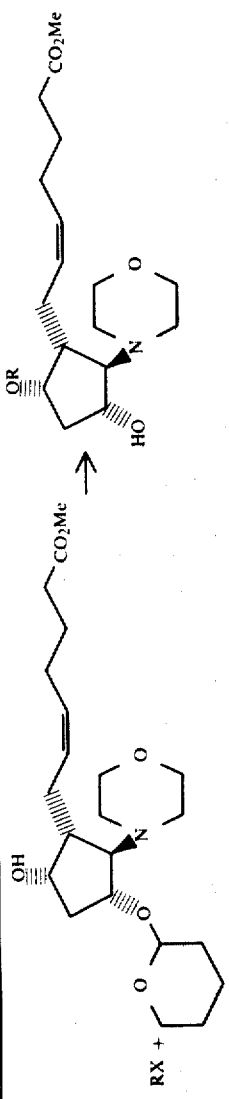
| Ex. No. | Alcohol Wt (g) | Halide R | Halide X | Halide Wt (g) | Method | DMF Total Vol. (ml) | NaH Wt (g) | MeOH Vol. (ml) | CH₂SO₄ Vol. (ml) | Chromatography System (ether-methanol) | Yield (g) | I.R. (CHBr₃) cm⁻¹ | Tlc (silica) Rf (solvent)** |
|---|---|---|---|---|---|---|---|---|---|---|---|---|---|
| 48 | 2.46 | —CH₂—C₆H₄—Br | Br* | 4.49 | A3 | 55 | 0.9 | 100 | 100 (5NHCl) | 96:4 | 1.10 | 1725 | 0.27 |
| 49 | 1.64 | —CH₂—C₆H₄—CH₃ | Br | 5.92 | A2 | 15 | 0.72 | 100 | 10 | 96:4 | 0.87 | 3540, 1728 | 0.27 |
| 50 | 2.5 | —CH₂—C₆H₄—CH(OCH₂CH₂O) | Br | 5.9 | A1 | 30 | 0.73 | 67.5 | 7.5 | 95:5 | 2.0 | 3590–3520, 1730, 1700 | 0.23 |
| 51 | 2.47 | —CH₂—C₆H₄—O(CH₂)₃CH₃ | Br | 5.83 | A1 | 20 | 0.72 | 22.5 | 2.5 | 97:3 | 1.6 | 3530, 1728 | 0.37 |
| 52 | 0.5 | —CH₂—C₆H₄—Ph | Br | 0.3 | A1 | 7 | 0.146 | 13.5 | 1.5 | 97:3 | 0.175 | 1730 | 0.37 |
| 53 | 2.47 | —CH₂—C₆H₄—OPh | Br | 6.31 | A1 | 20 | 0.72 | 22.5 | 2.5 | 97:3 | 1.69 | 3540, 1728 | 0.35 |
| 54 | 2.47 | —CH₂—C₆H₄—PhO (ortho) | Br | 6.31 | A1 | 20 | 0.72 | 22.5 | 2.5 | 97:3 | 1.61 | 3530, 1730 | 0.42 |

TABLE 7-continued

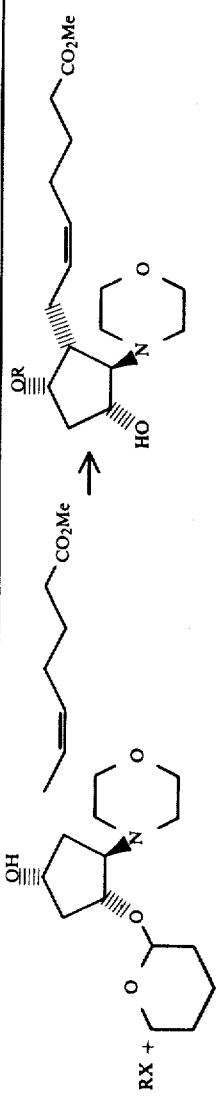

| Ex. No. | Alcohol Wt (g) | Halide R | Halide X | Halide Wt (g) | Method | DMF Total Vol. (ml) | NaH Wt (g) | MeOH Vol. (ml) | CH₂SO₄ Vol. (ml) | Chromatography System (ether-methanol) | Yield (g) | I.R. (CHBr₃) cm⁻¹ | Tlc (silica) Rf (solvent)** |
|---|---|---|---|---|---|---|---|---|---|---|---|---|---|
| 55 | 2.47 | —CH₂-(3,5-diCH₃-C₆H₃) | Br | 4.8 | A1 | 20 | 0.72 | 22.5 | 2.5 | 97:3 | 1.66 | 3540(br), 1730 | 0.36 |
| 56 | 2.47 | —CH₂-(4-OPh-C₆H₄) | Br | 6.31 | A1 | 20 | 0.72 | 22.5 | 2.5 | 97:3 | 1.55 | 3570, 3540, 1728 | 0.31 |
| 57 | 2.46 | —(CH₂)₄CH₃ | I | 5.91 | A4 | 20 | 0.72 | 20 | — | 95:5 | 0.91 | 3520, 1730 | 0.36 |
| 58 | 2.46 | —CH₂-(4-CF₃-C₆H₄) | Br | 3.84 | A1 | 20 | 0.72 | 30 | 1.5 | 95:5 | 1.87 | 3600, 3540, 1730 | 0.33 |
| 59 | 2.47 | —CH₂-(2-Ph-C₆H₄) | Br | 5.93 | A1 | 20 | 0.72 | 22.5 | 2.5 | 97:3 | 0.97 | 3590–3500, 1730 | 0.46 |

*Sodium iodide (2.7 g) was first added to the bromide in D.M.F.

The isolated product is the aldehyde R = CH₂—C₆H₄—CHO

**Rf values were determined in the solvent system used for column chromatography

TABLE 8

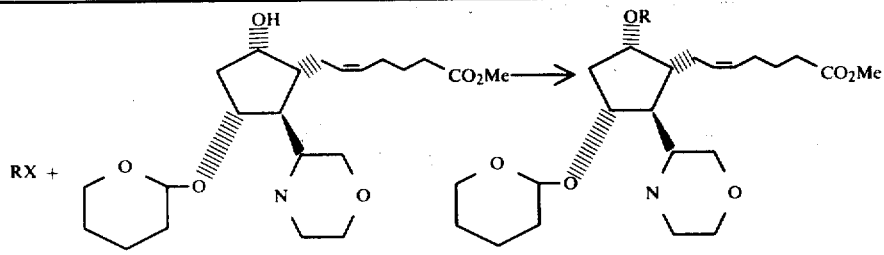

RX +

| Ex. No. | Alcohol Wt. (g) | Halide R | X | Wt (g) | NaY Wt (g) | DMF Total Vol. (ml) | NaH Wt (g) | Chromatography System | Yield (g) | I.R. (CHBr₃) | Tlc (Silica) Rf (ether) |
|---|---|---|---|---|---|---|---|---|---|---|---|
| 60 | 2.47 | —CH₂—⌬—OCH₃ | CL | 5.61 | Y = Br 3.72 | 25 | 0.9 | 1:1 ether-petroleum ether | 2.01 | 1730 | 0.52 |
| 61 | 2.2 | —CH₂—⌬—CN | Br | 7.84 | — | 20 | 0.9 | 9:1 ether-methanol | 1.2 | 2250, 1730 | 0.35 |
| 62 | 2.46 | —CH₂—⌬—OCH₂PL | CL | 5.6 | Y = I 3.6 | 30 | 0.72 | Ether | 2.0 | 1730 | 0.39 |
| 63 | 2.46 | —CH₂—⌬—OCH₃ (meta) | Br | 4.82 | — | 30 | 0.72 | Ether | 2.2 | 1730 | 0.39 |
| 64 | 2.46 | —CH₂—⌬—Cl,Cl | CL | 5.87 | Y = I 4.5 | 30 | 1 | Ether | 3.0 | 1730 | 0.36 |
| 65 | 2.46 | —CH₂—CH=CH₂ | Br | 2.9 | — | 20 | 0.72 | Ether | 2.1 | 1740 | 0.33 |
| 66 | 2.46 | —CH₂CH₂CH₂PL | I | 5.9 | — | 20 | 0.72 | Ether | 1.12 | 1740 | 0.38 |

TABLE 9

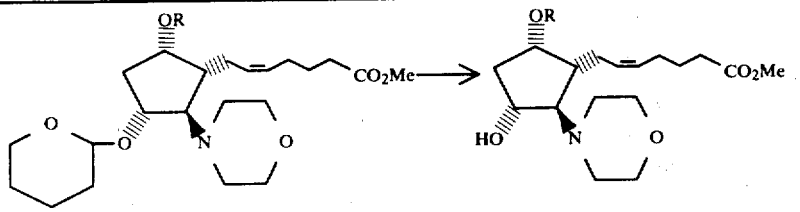

| Ex. No. | 21 Starting Material R | Wt (g) | Method | MeOH Vol. (ml) | Ether/HCl Vol. (ml) | CH₂SO₄ Vol. (ml) | Chromatography System (ether-methanol) | Yield (g) | I.R. (CHBr₃) cm⁻¹ | Tlc silica Rf 5% methanol in ether |
|---|---|---|---|---|---|---|---|---|---|---|
| 67 | —CH₂—⌬—OCH₃ | 2.6 | C2 | 50 | — | 5 | 95:5 | 1.27 | 3450, 1730 | 0.26 |

TABLE 9-continued

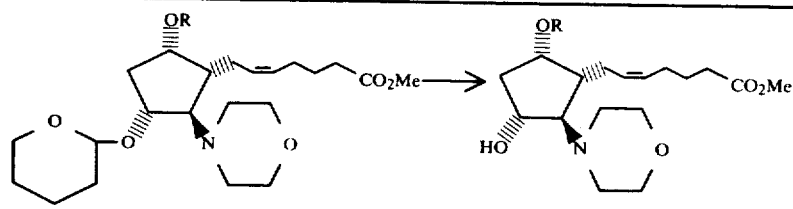

| Ex. No. | 21 Starting Material R | Wt (g) | Method | MeOH Vol. (ml) | Ether/ HCl Vol. (ml) | CH$_2$SO$_4$ Vol. (ml) | Chromatography System (ether-methanol) | Yield (g) | I.R. (CHBr$_3$) cm$^{-1}$ | Tlc silica Rf 5% methanol in ether |
|---|---|---|---|---|---|---|---|---|---|---|
| 68 | —CH$_2$—C$_6$H$_4$—CN | 2.1 | C2 | 50 | — | 5 | 94:6 | 1.53 | 3500, 2250, 1730 | 0.35 |
| 69 | —CH$_2$—C$_6$H$_4$—OCH$_2$Ph | 2.0 | C2 | 95 | — | 5 | 96:4 | 0.84 | 3520, 1725 | 0.35 |
| 70 | —CH$_2$—C$_6$H$_4$—OCH$_3$ | 2.2 | C2 | 95 | — | 5 | 96:4 | 1.25 | 3530, 1728 | 0.32 |
| 71 | —CH$_2$—C$_6$H$_3$Cl$_2$ | 3.0 | C2 | 95 | — | 5 | 96:4 | 1.76 | 3540, 1728 | 0.3 |
| 72 | —CH$_2$—CH=CH$_2$ | 2.1 | C1 | 15 | 15 | — | 95:5 | 1.27 | 3540, 1728 | 0.26 |
| 73 | —CH$_2$CH$_2$CH$_2$—C$_6$H$_5$ | 1.1 | C1 | 15 | 15 | — | 95:5 | 0.7 | 3520, 1728 | 0.31 |

EXAMPLE 74

[1α(Z),2β,3α,5α]-(±)-7-[4-(Aminothioxomethyl)phenylmethoxy]-3-hydroxy-2-(4-morpholinyl)cyclopentyl]-5-heptenoic acid, methyl ester Dry tetrahydrofuran (10 ml) was added dropwise to a stirred mixture of sodium borohydride (0.623 g) and sulphur (1.56 g). After 20 min the product of Example 68 (1.8 g) in dry tetrahydrofuran (5 ml) was added. The mixture was heated under reflux with stirring for 4.5 h then poured into water (250 ml) and extracted into dichloromethane (3×100 ml). The combined extracts were dried (MgSO$_4$) and evaporated to afford an oil (2.8 g). Column chromatography on silica gel with 10% methanol in ether as the eluent gave the title compound as a yellow oil (1.02 g). I.R. (CHBr$_3$) 3580, 3490, 3375, 1730, 1600 cm$^{-1}$.

Analysis Found: C, 62.3; H, 7.9; N, 5.8; C$_{25}$H$_{36}$N$_2$SO$_5$ requires: C, 62.9; H, 7.6; N, 5.9%.

EXAMPLE 75

[1α(Z),2β,3α,5α]-(±)-7-[5-[4-Aminocarbonyl(phenylmethoxy)]-3-hydroxy-2-(4-morpholinyl)cyclopentyl]-5-heptenoic acid, methyl ester A mixture of the product of Example 68 (1.0 g), potassium hydroxide (1.0 g) and tertiary butanol (20 ml) was heated under reflux for 45 min. The mixture was treated with excess methanolic hydrogen chloride at room temperature for 4 h then evaporated. The residue was neutralised with 8% sodium bicarbonate solution and extracted into dichloromethane (3×50 ml). The combined extracts were dried (MgSO$_4$) and filtered and evaporated to afford the title compound (0.9 g). I.R. (CHBr$_3$) 3530, 3410, 1730, 1675, 1620 cm$^{-1}$.

Analysis Found: C, 64.7; H, 8.2; N, 5.6; C$_{25}$H$_{36}$N$_2$O$_6$ requires: C, 65.2; H, 7.9; N, 6.1%.

EXAMPLE 76

[1α(Z),2β,3α,5α]-(±)-7-[5-[[1,1'-Biphenyl)-4-yl]-3-hydroxy-2-(4-morpholinyl)cyclopentyl]-5-heptenoic acid, methyl ester, hydrochloride To a cold (0°) solution of the product of Preparation 100 (3 g) and biphenyl methyl bromide (5.41 g) in dry dimethylformamide (15 ml) was added potassium tertiary butoxide (2.65 g). The cooling bath was removed and the solution stirred for 2 hr during which time a fine white suspension developed. The mixture was poured into saturated ammonium chloride (100 ml) and extracted with ether (4×75 ml). The combined organic extracts were washed successively with water (100 ml) and brine (100 ml), dried (MgSO$_4$) and evaporated. The residue was purified by chromatography on silica eluting with ether to give the product as an oil (2.91 g). The oil was dissolved in 5% sulphuric acid in MeOH (100 ml) and was allowed to stand at room temperature for 1 hr. The solution was poured into 8% sodium bicarbonate (200 ml) and extracted with dichloromethane (4×75 ml). The combined extracts were dried (MgSO$_4$) and evaporated. The residue (2.4 g) was purified by chromatography on silica eluting with 5% methanol in ether to give the title compound base as an oil (1.72 g).

A portion of the product (0.6 g) in ether (20 ml) was treated with an excess of ethereal hydrogen chloride. The oily product was purified from ethyl acetatemethanol to give the title compound as fine platelets (0.47 g) m.p. 127°-128°.

Analysis Found C, 67.7; H, 7.6; N, 2.7. C$_{30}$H$_{39}$NO$_5$.HCl requires C, 68.0; H, 7.6; N, 2.6%.

EXAMPLE 77

[1α(Z),2β,3α,5α]-(±)-7-[5-[[(1,1'-Biphenyl)-4-yl]-3-hydroxy-2-(4-morpholinyl)cyclopentyl]-5-heptenoic acid, hydrochloride To a solution of the product of Example 76 in methanol (30 ml) was added aqueous potassium hydroxide solution (340 mg. in 10 ml). The mixture was allowed to stand at room temperature for 7 hr then evaporated in vacuo (0.5 mm). The residual oil was treated with water (20 ml), carefully acidified (to pH 7) with 2 M sodium bisulphite and extracted with dichloromethane (2×30 ml). The pH of the aqueous layer was adjusted to pH 6 by dropwise addition of bisulphite. Several extractions with dichloromethane (4×50 ml) were made during this operation. The combined organic layers were dried (MgSO$_4$) and evaporated to afford a pale pink foam (2.2 g). A small sample (ca. 200 mg) was taken up in dichloromethane (5 ml) and treated with excess ethereal hydrogen chloride. The solvent was removed and the oily residue was purified from isopropanol-petroleum ether to give the title compound m.p. 122°-124°.

Analysis Found C, 67.0; H, 7.3; N, 2.6 C$_{29}$H$_{37}$NO$_5$.HCl requires C, 67.5; H, 7.4; N, 2.7%.

EXAMPLE 78

[1α(Z),2β,3α,5α]-(±)-7-[5-(4-Cyclohexylohenylmethoxy)-3-hydroxy-2-(4-morpholinyl)cyclopentyl]-5-heptenoic acid, methyl ester p-Chlorohexylbenzyl chloride (4.99 g) was added to a solution of sodium iodide (4.2 g) in analar acetone (50 ml). The mixture was stirred for 4 hr at room temperature and then evaporated under reduced pressure. The residue was treated with ether (100 ml) and filtrate was washed with brine (50 ml), dried (MgSO$_4$) and evaporated to afford an orange oil. This iodide was contaminated with some (10%) of the ortho isomer.

The above benzyl iodide in dry dimethylformamide (20 ml) was added to a cold (−20°) solution of the product of Preparation 100 (2.45 g) in dry dimethylformamide (<10 ml). Sodium hydride (900 mg, 80% dispersion) was introduced, the cooling bath removed and stirring was continued for 1½ hr. The mixture was poured into saturated ammonium chloride (100 ml) and extracted with ether (4×70 ml). The combined organic extracts were washed with water (100 ml) and brine (100 ml), dried (MgSO$_4$) and evaporated. The residue oil was immediately purified by chromatography on silica. Eluting with ether gave a mixture (2.56 g) of two closely running components.

T.L.C. Rf0.46 and 0.51, silica/ether.

The mixture (2.5 g) was dissolved in 5% sulphuric acid in methanol (100 ml) and allowed to stand at room temperature for 1 hr. The solution was poured into 8% sodium bicarbonate (150 ml) and extracted with dichloromethane (3×75 ml). The combined extracts were dried (MgSO$_4$) and evaporated to afford an oil (2.1 g). The product was purified by chromatography on silica, eluting with 95:5 ether-methanol gave the title compound as a colourless oil (1.17 g) I.R. (CHBr$_3$) 3520 (br.), 1728 cm$^{-1}$.

Analysis found C, 71.9; H, 9.4; N, 3.0; C$_{30}$H$_{45}$NO$_5$ requires C, 72.1; H, 8.1; N, 2.8%.

EXAMPLE 79

[1α(Z),2β,3α,5α]-(±)-7-[5-(2-Cyclohexylphenylmethoxy)-3-hydroxy-2-(4-morpholinyl)cyclopentyl]-5-heptenoic acid, Methyl ester The title compound (0.18 g) was also isolated during the experiment described in Example 78. I.R. (CHBr$_3$) 3520(br), 1728 cm$^{-1}$.

Analysis Found: C, 72.0; H, 9.4; N, 2.7; C$_{30}$H$_{45}$NO$_5$ requires C, 72.1; H, 9.1; N, 2.8%.

EXAMPLE 80

[1α(Z),2β,3α,5α]-(±)-7-[5(4-Cyclohexylphenylmethoxy)-3-hydroxy-2-(4-morpholinyl)cyclopentyl]-5-heptenoic acid, hydrochloride The product of Example 78 (2 g) in methanol (15 ml) was added to aqueous potassium hydroxide solution (5 ml, 0.008016 mole). The mixture was stirred overnight then evaporated in vacuo. The residue was treated with water (25 ml) and the pH adjusted to pH 6–6.5 with 2 M sodium bisulphate solution. The suspension was extracted with dichloromethane (5×50 ml). The combined extracts were dried (MgSO$_4$) and evaporated to give an off-white foam (1.89 g).

A small portion (ca. 200 mg) was taken up in ether (5 ml) and treated with excess ethereal hydrogen chloride. The oily product was triturated with fresh ether to give the title compound m.p. 162°-163°.

Analysis found: C, 66.5; H, 8.4; N, 2.6; C$_{29}$H$_{43}$NO$_5$HCl requires C, 66.7; H, 8.4; N, 2.7%.

EXAMPLE 81

[1α(Z),2β,3α,5α]-(±)-7-[5-[4-Dimethylamino(phenylmethoxy]-3-hydroxy-2-(4-morpholinyl)cyclopentyl]-5-heptenoic acid, methyl ester To a stirred, cold (10°) solution of Preparation 100 (2.46 g) and p-dimethylaminobenzyl chloride hydrochloride (8.65 g) in dry dimethylformamide (30 ml) was added portionwise sodium hydride (1.8 g, 80% dispersion in oil). After 30 mins the suspension was poured into saturated ammonium chloride (250 ml) and extracted with ether (4×400 ml). The combined extracts were washed with water (2×100 ml) followed by brine (100 ml), dried (MgSO$_4$) and evaporated to afford a brown oil.

The above reaction was repeated twice more and the combined products were chromatographed on silica gel. Eluting with ether: petroleum ether (9:1) gave the product (920 mg) as a colourless oil.

A solution of the oil (900 mg) in 5% methanolic sulphuric acid (30 ml) was allowed to stand at room temperature for 30 mins. The solution was poured into 8% sodium bicarbonate (100 ml) and extracted with dichloromethane (3×50 ml). The combined extracts were dried (MgSO$_4$) and evaporated to afford an oil (870 mg). The product was purified by chromatography on silica, elution with ether:methanol (96:4) gave the title compound (541 mg) as a colourless oil. I.R. (Neat) 3440(br.), 1735 cm$^{-1}$.

Analysis found C, 67.7; H, 8.7; N, 6.3; C$_{26}$H$_{40}$N$_2$O$_5$ requires C, 67.8; H, 8.8; N, 6.1%.

EXAMPLE 82

[1α(Z),2β,3α,5α]-(±)-7-[5-[4-Azido(phenylmethoxy)]-3-hydroxy-2-(4-morpholinyl)cyclopentyl]-5-heptenoic acid, methyl ester A solution of the product of Preparation 100 (2.5 g) and p-azido benzyl bromide (5.16 g) in dry dimethylformamide (16 ml) was treated with sodium hydride (0.73 g., 80% dispersion in oil) under nitrogen and the mixture was stirred at room temperature for 2 hr.

Ammonium chloride solution (20 ml) was added with cooling and the mixture extracted with dichloromethane (3×20 ml). The combined organic layers were washed with water (50 ml) then dried (MgSO$_4$). Solvent removal in vacuo afforded an oil which was chromatographed on silica. Elution with ethyl acetate-petroleum ether (3:1) gave the product as an oil (2.2 g). A sample of the oil (0.45 g) was treated with sulphuric acid/methanol 1:9 (3 ml) at 0° and stirred at room temperature for 30 mins. The reaction mixture was poured into sodium bicarbonate (10 ml) and was extracted with dichloromethane (3×15 ml). The combined organic layers were washed with water (20 ml), brine (20 ml), and dried (MgSO$_4$). Solvent removal in vacue yielded a light brown oil (360 mg) which was chromatographed on silica. Elution with methanol/ether 1:9 gave the title compound as a light brown oil (0.22 g). I.R. (CHBr$_3$) 3540(br.), 2110, 2060 (sh), 1730 cm$^{-1}$.

Analysis Found: C, 62.7; H, 7.4; N, 12.0 C$_{24}$H$_{34}$N$_4$O$_5$ requires C, 62.9; H, 7.4; N, 12.2%.

EXAMPLE 83

[1α(Z),2β,3α,5α]-(±)-7-[5-[4-(1,1-Dimethylethyl)-phenylmethoxy]-3-hydroxy-2-(4-morpholinyl)-5-heptenoic acid, methyl ester Sodium hydride (0.15 g, 80% dispersion in oil) was added to a cold (0°) stirred solution of the product of Preparation 100 (0.5 g) and p-tertbutylbenzylbromide (0.28 g) in dry dimethylformamide (7 ml). After 2 hr the suspension was poured into saturated ammonium chloride solution (75 ml) and extracted into ether (3×50 ml). The combined extracts were dried (MgSO$_4$) filtered and evaporated to afford an oil (0.9 g). The product was treated with a 10% conc. sulphuric acid in methanol solution (15 ml) and left standing for 10 min. The solution was neutralised with 8% sodium bicarbonate and extracted into dichloromethane (3×30 ml). The combined extracts were dried (MgSO$_4$), filtered and evaporated to afford a yellow oil (1.0 g). Chromatography on silica with 7% methanol in ether as eluent gave the title compound as a colourless oil (0.302 g).

I.R. (CHBr$_3$) 3540, 1730 cm$^{-1}$.

Analysis Found: C, 70.8; H, 9.4; N, 2.9. C$_{28}$H$_{43}$NO$_5$ requires C, 71.0; H, 9.2; N, 3.0%.

EXAMPLE 84

[1α(Z),2β,3α,5α]-(±)-7-[3-Hydroxy-2-(4-morpholinyl)-5-phenoxycyclopentyl]-5-heptenoic acid, methyl ester To a cold solution (0°) if the product of Preparation 100 (1 g) in dry dimethylformamide (10 mls) was added NaH (292 mg, 80% dispersion in oil). After 5 mins diphenyliodonium chloride (1.54 g) was added, the cooling bath removed and stirring continued for a further 30 mins. A further quantity of diphenyliodonium chloride (1.54 g) was added after 45 mins, the mixture was poured into saturated ammonium chloride (50 mls) and extracted with ether (5×50 mls). The combined organic extracts were washed successively with water (100 mls) and brine (100 mls), dried (MgSO$_4$) was evaporated. The residue was purified by chromatography on silica and eluting with ether gave the product (170 mg).

The above experiment was repeated to give a further 150 mgs of the product.

The intermediate (320 mg) in 10% methanolic sulphuric acid (5 ml) was allowed to stand at room temperature for 30 mins. The solution was poured into saturated bicarbonate (50 mls) and extracted with dichloromethane (5×30 mls). The combined extracts were dried (MgSO$_4$) and evaporated. The residue (310 mg) was purified by chromatography on silica. Eluting with 3% methanol in ether gave the title compound (220 mg) as a colourless oil.

I.R. (CHBr$_3$) 3590, 1730 cm$^{-1}$

Tlc (Silica) Rf 0.29 (97:3 Ether-methanol)

EXAMPLE 85

[1α(Z),2β,3α,5α]-(±)-7-[5-(Diphenylmethoxy)-3-hydroxy-2-(4-morpholinyl)cyclopentyl]-5-heptenoic acid, methyl ester, hydrochloride salt A solution of the product of Preparation 100 (4.0 g) and diphenyl diazomethane (6.5 g) in acetonitrile was heated at 85° for 5 h. The solvent was removed under reduced pressure to give a semi-solid. The residue was dissolved in 5% methanolic sulphuric acid (100 ml) and left at room temperature for 1 h. The solution was poured into 8% sodium bicarbonate (200 ml) and extracted into dichloromethane (4×100 ml). The combined extracts were dried (MgSO$_4$) and evaporated and the residue purified by column chromatography on silica gel (Merck 7734, 180 g). Eluting first with ether and then with 95:5 ether-methanol gave the product as an oil (3.81 g). A sample (500 mg) was dissolved in ether (25 ml) and treated with excess ethereal hydrogen chloride. The title compound crystallised from ethyl acetatemethanol as colourless platelets, m.p. 174°-175°.

Analysis Found: C, 67.6; H, 7.7; N, 2.7; C$_{30}$H$_{39}$NO$_5$HCl requires C, 68.0; H, 7.6; N, 2.6%.

EXAMPLE 86

[1α(Z),2β,3α,5α]-(±)-7-[5-[4-(Dimethylaminomethyl)-phenylmethoxy]-3-hydroxy-2-(4-morpholinyl)cyclopentyl]-5-heptenoic acid, methyl ester To a solution of the product of Example 50 (0.6 g) in methanol (5 ml) was added ethanolic dimethylamine (33% w/w, 1.45 ml) followed by hydrochloric acid (5 N, 0.81 ml) and sodium cyanoborohydride (0.48 g). The resultant mixture was stirred for 3 days then poured into 8% sodium bicarbonate solution (100 ml) and extracted into ether (2×100 ml). The combined extracts were dried (MgSO$_4$), filtered and evaporated to afford a viscous oil (0.9 g). Short path column chromatography on silica gel (25 g) with methanol as the eluent gave the title compound as a colourless oil (0.396 g).

Analysis Found: C, 68.2; H, 9.0; N, 5.8; $C_{27}H_{42}N_2O_5$ requires: C, 68.3; H, 8.9; N, 5.9%.

I.R. (CHBr$_3$) 3540 (br), 1733 cm$^{-1}$

EXAMPLE 87

[1α(Z),2β,3α,5α]-(±)-7-;8 3-Hydroxy-5-methoxymethoxy-2-(4-morpholinyl)cyclopentyl]-5-heptenoic acid, methyl ester Tetrabutyl ammonium fluoride (0.86 g) was added to a solution of the product of Preparation 105 (0.8 g) in dry tetrahydrofuran (20 ml) and the reaction stirred at 45° for 3 hr. The mixture was quenched with aqueous sodium bicarbonate (50 ml) and extracted with dichloromethane (3×40 ml). The combined organic extracts were washed with brine, dried (MgSO$_4$) and concentrated to afford an oil (0.8 g). The product was purified by chromatography on silica eluting with 4% methanol in ether to yield title compound as a colourless oil (0.41 g).

I.R. (Neat) 3440, 1738 cm$^{-1}$

T.L.C. (Silica) Rf 0.18 (95:5 ether-methanol)

EXAMPLE 88

[1α(Z),2β,3α,5α]-(±)-7-[3-Hydroxy-5-(2-methoxyethoxy)methoxy-2-(4-morpholinyl)cyclopentyl]-5-heptenoic acid, methyl ester The title compound (0.85 g) was prepared from the product of Preparation 106 (1.53 g) by the procedure described for Example 87. Chromatography on silica eluting with 93:7 ether-methanol gave the title compound as a yellow oil.

I.R. (Neat) 3450, 1735 cm$^{-1}$.

Analysis Found C, 60.4; H, 9.3; N, 3.3. $C_{21}H_{37}NO_7$ requires C, 60.7; H, 9.0; N, 3.4%.

EXAMPLE 89

[1α(Z),2β,5α]-(±)-7-[4-Morpholinyl)-5-[[(1.1'-biphenyl)-4-yl]methoxy]cyclopentyl]-5-heptenoic acid, methyl ester, hydrochloride The product of Example 35 (1.35 g) was alklated with biphenyl methyl bromide (3.6 g) as described for Examples 48–59. The title compound was purified from ethyl acetate-ether (520 mg)(m.p. 99°–100°).

Analysis Found: C, 70.2; H, 8.2; N, 2.7; $C_{30}H_{39}NO_4$·HCl requires: C, 70.1; H, 7.8; N, 2.7%.

EXAMPLE 90

[1α(Z),2β,5α]-(±)-7-[2-(4-Morpholinyl)-5-(phenylmethoxy)cyclopentyl]-5-heptenoic acid, methyl ester, hydrochloride The product of Example 35 (2.6 g) was alkylated with phenyl methyl bromide (5.7 g) as described for Examples 48–59. The title compound was purified from ethyl acetate-light petroleum (500 g) m.p. 94°–96°.

Analysis Found: C, 65.9; H, 8.4; N, 3.2; $C_{24}H_{35}NO_4$·HCl requires: C, 65.8; H, 8.3; N, 3.2%.

EXAMPLE 91

[1α(Z),2β,5β]-(±)-7-[5-(4-Morpholinyl)-2-(phenylmethoxy)-3-cyclopentenyl-yl]-5-heptenoic acid, methyl ester A solution of the product of Example 33 (1.42 g) in dry dimethylformamide (22 ml) containing benzyl bromide (3.15 g) was stirred at 0° whilst potassium tertiary butoxide (1.03 g) was added. The cooling bath was removed after ca. 5 min and the reaction mixture was stirred at room temperature for 1 h. The reaction mixture was poured into an excess of ammonium chloride solution and extracted with ethyl acetate. The combined extracts were dried (MgSO$_4$) and evaporated to give an oil which was filtered through a short silica column in ether to remove the excess of benzyl bromide. The residual oil (1.2 g) was chromatographed on silica in ethyl acetate to give the title compound as a colourless oil (0.43 g). I.R. (CHBr$_3$) 1723 cm$^{-1}$ Analysis Found: C, 72.1; H, 8.4; N, 3.6; $C_{24}H_{33}NO_4$ requires: C, 72.15 H, 8.3; N, 3.5%.

EXAMPLE 92

[1α(Z),2β,3α,5α]-(±)-7-[5-[[(1,1'-Biphenyl)-4-yl]methoxy]-3-hydroxy-2-(1-piperidinyl)cyclopentyl]-5-heptenoic acid, methyl ester The title compound (0.79 g) was prepared from the product of Preparation 98 Table 4 (2 g) by the procedure described for Examples 48–59 Table 7 Method A.1. Chromatography on silica eluting with ether-menthanol 19:1 increasing to 17:3 gave the title compound as an orange oil. I.R. (CHBr$_3$) 3540, 1730$_{cm}$−1

T.L.C. silica 95:5 ether-methanol Rf. 0.32.

TABLE 10

| Ex. No. | Starting Material R | Z | Wt (g) | Product where Z in different | Solvent | Vol. (ml) | PO O/C Wt. (g) | Chromatography System | m.p. | Yield (g) | I.R. (CHBr₃) cm⁻¹ (Neat) | Tlc (silica) Rf (Solvent) |
|---|---|---|---|---|---|---|---|---|---|---|---|---|
| 93 | —CH₂Ph | piperidin-1-yl | 1.85 | — | ethanol | 75 | 0.35 | — | — | 1.91 | 3520, 3440, 1740 | |
| 94 | —CH₂Ph | PhCH₂(CH₃)N— | 1.0 | —NHCH₃ | ethyl acetate | 35 | 0.5 | — | 45–6° from EtoAc-petroleum ether | 0.4 | 3520, 1730 | 0.23(1:2 ethyl acetate-methanol) |
| 95 | —CH₃ | PhCH₂(CH₃)N— | 1.0 | —NHCH₃ | methanol | 20 | 0.2 | — | 106–8° from ethyl acetate | 0.63 | 3500, 1728 | 0.2 (methanol) |
| 96 | —CH₃ | PhCH₂(CH₃)N— | 0.37 | — | methanol + 5N HCl (0.25ml) | 20 | 0.073 | ether | — | 0.24 | 3080–3500, 1728 | 0.3 (ether) |
| 97 | —CH₂Ph | PhOCH₂CHCH₂(OH)(CH₃)N— | 0.42 | — | methanol | 20 | 0.05 | 3:17 methanol-ethyl acetate | — | 0.3 | 3580, 1728 | 0.45 (96:4 ether-methanol) |
| 98 | —CH(Ph)₂ | morpholin-4-yl | 0.8 | — | methanol | 50 | 0.15 | — | 109–10° from EtoAc-petroleum ether | 0.61 | 3530, 1725 | 0.32 (95:5 ether-methanol) |
| 99 | —CH₃ | morpholin-4-yl | 1.66 | — | ethanol | 80 | 0.3 | — | 33–34.5 | 1.63 | 3520, 1728 | 0.11 (ether) |
| 100 | —CH₂Ph | —N₃ | 13.5 | —NH₂ | methanol | 50 | 1.4 | — | 68–9° from EtoAc-petroleum ether | 5.8 | 3320, 3280, 3200, 1723 | 0.31(1:1 ether methanol) |
| 101 | —CH₂Ph | 4-butylpiperidin-1-yl | 3.5 | — | methanol | 90 | 0.3 | 94:6 ether-methanol | — | 2.6 | 3590, 3520, 1725 | 0.17 (95:5 ether-methanol) |
| 102 | —CH₂Ph | 2,6-dimethylmorpholin-4-yl | 0.36 | — | ethanol | 25 | 0.09 | 4:1 ether-petroleum ether | — | 0.20 | 3540, 1730 | 0.49 (95:5 ether-methanol) |

EXAMPLES 93-102

(1α,2β,3α,5α)-(±)-2,3,5-Trisubstituted cyclopentaneheptanoic acid, methyl esters Table 10 summarises the preparation of the title compounds by the following method:

A solution of the appropriate alkene in the solvent specified was hydrogenated over pre-reduced 10% palladium on charcoal at atmospheric pressure. When necessary an acid catalyst was used and this specified in the Table. When the hydrogen uptake ceases the mixture was filtered through hyflo and evaporated. The residue when necessary as either chromatographed on silica gel with the solvent specified or crystallised from the solvent specified to give the title compound.

EXAMPLE 103

(1α,2β,3α,5α)-(±)-3-Hydroxy-2-[N-(2-methoxyethyl)-N-methylamino]-5-(phenylmethoxy)cyclopentane heptanoic acid, methyl ester A mixture of the product of Example 94 (1.1 g), 2-bromoethylmethyl ether (2.1 g), anhydrous potassium carbonate (1.1 g) and dry acetonitrile (20 ml) was heated under reflux for 4½ hr. The reaction mixture was filtered and the filtrate concentrated in vacuo to yield an oil. Column chromatography on silica gel using (10:1) ether-methanol as eluent gave the title compound as an oil (0.9 g), IR (Neat) 3450, 1735 cm$^{-1}$.

T.l.c. (Silica) Rf 0.4 (acetone).

EXAMPLE 104

(1α,2β,3α,5α)-(±)-3-Hydroxy-2-[N-(2-hydroxyheptyl)-N-methylamino]-5-methoxycyclopentaneheptanoic acid, methyl ester A solution of the product of Example 95 (0.59 g) and 1,2-epoxyheptane (0.68 g) in methanol (10 ml) was heated under reflux for 12 hr. Evaporation of the solvent gave an oil which was chromatographed on silica gel using 100:1 ethyl acetate-triethylamine as eluent. Epimer A of the title compound was isolated as the least popular material (0.34 g) and Epimer B as the most popular (0.27 g).

Epimer A IR (Neat) 3420, 1740 cm$^{-1}$

Analysis Found: C, 65.23; H, 10.22; N, 3.53; $C_{22}H_4NO_5$ requires: C, 65.80; H, 10.79; N, 3.49%.

Epimer B IR (Neat) 3420, 1740 cm$^{-1}$.

Analysis Found: C, 65.01; H, 10.67; N, 3.47%.

EXAMPLE 105

(1α,2β,3α,5α)-(±)-3-Hydroxy-2-[N-(2-hydroxy-2-phenylethyl)N-methylamino]-5-methoxycyclopentaneheptanoic acid, methyl ester The process of Example 104 was repeated using the product of Example 95 (574 mg) and styrene oxide (480 mg), heating under reflux for 5 hr., to yield the title compound as an oil (530 mg). IR (Neat) 3400, 1740 cm$^{-1}$.

Analysis Found: C, 67.48; H, 9.21; N, 3.50%. $C_{23}H_{37}NO_5$, requires: C, 67.78; H, 9.15; N, 3.44%.

EXAMPLE 106

(1α,2β,3α,5α)-(±)-3-Hydroxy-2-[N-methyl-N-[2-hydroxy-3-[3-(trifluoromethyl)phenoxy]propyl]amino]5-methoxycyclopentaneheptanoic acid, methyl ester The process of Example 104 was repeated using a solution of the product of Example 95 (287 mg) and 1,2-epoxy-3-(3-trifluoromethyl)phenoxypropane (325 mg) in methanol (3 ml), heating under reflux for 3 hr, to yield the title compound as an oil (371.3 mg).

IR (Neat) 3420, 1740 cm$^{-1}$.

Analysis Found: C, 59.01; H, 7.65; N, 2.77 $C_{25}H_{38}F_3NO_6$ requires: C, 59.39; H, 7.58; N, 2.77%.

EXAMPLE 107

[1α,2β,3α,5α]-(±)-3,5-Dihydroxy-2-(4-morpholinyl)-cyclopentaneheptanoic acid, methyl ester A solution of the product of Example 16 (0.75 g) in methanol (110 ml) containing 60% perchloric acid (2 ml) was hydrogenated at atmospheric pressure and room temperature over 10% palladium on charcoal (400 mg). After 4 h the catalyst was removed by filtration through hyflo. The filtrate was poured into ammoniacal sodium chloride solution (150 ml) and extracted with dichloromethane (2×50 ml). The combined organic extracts were washed with brine (100 ml), dried (sodium sulphate) and evaporated to afford an oil (987 mg). The product was purified by short path column chromatography on silica gel (50 g). Elution with 10% methanol/ethyl acetate gave the title compound which was further purified by molecular distillation (0.37 g)

I.R. (Neat) 3400, 1735 cm$^{-1}$

Analysis Found: C, 61.7; H, 9.5; N, 4.1; $C_{17}H_{31}NO_5$ requires: C, 62.0; H, 9.5; N, 4.3%.

EXAMPLE 108

(1α,2β,3α,5α)-(±)-3,5-Dihydroxy-2-[N-methyl-N-(2-phenylethyl)amino]cyclopentaneheptanoic acid, methyl ester The product of Example 5 (Table 5) (0.74 g) was converted into the title compound (0.208 g) by the method of Example 107.

Analysis Found: C, 70.4; H, 9.3; N, 3.7; $C_{22}H_{35}NO_4$ requires: C, 70.0; H, 9.35; N, 3.7%.

I.R. (CHBr$_3$) 3590, 3520(sh), 1725 cm$^{-1}$

EXAMPLE 109

(1α,2β,3α,5α)-(±)-3-Hydroxy-2-[N-methyl-N-(2-phenylethyl)amino]-5-(phenylmethoxy)cyclopentaneheptanoic acid, methyl ester The title compound (1.38 g) was prepared from the product of Example 5 (Table 5) (1.5 g) in ethanol (20 ml) by the method of Examples 93-102 (Table 10). A portion (0.86 g) was distilled at 180°/0.1 mm Hg to give the title compound (0.62 g) as a pale yellow oil.

Analysis Found: C, 74.4; H, 8.9; N, 3.0 $C_{29}H_{41}NO_4$ requires: C, 74.5; H, 8.8; N, 3.0%.

EXAMPLE 110

(1α,2β,3α,5α)-(±)-5-Acetoxy-3-hydroxy-2-(4-morpholinyl)cyclopentane heptanoic acid, methyl ester The product from Example 22 (0.9 g) was converted into the title compound (0.71 g) by the method described for Examples 93-102. Crystallisation from ether-petroleum ether gave white needles m.p. 50.5°-51.5°.

Analysis Found: C, 60.5; H, 8.8; N, 3.9; $C_{19}H_{33}NO_6$ requires: C, 61.4; H, 9.0; N, 3.8%.

EXAMPLE 111

(1α,2β,3α,5α)-(±)-3-Hydroxy-5-(1-methylethoxy)-2-(4-morpholinyl)-cyclopentaneheptanoic acid, methyl ester, hydrochloride The title compound base was prepared from the product of Example 18 (1 g) in methanol (50 ml) by the method of Examples 93-102 (Table 10). The base in ether was treated with an excess of ethereal hydrogen chloride. Purification from ethyl acetate gave the title compound (0.54 g) m.p. 131°-132° C.

Analysis Found: C, 59.2; H, 9.3; N, 3.4; $C_{20}H_{37}NO_5.HCl$ requires: C, 58.9; H, 9.3; N, 3.4%.

EXAMPLE 112

(1α,2α,5β)-(±)-2-Hydroxy-5-(4-morpholinyl)cyclopentane heptanoic acid, methyl ester, hydrochloride The title compound base was prepared from the product of Example 33 (1.9 g) in methanol (100 ml) by the method of Examples 93-102 (Table 10). The base in ether was treated with an excess of ethereal hydrogen chloride. Purification from methanol-ethyl acetate gave the title compound (1.6 g) m.p. 160°-163°.

Analysis Found: C, 58.3; H, 9.6; N, 4.0; $C_{17}H_{31}NO_4.HCl$ requires: C, 58.4; H, 9.2; N, 4.0%.

EXAMPLE 113

(1α,2α,5β)-(±)-5-(4-Morpholinyl)-2-(phenylmethoxy)-cyclopentane-heptanoic acid, methyl ester, hydrochloride, hemihydrate A solution of the product of Example 112 (1.55 g) in sodium bicarbonate solution was extracted with dichloromethane. The free base in dimethylformamide (20 ml) containing benzyl bromide (3.03 g) was stirred at 0° while potassium tertiary butoxide (0.993 g) was added. The cooling bath was removed after ca. 5 min and the reaction was stirred at room temperature for 1 h. The reaction mixture was poured into an excess of ammonium chloride solution and extracted with ethyl acetate. The combined extracts were dried and evaporated to give a yellow oil which was filtered through a short silica column in ether to remove the excess of benzyl bromide. The residual oil was chromatographed on silica in ethyl acetate to give a colourless oil (400 mg). The oil was dissolved in dry ether and treated with an excess of ethereal hydrogen chloride to give a tan solid (400 mg). Purification from ethyl acetate-methanol gave the title compound as an off-white solid (260 mg) m.p. 118°-120°.

Analysis Found: C, 64.2; H, 8.5; N, 3.2; $C_{24}H_{37}NO_4.HCl.\frac{1}{2}H_2O$ requires: C, 64.2; H, 8.75; N, 3.1%.

EXAMPLE 114

(1α,2β,3α,5α)-(±)-3-Hydroxy-2-[N-methyl-N-[2-hydroxy-3-(3-trifluoromethylphenoxy)-propyl]amino]-5-methoxycyclopentaneheptanoic acid, methyl ester A solution of the product of Example 95 (287 mg) and 1,2-epoxy-3-(3-trifluoromethylphenoxy)propane (325 mg) in methanol (325 mg) in methanol (3 ml) was heated under reflux for 3 h. Removal of the solvent gave an oil which was purified by chromatography on silica. Eluting with ether gave the title compound as a colourless oil (371 mg).

Analysis Found: C, 59.0; H, 7.65, N, 2.8; $C_{25}H_{38}F_3NO_6$ requires: C, 59.4; H, 7.6; N, 2.8% I.R. (Neat) 3420, 1740 cm$^{-1}$

EXAMPLE 115

(1α,2β,3α,5α)-(±)-3-Hydroxy-5-methoxy-[N-(2-methoxyethyl)-N-methylamino]cyclopentaneheptanoic acid, methyl ester A mixture of the product of Example 95 (Table 10) (1.5 g), 2-bromoethyl methyl ester (3.0 g), anhydrous potassium carbonate (1.5 g) and dry acetonitrile (10 ml) was refluxed for 5 h. The solvent was removed in vacuo and the residue treated with ether (50 ml) and filtered. Removal of the solvent from the filtrate gave a pale orange oil (1.75 g). Molecular distillation (160°/0.01 mm) gave the title compound as a colourless oil (1.164 g). I.R. (Neat) 3600-3200, 1739 cm$^{-1}$ Analysis Found: C, 61.4; H, 10.1; N, 3.9; $C_{18}H_{35}NO_5$ requires: C, 62.6; H, 10.2; N, 4.1%.

EXAMPLE 116

(1α,2β,3α,5α)-(±)-3-Hydroxy-2-(methylamino)-5-(phenylmethoxy)cyclopentane heptanoic acid, methyl ester The product of Example 5 (Table 5) (1.0 g) in ethyl acetate (20 ml) was added to a pre-hydrogenated suspension of 10% palladium oxide on charcoal (0.5 g) in ethyl acetate (15 ml). The reaction was stirred for 3 h. The reaction mixture was filtered and the solvent removed to give a solid (0.64 g). Purification from petroleum ether-ethyl acetate 10:1 gave the title compound as pink needles (0.41 g) m.p. 45° C.

Analysis Found: C, 69.7; H, 9.2; N, 3.8; $C_{21}H_{33}NO_4$ requires: C, 69.4; H, 9.15; N, 3.85%.

EXAMPLE 117

(1α,2β,3α,5α)-(±)-3-hydroxy-2-[N-hydroxyethyl)-N-(methylamino)]-5-(phenylmethoxy)cyclopentane heptanoic acid, mthyl ester A mixture of the product of Example 116 (1 g) and 25% ethylene oxide in toluene solution (20 ml) was heated (90°) in an autoclave for 3 days. Excess solvent was evaporated under reduced pressure to afford a viscous brown oil (1.2 g). Column chromatography on silica gel with methanol as the eluent gave the title compound as a yellow oil (0.86 g). I.R. (Neat) 3400, 1735 cm$^{-1}$ Analysis Found: C, 67.4; H, 9.1; N, 3.4; $C_{23}H_{37}NO_5$ requires: C, 67.8; H, 9.2; N, 3.4%.

EXAMPLE 118

(1α,2β,3α,5α)-(±)-3-Hydroxy-5-(phenylmethoxy)-2-(4-thiomorpholinyl)cyclopentaneheptanoic acid, methyl ester, S-dioxide, maleate A solution of the product of Example 4(Table 5) (1 g) in methanol (40 ml) was hydrogenated over prereduced 10% palladium oxide on charcoal (250 mg) for 15 min. The catalyst and the solvent were removed giving a gum (1.0 g). The product was purified by chromatography on silica eluting with ether to give a colourless oil. The oil was dissolved in ether and treated with an excess of an ethereal solution of maleic acid. The precipitated gum was triturated with ether to give the title compound (590 mg) m.p. 95°-97°.

Analysis Found C, 57.25; H, 7.1; N, 2.5; $C_{24}H_{37}SNO_6.C_4H_4O_4$ requires: C, 57.6; H, 7.0; N, 2.4%.

EXAMPLE 119

(1α,2β,3α,5α)-(±)-2-(Hexahydro-1H-azepinyl)-3-hydroxy-5-(phenylmethoxy)cyclopentane heptanoic acid, methyl ester hydrochloride Anhydrous potassium carbonate (2.76 g) was added to a solution of the product of Example 100 (3.5 g) and 1,6-dibromohexane (2.93 g) in dry acetonitrile (30 ml) and the mixture heated under reflux for 8 h. The suspension was filtered and the filtrate evaporated. The residue was purified by chromatography on silica eluting with 4% methanol in ether to give the product (2 g) as a pale orange oil. A sample (600 mg) in ether (15 ml) was treated with an excess of ethereal hydrogen chloride. The product was purified from ethyl acetate-petroleum ether to give the title compound as colourless platelets m.p. 75°–6°.

Analysis Found: C, 66.6; H, 9.1; N, 3.0; $C_{26}H_{41}NO_4 \cdot HCl$ requires: C, 66.7; H, 9.0; N, 3.0%.

EXAMPLE 120

(1α,2β,3α,5α)-(±)-3-Hydroxy-5-(phenylmethoxy)-2-(1-pyrrolydinyl)cyclopentane heptanoic acid, methyl ester, hydrochloride Anhydrous potassium carbonate (2.4 g) was added to a solution of the product of Example 100 (4 g) and 1,4-dibromobutane (2.98 g) in dry acetonitrile (30 ml) and the mixture heated under reflux for 18 h. The suspension was filtered and the filtrate was diluted with ether (100 ml) and washed with 8% sodium bicarbonate (50 ml). The aqueous phase was back-extracted with ether (2×30 ml). The combined organic phases were washed with brine, dried ($Mg_gSO_4$) and evaporated. The residual oil was purified by chromatography on silica eluting with 10% methanol in ether to give the product (2.51 g) as a pale orange oil which slowly solidified on standing (m.p. 34°–35°). A sample (800 mg) in ether (20 ml) was treated with an excess of ethereal hydrogen chloride. The product was purified from ethyl acetate-petroleum ether to give the title compound as off-white platelets m.p. 88°–89°.

Analysis Found: C, 65.6; H, 8.9; N, 3.2; $C_{24}H_{37}NO_4 \cdot HCl$ requires: C, 65.5; H, 8.6; N, 3.2%.

EXAMPLE 121

[1α,2β(2±),3α,5α]-(±)-2-[N-(2-Chloroacetyloxyheptyl)-N-methylamino]-3-hydroxyl-5-(phenylmethoxycyclopentane heptanoic acid, methyl ester The product of Preparation 112 (1.8 g) in methanol (5 ml) was treated with 5% concentrated sulphuric acid in methanol (25 ml) at −10°. After stirring for 2.5 h the solution was neutralised with 8% sodium bicarbonate solution and extracted with dichloromethane (3×100 ml). The combined organic extracts were washed with brine, dried ($MgSO_4$) and concentrated to afford an orange viscous oil. The product was purified by chromatography on silica. Elution with petroleum ether in ether 2:3 gave the title compound as a yellow oil (1.2 g).

I.R. (Neat) 3540, 3460, 1765 (sh), 1740 cm$^{-1}$

Analysis Found: C, 64.55; H, 8.7; N, 2.5; $C_{30}H_{48}ClNO_6$ requires: C, 65.0; H, 8.7; N, 2.5%.

EXAMPLE 122

[1α,2β,3α,5α]-(±)-2-[N-(2-Chloroacetyloxyethyl)-N-methylamino]-3-hydroxy-5-(phenylmethoxy)cyclopentane heptanoic acid, methyl ester A cold (0°) solution of the product of Preparation 110 (1.87 g) in methanol (10 ml) was acidified with ethereal hydrogen chloride and left stirring for 45 min. The solution was diluted with ether (100 ml) and washed with 8% sodium bicarbonate solution (100 ml). The aqueous phase was re-extracted with ether (50 ml). The combined organic extracts were dried ($MgSO_4$), filtered and evaporated to afford an oil (1.6 g). Column chromatography on silica gel with ether as eluent gave the title compound (0.60 g) as a pale yellow oil.

T.l.c. (Silica) Rf 0.3 (Ether).

Analysis Found: C, 61.6; H, 7.8; N, 2.8; $C_{25}H_{38}ClNO_6$ requires: C, 62.0; H, 7.9; N, 2.9%.

EXAMPLES 123–137

7-(2,5-Disubstituted-3-oxocyclopentyl)heptanoic acid, methyl esters

Table 11 summarises the preparation of the title compounds by the following methods:

A. Jones reagent [chromium trioxide (26.7 g) and concentrated sulphuric acid (23 ml) made up to 100 ml with water] was added dropwise to the appropriate alcohol in acetone at −5° to 0° and stirred for 0.5–5 h. The mixture was poured into cold (0°) 8% aqueous sodium bicarbonate solution and extracted with ether. The combined organic extracts were dried ($MgSO_4$), filtered and concentrated. The material obtained was purified by chromatography on slica gel.

B. The method is as described in Method A except that isopropanol is added to destroy the excess of Jones reagent and the chromium residues are removed by filtration. The product is isolated from the filtrate as described in Method A.

TABLE 11

[Reaction scheme: starting material (cyclopentane with OR, CH₂-X-CH₂CH₂CH₂-CO₂CH₃ chain, and N-Z group, OH) → product (cyclopentanone with OR, same chain, N-Z group, =O)]

| Ex. No. | Starting Material Z | R | X | Wt. (g) | Method | Acetone Vol (ml) | Jones Reagent Vol. (ml) | Time hr. | I.P.A. Vol. (ml) | Chromatography System ether-petrol. ether | Yield (g) | I.R. (CHBr₃) cm⁻¹ | Tlc (silica) Rf (solvent) |
|---|---|---|---|---|---|---|---|---|---|---|---|---|---|
| 123 | piperidine (−N⟨(CH₂)₅⟩) | CH₂Ph | CH=CH(cis) | 1.2 | A | 35 | 2.7 | 2.7 | 2 | 1:1 ether | 0.59 | 1730 | 0.54 (ether) |
| 124 | piperidine | CH₂Ph | CH₂CH₂ | 1.116 | A | 35 | 2.5 | 2 | — | 1:1 | 0.735 | 1730 | 0.58 (ether) |
| 125 | −N(CH₂CH₂OCH₃)(CH₂...) | CH₂Ph | CH₂CH₂ | 0.6 | B | 15 | 1.0 | 2 | 2 | 1:1 | 0.242 | 1730 | 0.45 (ether) |
| 126 | morpholine | CH₃ | CH=CH(cis) | 1.5 | A | 50 | 2.3 | 4.5 | — | 3:1 | 0.96 | 1735 | 0.33 (ether) |
| 127 | −N(CH₃)(CH₂CH₂Ph) | CH₂Ph | CH=CH(cis) | 1.0 | A | 50 | 1.6 | 1 | — | 4:6 | 0.58 | 1730 | 0.7 (ether) |
| 128 | −N(CH₃)(CH₂CH₂Ph) | CH₂Ph | CH₂CH₂ | 0.8 | A | 25 | 1.4 | 1.5 | — | 3:7 | 0.26 | 1730 | 0.7 (ether) |
| 129 | −N(CH₃)(CH₂Ph) | CH₃ | CH=CH(cis) | 0.7 | A | 25 | 1.05 | 2 | — | 1:2 | 0.39 | 1730 | 0.55 (ether) |

TABLE 11-continued

[Starting material structure with OR, HO, X, CO₂CH₃ → product with OR, =O, X, CO₂CH₃]

| Ex. No. | Starting Material Z | R | X | Wt. (g) | Method | Acetone Vol (ml) | Jones Reagent Vol. (ml) | Time hr. | I.P.A. Vol. (ml) | Chromatography System ether-petrol. ether | Yield (g) | I.R. (CHBr₃) cm⁻¹ | Tlc (silica) Rf (solvent) |
|---|---|---|---|---|---|---|---|---|---|---|---|---|---|
| 130 | —N(CH₃)(CH₂CH₂OCH₃) | CH₃ | CH₂CH₂ | 0.57 | B | 10 | 2.0 | 3 | 2 | 2:1 | 0.47 | 1730 | 0.4 (ether) |
| 131 | —N(CH₃)((CH₂)₂O(CH₂)₂CH₃) | —CH₂Ph | CH=CH(cis) | 1.2 | B | 50 | 1.16 | 0.5 | 10 | 7:3 | 0.63 | 1730 | 0.47 (7:3 ether-petroleum ether) |
| 132 | morpholino (—N⟨O⟩) | CH₃ | CH₂CH₂ | 1 | A | 30 | 2.73 | 3 | — | 3:1 | 0.85 | 1730 | 0.32 (ether) |
| 133 | pyrrolidino (—N⟨⟩) | —CH₂Ph | CH₂CH₂ | 1.4 | B | 100 | 1.9 | 2 | 10 | 3:2 | 0.36 | 1730 | 0.27 (3:2 ether-petroleum ether) |
| 134 | hexamethyleneimino (—N⟨⟩) | —CH₂Ph | CH₂CH₂ | 1.5 | B | 100 | 2.32 | 2 | 10 | 3:7 | 0.265 | 1730 | 0.23 (3:7 ether-petroleum ether) |
| 135 | 4-OH-4-(CH₂)₃CH₃-piperidino | —CH₂Ph | CH=CH(cis) | 0.92 | A | 10 | 1.26 | 1 | — | 4:1 | 0.42 | 3595, 1730 | 0.54 (ether) |

TABLE 11-continued

Starting Material → Product (cyclopentane with OR, Z, and X-CO₂CH₃ substituents, ketone)

| Ex. No. | R | Z | X | Wt. (g) | Method | Acetone Vol (ml) | Jones Reagent Vol. (ml) | Time hr. | I.P.A. Vol. (ml) | Chromatography System ether-petrol. | Yield (g) | I.R. (CHBr₃) cm⁻¹ | Tlc (silica) Rf (solvent) |
|---|---|---|---|---|---|---|---|---|---|---|---|---|---|
| 136 | —CH₂Ph | 4-hydroxy-4-(CH₂)₃CH₃-piperidin-1-yl | CH₂CH₂ | 1.37 | B | 40 | 1.87 | 0.7 | 10 | ether 4:1 | 0.81 | 3590, 1730 | m.p. 32–34° 0.46 (ether) |
| 137 | —CH₂-C₆H₄-Ph | piperidin-1-yl | CH=CH (cis) | 0.72 | B | 15 | 0.97 | 2.5 | 1 | ether | 0.32 | 1740 | 0.5 (ether) |

EXAMPLE 138

[1α(Z),2β]-(±)-7-[2-(4-Morpholinyl)-3-oxocyclopent-4-en-1-yl]-5-heptenoic acid, methyl ester To a stirred solution of the product of Example 22 (3.0 g) in acetone (100 ml) at 0° was added Jones reagent (4.0 ml). The mixture was stirred at 0.5° for 3 hr. whereupon isopropanol (5 ml) was added. After a further 15 min., 8% aqueous sodium bicarbonate solution (100 ml) was added. The mixture was extracted into dichloromethane (3×50 ml) and the combined organic phases dried and evaporated. The residual oil was dissolved in pyridine (10 ml) and stood for 18 hr. Excess pyridine was removed in vacuo and the residue chromatographed on slica gel using ether as eluent, to give the title compound as an oil (1.3 g). IR (Neat) 1735, 1710 cm$^{-1}$.

Analysis Found: C, 66.0; H, 8.4; N, 4.5; $C_{17}H_{25}NO_4$ requires: C, 66.4; H, 8.2; N, 4.6%.

EXAMPLE 139

(1α,2β)-(±)-2-[4-(Morpholinyl)]3-oxocyclopentaneheptanoic acid, methyl ester

A solution of the product from Example 138 (600 mg) in ethyl acetate (100 ml) was hydrogenated at atmospheric pressure over prereduced 10% palladium oxide on charcoal (50 mg). The catalyst was filterd off and the solution evaporated under reduced pressure to afford an oil which was purified by column chromatography on silica gel using ether as eluent to yield the title compound as an oil (502 mg) which slowly solidified, m.p. 31°-2°. IR (CHBr$_3$) 1730 cm$^{-1}$.

Analysis Found: C, 66.1; H, 9.6; N, 4.6; $C_{17}H_{29}NO_4$ requires: C, 65.6; H, 9.3; N, 4.5%.

EXAMPLE 140

[1α(Z),2β]-7-[2-[N-(2-Hydroxyheptyl)-N-methylamino]-5-oxo-3-cyclopenten-1-yl]-5-heptenoic acid, methyl ester Jones reagent (3 M, 0.43 ml) was added dropwise to a stirred solution of the product of Example 27 (0.69 g) in acetone (25 ml) at 0°. The mixture was stirred at 0° for 2 hr., diluted with 8% aqueous sodium bicarbonate solution (30 ml) and extracted with ether (3×30 ml). The combined extracts were washed, dried and evaporated to give an oil which was purified by chromatography on silica gel. Elution with ether gave the title compound as an oil (0.245 g). IR (Neat) 3460, 1740, 1710 cm$^{-1}$.

Analysis Found: C, 68.71; H, 9.67; N, 3.81; $C_{21}H_{35}NO_4$ requires: C, 69.00; H, 9.65; N, 3.83%.

EXAMPLE 141

[1α(Z),2β]-(±)-7-[[2-N-Methyl-N-(phenylmethyl)amino]-5-oxo-3-cyclopentenyl]-5-heptenoic acid, methyl ester The title compound (0.73 g) was prepared from the product of Example 32 (1.0 g) by the method described for Examples 123–137 (Table 11). (Method A). Chromatography on silica using ether as eluent gave the title compound as a colourless oil. I.R. (CHBr$_3$) 1723, 1700 cm$^{-1}$.

Analysis Found: C, 74.0; H, 7.75; N, 4.1; $C_{21}H_{27}NO_3$ requires: C. 73.9; H, 8.0; N, 4.1%.

EXAMPLE 142

[1α(Z),2β,5α]-(±)-7-[-(4-Morpholinyl)-3-oxo-5-(phenylmethoxy)cyclopentyl]-5-heptenoic acid To a cold (0°) solution of the product of Example 30 (3.3 g) in acetone (150 ml) was added Jones reagent (4.0 ml, 3.0 molar) and the mixture stirred for 1½ h. Isopropanol (15 ml) was added and the stirring maintained for 30 min. The suspension was filtered, the filtrate neutralised with 8% sodium bicarbonate solution and evaporated. The residue was diluted with water (20 ml) and the pH adjusted to 7.0 by adding 2 N hydrochloric acid. The suspension was extracted with dichloromethane (4×50 ml). The combined organic extracts were dried (MgSO$_4$), filtered and evaporated to yield an oil (2.8 g) which was subjected to short path column chromatography on silica gel (Merck 7731, 90 g). Eluting with ether gave the title compound (2.14 g) I.R. (CHBr$_3$) 3500, 1740, 1703 cm$^{-1}$.

T.l.c. (Silica) Rf 0.39 (ether).

EXAMPLE 143

[1α(Z),2β,5α]-(±)-7-[5-[[(1,1'-Biphenyl)-4-yl]methoxy]-2-(4-morpholinyl)-3-oxo-cyclopentyl]-5-heptenoic acid To a cold (0°) stirred solution of the product of Example 77 (2.0 g) in analar acetone (50 ml) was added Jones reagent (2.34 ml) (3 M solution). After 4 hr. isopropanol (25 ml) was added and stirring maintained for a further 30 min. The suspension was neutralised (pH 7) with 8% sodium bicarbonate solution, poured into saturated ammonium chloride solution (200 ml) and extracted with dichloromethane (6×70 ml). The combined extracts were dried (MgSO$_4$) and evaporated, and the residue was purified by chromatography on silica. Eluting with ether/petrol 9:1 gave the title compound as a colourless oil (0.71 g) which solidified on cooling m.p. 68°-70°.

Analysis Found: C, 72.6; H, 7.5; N, 2.9; $C_{29}H_{35}NO_5$ requires: C, 72.9; H, 7.4; N. 2.9%.

EXAMPLE 144

[1α(Z),2β,5α]-(±)-7-[5-(4-Cyclohexylphenylmethoxy)-2-(4-morpholinyl)-3-oxo-cyclopentyl]-5-heptenoic acid To a stirred cold (0°) solution of the product of Example 80 (1.6 g) in analar acetone (50 ml) was added dropwise Jones reagent (1.8 ml). After 3 h isopropanol (10 ml) was added and stirring maintained for a further 30 min. The green suspension was neutralised (pH 7) by 8% sodium bicarbonate solution then poured into saturated ammonium chloride solution (200 ml) and extracted with dichloromethane (5×75 ml). The combined extracts were dried (MgSO$_4$) and evaporated to afford a dark brown oil (1.51 g). The product was purified by chromatography on silica. Eluting with ether gave the title compound (0.735 g) as a straw coloured viscous oil. I.R. (CHBr$_3$) 3480, 1740, 1705 cm$^{-1}$.

Analysis Found: C, 72.4; H, 8.2; N, 2.9; $C_{29}H_{41}NO_5$ requires: C, 72.0; H, 8.6; N, 2.9%.

EXAMPLE 145

(1α,2β,3α,5α)-(±)-5-[[(1,1'-Biphenyl)-4-yl]methoxy-3-hydroxy-2-(4-morpholinyl)cyclopentane]heptanoic acid, methyl ester A solution of the product of Example 76 (2 g) in ethyl acetate (50 mls) was hydrogenated over pre-reduced palladium oxide on charcoal (0.5 g) in ethyl acetate (25 mls). Hydrogen uptake ceased after 2 hrs. (hydrogen uptake 95 mls, theoretical 91 mls). The mixture was filtered (hyflo) and evaporated to afford the title compound as a viscous oil (2.16 g).

T.L.C. SiO$_2$,3% methanol in ether, Rf. 0.30, I.R. (Neat) 3450, 1738 cm$^{-1}$.

EXAMPLE 146

(1α,2β,3α,5α)-(±)-5-[[(1,1'-Biphenyl)4-yl]methoxy]-3-hydroxy-2-(4-morpholinyl)cyclopentane heptanoic acid A mixture of the product of Example 145 (2.0 g) and potassium hydroxide (0.45 g) in methanol (10 mls) and water (10 mls) was stirred for 4½ hrs. The suspension was then evaporated under reduced pressure, the residue dissolved in water (30 mls), acidified (pH 6.5) with 2 M sodium hydrogen sulphate and extracted into dichloromethane (3×50 mls). The combined extracts were dried (MgSO$_4$), filtered and evaporated to afford the title compound as a foam. (1.7 g). I.R. (CHBr$_3$) 3500, 1740, 1710 cm$^{-1}$.

Analysis Found: C, 72.2; H, 8.05; N, 2.8; C$_{29}$H$_{39}$NO$_5$ requires: C, 72.3; H, 8.2; N, 2.9%.

EXAMPLE 147

(1α,2β,5α)-(±)-5-[[1,1'-Biphenyl)-4-yl]methoxy]-2-(4-morpholinyl)-3-oxocyclopentane heptanoic acid A cold (0°) solution of the product of Example 146 (1.6 g) in acetone (50 mls) was treated with Jones reagent (1.5 mls) and left standing for 30 mins. Isopropanol (10 mls) was added and stirring maintained for a further 15 mins. The mixture was brought to pH 6.5 with 8% sodium bicarbonate solution; poured into ammonium chloride solution (150 mls) and extracted into dichloromethane (3×100 mls). The combined extracts were dried (MgSO$_4$), filtered and evaporated to afford a green solid (1.46 g). Chromatography on silica with ether as eluent gave the title compound as white crystalline solid (0.904 g), m.p. 111.5°–112.5°.

Analysis Found: C, 72.7; H, 7.9; N, 2.9; C$_{29}$H$_{37}$NO$_5$ requires: C, 72.6; H, 7.8; N, 2.9%.

EXAMPLES 148–170

7-(2,5-Disubstituted-3-oxocyclopentyl)heptanoic acid, methyl esters

Table 12 summarises the preparation of the title compounds by the following method:

To a stirred solution of the appropriate alcohol and dicyclohexyl carbodiimide in dry dimethyl sulphoxide at room temperature was added pyridinium trifluoroacetate. After the time specified the mixture was poured into water and extracted with dichloromethane or ether. The remaining work-up is as described in Method A. Table 11.

TABLE 12

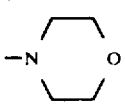

| Ex. No. | Starting Material Z | R | DMSO Vol. (ml) | DCC Wt. (g) | Py. TFA Wt. (g) | Time (h) | Chromatography System ether-petroleum ether | Yield (g) | I.R. (CHBr$_3$) cm$^{-1}$ | Tlc (Silica) Rf (Solvent) |
|---|---|---|---|---|---|---|---|---|---|---|
| 148 | 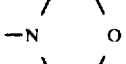 | —CH$_2$Ph | 2.4 | 50 | 4.74 | 1.68 | 1 | 7:3 | 1.81 | 1738 | 0.28 (7:3 ether-petroleum ether) |
| 149 |  | —CH$_2$—⟨⟩—OMe | 0.87 | 15 | 1.6 | 0.48 | 1 | 7:3 | 0.61 | 1738 | 0.59 (ether) |
| 150 | 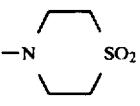 | —CH$_2$Ph | 0.56 | 10 | 1.25 | 0.35 | 20 | ether | 0.31 | 1740 | 0.25 (ether) |
| 151 | 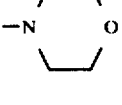 | —CH$_2$—⟨⟩—Br | 0.77 | 15 | 1.28 | 0.45 | 0.75 | 7:3 | 0.5 | 1735 | 0.44 (ether) |
| 152 |  | —CH$_2$—⟨⟩—Me | 0.72 | 15 | 1.38 | 0.48 | 1 | 7:3 | 0.54 | 1738 | 0.54 (ether) |

TABLE 12-continued

| Ex. No. | Starting Material Z | Starting Material R | DMSO Wt. (g) | DMSO Vol. (ml) | DCC Wt. (g) | Py. TFA Wt. (g) | Time (h) | Chromatography System ether-petroleum ether | Yield (g) | I.R. (CHBr$_3$) cm$^{-1}$ | Tlc (Silica) Rf (Solvent) |
|---|---|---|---|---|---|---|---|---|---|---|---|
| 153 | morpholino | —CH$_2$OCH$_3$ | 0.4 | 14 | 0.89 | 0.42 | 3 | 9:1 | 0.19 | 1735 | 0.36 (ether) |
| 154 | morpholino | —CH$_2$O(CH$_2$)$_2$OMe | 0.7 | 10 | 1.41 | 0.5 | 1 | ether | 0.34 | 1736 | 0.37 (ether) |
| 155 | morpholino | —CH$_2$—C$_6$H$_4$—CN | 0.88 | 15 | 1.65 | 0.58 | 1 | ether | 0.55 | 2270, 1738 | 0.37 (ether) |
| 156 | morpholino | —SiMe$_2$$^t$Bu | 1.32 | 20 | 2.47 | 0.87 | 1 | 55:45 | 0.83 | 1735 | 0.66 (ether) |
| 157 | morpholino | —CHPh$_2$ | 2.0 | 20 | 3.34 | 1.2 | 2 | 3:1 | 1.4 | 1735 | 0.5 (ether) |
| 158 | morpholino | —CH$_2$CH$_2$Ph | 1.5 | 20 | 2.87 | 1.34 | 1 | 6:4 | 1.1 | 1735 | m.p. 32.5–33.5° from ether-petroleum ether |
| 159 | morpholino | —CHMe$_2$ | 2.0 | 30 | 4.5 | 2.1 | 1 | 4:1 | 1.67 | 1733 | 0.35 (4:1 ether-petroleum ether) |
| 160 | morpholino | —CH$_2$—C$_6$H$_4$—OCH$_2$Ph | 0.6 | 7 | 0.94 | 0.34 | 1 | 4:1 | 0.4 | 1735 | 0.31 (4:1 ether-petroleum ether) |
| 161 | morpholino | —CH$_2$—C$_6$H$_4$—OMe | 0.9 | 10 | 1.66 | 0.6 | 1 | 4:1 | 0.7 | 1738 | 0.44 (4:1 ether-petroleum ether) |
| 162 | morpholino | —CH$_2$—C$_6$H$_{11}$ | 0.4 | 7 | 0.67 | 0.24 | 2 | 3:2 | 0.2 | 1738 | 0.38 (7:3 ether-petroleum ether) |

TABLE 12-continued

| Ex. No. | Starting Material Z | R | Wt. (g) | DMSO Vol. (ml) | DCC Wt. (g) | Py. TFA Wt. (g) | Time (h) | Chromatography System ether-petroleum ether | Yield (g) | I.R. (CHBr₃) cm⁻¹ | Tlc (Silica) Rf (Solvent) |
|---|---|---|---|---|---|---|---|---|---|---|---|
| 163 | —N(morpholino) | —CH₂—(2,3-dichlorophenyl) | 1.2 | 10 | 2.03 | 0.73 | 1 | 4:1 | 0.86 | 1735 | 0.35 (4:1 ether-petroleum ether) |
| 164 | —N(morpholino) | —CH₂Ph | 0.5 | 5 | 0.96 | 0.34 | 0.5 | ether | 0.25 | 1738 | 0.59 (95:5 ether-methanol) |
| 165 | —N(morpholino) | —CH₂CH=CH₂ | 1.15 | 10 | 2.56 | 0.93 | 1 | 7:3 | 0.86 | 1740 | 0.29 (3:2 ether-petroleum ether) |
| 166 | —N(morpholino) | —C₂H₁₁ | 0.9 | 10 | 1.93 | 0.69 | 1 | 7:3 | 0.62 | 1735 | 0.31 (3:2 ether-petroleum ether) |
| 167 | —N(CH₃)(C₇H₁₅) | CH₂Ph | 1.4 | 35 | 2.52 | 1.18 | 1 | 2:3 | 0.48 | 1730 | 0.48 (2:3 ether-petroleum ether) |
| 168 | —N(morpholino) | —CH₂—(3-Ph-phenyl) | 1.0 | 15 | 1.67 | 0.59 | 0.75 | 4:1 | 0.47 | 1735 | 80–81° from ether-petroleum ether. |
| 169 | —N(morpholino) | —CH(Me)Ph | 1.3 | 10 | 2.49 | 0.89 | 2 | 3:2 | 1.12 | 1738 | 0.39 (7:3 ether-petroleum ether) |
| 170 | —N(morpholino) | —CH₂—(3,5-dimethylphenyl) | 0.7 | 10 | 1.3 | 0.46 | 0.5 | 4:1 | 0.62 | 1735 | 0.38 (4:1 ether-petroleum ether) |

EXAMPLE 171

[1α(E),2β,5α]-(±)-7-[2-(4-Morpholinyl)-3-Oxo-5-(phenylmethoxy)cyclopentyl]-5-heptenoic acid, methyl ester To a cold (5°) stirred solution of the product from Example 21 (1.05 g) and dicyclohexyl carbodimide (2.59 g) in dimethylsulphoxide (7 ml) and dry dimethoxyethane (3 ml) was added pyridinium trifluoroacetate (0.73 g). After 15 mins., the cooling bath was removed and stirring continued for 2 hr. at room temperature. The resulting suspension was worked up according to the method of Example 148 to afford an oil (0.81 g) which crystallised on cooling. After recrystallisation from ether-petroleum ether the title compound had m.p. 51°-2°. IR (CHBr₃) 1735, 970 cm⁻¹.

Analysis Found: C, 69.6; H, 8.1; N, 3.7; $C_{24}H_{33}NO_5$ requires: C, 69.4; H, 8.0; N, 3.4%.

EXAMPLE 172

[1α(E),2β,5α]-(±)-7-[3-Oxo-5-phenylmethoxy)-2-(1-piperidinyl)cyclopentyl]-5-heptenoic acid, methyl ester The title compound (0.365 g) was prepared from the product of Example 44 (0.57 g) by the method of Examples 148–170, Table 12. Chromatography on silica eluting with ether-petroleum ether 2:3 gave the title compound as an orange oil. I.R. (CHBr$_3$) 1730 cm$^{-1}$.

Analysis Found: C, 72.2; H, 8.7; N, 3.4; C$_{25}$H$_{35}$NO$_4$ requires: C, 72.6; H, 8.5; N, 3.4%.

EXAMPLE 173

(1α,2β)-(±)-7-[2-(4-Morpholinyl)-3-oxocyclopent-4-en-1-yl]heptanoic acid, methyl ester Pyridinium trifluoroacetate (803 mg) was added to the product of Example 110 (1.023 g) and dicyclohexyl carbodiimide (0.71 g) in dimethyl sulphoxide (15 ml) and the mixture stirred for 2 hr. The suspension was poured into water (100 ml) and extracted into ether (4×50 ml). The combined organic phases were filtered to remove dicyclohexyl urea. The filtrate was washed with water (100 ml) followed by brine, dried (MgSO$_4$) and evaporated under reduced pressure to afford an oil (1.25 g). The residue was dissolved in pyridine (20 ml) and left at room temperature for 48 hr. Excess pyridine was removed under high vacuum (1 mm) to afford a semi-solid. The residue was subjected to short path column chromatography on silica gel (100 g). Elution with diethyl ether gave the title compound as an oil (0.552 g). I.R. (CHBr$_3$) 1725, 1705 cm$^{-1}$.

Analysis Found: C, 65.6; H, 9.1; N, 4.4; C$_{17}$H$_{27}$NO$_4$ requires: C, 66.0; H, 8.8; N, 4.5%.

EXAMPLE 174

[1α(Z),2β]-(±)-7-[2-(4-Morpholinyl)-5-oxo-3-cyclopenten-1-yl]-5-heptenoic acid, methyl ester To a solution of the product of Preparation 113 (0.8 g), in dry tetrahydrofuran (15 ml) was added tetrabutyl ammonium fluoride (1.56 g). The solution was allowed to stand at room temperature for 30 min., then poured into brine (50 ml) and extracted into ether (3×50 ml). The combined ethereal layers were dried (MgSO$_4$) and evaporated. The residual oil was purified twice by short path column chromatography, initially using ethyl acetate and then 95:5 ether-methanol as eluents. The title compound was obtained as an oil (0.21 g). I.R. (CHBr$_3$) 1728, 1704 cm$^{-1}$.

Analysis Found: C, 66.3; H, 8.7; N, 4.6; C$_{17}$H$_{25}$NO$_4$ requires: C, 66.4; H, 8.2; N, 4.6%.

EXAMPLE 175

[1α(Z),2β,5α]-(±)-7-[1,1'-Biphenyl)-4-yl]methoxy]-2-(4-morpholinyl)-3-oxo-cyclopentyl]-5-heptenoic acid, methyl ester To the product of Example 76 (1 g) and dicyclohexylcarbodiimide (1.67 g) in dry dimethylsulphoxide (15 ml) was added pyridinium trifluoroacetate (0.6 g). The mixture was stirred for 1 hr., poured into water (100 ml) and extracted with ether (4×75 ml). The combined organic extracts were filtered (to remove dicyclohexyl urea), washed successively with water (100 ml) and brine (100 ml), dried (over MgSO$_4$) and evaporated to afford a semi-solid (2.65 g). The residue was triturated with ether/petroleum ether (1:1) (50 ml), filtered and the filtrate evaporated. The resulting oil was purified by chromatography on silica, eluting with ether/petroleum ether (7:3) to give the title compound as a colourless oil (0.7 g) I.R. (CHBr$_3$) 1735 cm$^{-1}$.

Analysis Found C, 73.8; H, 7.9; N, 3.3 C$_{30}$H$_{37}$NO$_5$ requires C, 73.3; H, 7.6; N, 2.9%.

EXAMPLE 176

[1α(Z),2β,5α]-(±)-7-[5-(4-Cyclohexylphenylmethoxy)-2-(4-morpholinyl)-3-oxocyclopentyl]-5-heptenoic acid, methyl ester To the product of Example 78 (0.8 g) and dicyclohexyl carbodiimide (1.32 g) in dimethyl sulphoxide (10 ml) was added pyridinium trifluoroacetate (474 mg). The mixture was stirred at room temperature for 1 hr then poured into water (50 ml) and extracted with ether (4×50 ml). The combined extracts were filtered (to remove dicyclohexyl urea), washed with water (50 ml) and brine (50 ml), dried (MgSO$_4$) and evaporated. The residual semi-solid was triturated with ether/petroleum ether (1:1) (20 ml), filtered and the filtrate evaporated. The residue was purified by chromatography on silica, eluting with ether/petroleum ether (4:1) gave a title compound (0.62 g) as a straw coloured oil.

I.R. (CHBr$_3$) 1735 cm$^{-1}$

Analysis Found C, 72.3; H, 9.0; N, 3.0 C$_{30}$H$_{43}$NO$_5$ requires C, 72.4; H, 8.7; N, 2.8%.

EXAMPLE 177

[1α(Z),2β,5α]-(±)-7-[5-[4-Dimethylamino(phenylmethoxy)]-2-(4-morpholinyl)-3-oxocyclopentyl]-5-heptenoic acid, methyl ester To the product of Example 81 (0.51 g) and dicyclohexyl carbodiimide (915 mg) in dry dimethyl sulphoxide (10 ml) was added pyridinium trifluoroacetate (546 mg). The mixture was stirred for 1 hr then poured into water (100 ml) and extracted with ether (4×50 ml). The combined extracts were filtered (to remove dicyclohexyl urea), washed with water (2×50 ml), followed by brine (50 ml), dried (MgSO$_4$) and evaporated. The residual semi-solid was triturated with ether: petroleum ether (1:1) (10 ml), filtered and the filtrate evaporated. The product was purified by chromatography on silica, eluting with ether:petroleum ether (4:1) gave a title compound (282 mg) as a colourless oil.

I.R. (CHBr$_3$) 1733 cm$^{-1}$

Analysis Found C, 67.8; H, 8.5; N, 6.1; C$_{26}$H$_{40}$N$_2$O$_5$ requires C, 68.1; H, 8.4; N, 6.1%.

EXAMPLE 178

[1α(Z),2β,5α]-(±)-7-[5-[4-Azido(phenylmethoxy)]-2-(4-morpholinyl)-3-oxocyclopentyl]-5-heptenoic acid, methyl ester To a cold (ca. 10°) solution of the product of Example 82 (2.68 g) and dicyclohexylcarbodiimide (4.70 g) in dimethylsulphoxide (20 ml) was added pyridinium trifluoroacetate (1.65 g). The reaction was stirred for 30 min at room temperature then poured into water (100 ml) and extracted with dichloromethane (3×100 ml). The combined organic layers were filtered, washed with water (200 ml) and brine (200 ml), dried (MgSO$_4$) and the solvent evaporated. The residual oil was treated with ether to remove suspended dicyclohexylurea giving a yellow oil (4.1 g) which was chromatographed on silica. Elution with ether gave the title compound as a yellow oil (1.94 g). I.R. (Neat) 2110, 1740 cm$^{-1}$ Analysis Found C, 63.15; H, 7.1; N, 12.9 C$_{24}$H$_{32}$N$_4$O$_5$ requires C, 63.1; H, 7.0; N, 12.3%.

EXAMPLE 179

[1α(Z),2β,5α]-(±)-7-[5-[4-Amino(phenylmethoxy)]-2-(4-morpholinyl)-3-oxocyclopentyl]-5-heptenoic acid, methyl ester Freshly activated zinc powder (1.4 g) was added to a mixture of the product of Example 178 (1.0 g), tetrahydrofuran (10 ml) and potassium dihydrogen phosphate solution (1 M, 10 ml) at 0°. The reaction mixture was stirred at room temperature for 2 hr., poured into sodium bicarbonate solution (30 ml) and filtered, Extraction of the filtrate with ether (3×30 ml) yielded an oil (936 mg) which was chromatographed on silica (Merck 7729, 30 g). Elution with ether gave the title compound as a yellow oil (450 mg). I.R. (CHBr$_3$) 3450, 3370, 1735 cm$^{-1}$ Analysis Found: C, 66.7; H, 8.1; N, 6.6; $C_{27}H_{34}N_2O_5$ requires C, 67.0; H, 7.9; N, 6.5%.

EXAMPLE 180

[1α(Z),2β,5α]-(±)-7-[2-(4-Morpholinyl)-3-oxo-5-phenoxycyclopentyl]-5-heptenoic acid, methyl ester To the product of Example 84 (0.2 g) and dicyclohexylcarbodiimide (409 mg) in dry dimethylsulphoxide (3 mls) was added pyridinium trifluoroacetate (147 mgs). After 1 hr the mixture was poured into water (30 mls) and extracted with dichloromethane (5×30 mls). The combined extracts were dried (over MgSO$_4$) and evaporated to give a semi-solid (650 mgs). The residue was triturated with ether/petroleum ether (7:3) (10 mls), filtered and the filtrate evaporated. The crude product was subjected to chromatography on silica, eluting with ether/petroleum ether (7:3) gave the title compound (136 mg) as a colourless solid which was purified from the ether petroleum ether m.p. 78°-79°. I.R. (CHBr$_3$) 1740 cm$^{-1}$

EXAMPLE 181

1α(Z),2β,5α]-(±)-7-[3-Oxo-2-(4-methyl-1-piperazinyl)-5-(phenylmethoxy)-cyclopentyl]-5-heptenoic acid, methyl ester, maleate, (1:1)

A solution of the product of Example 3 Table 5 (364 mg) and dicyclohexylcarbodiimide (0.70 g) in dimethylsulphoxide (5 ml) was treated with trifluoroacetic acid (0.163 ml) with water bath cooling. After 2 hr. triethylamine (0.53 ml) was added with vigorous stirring followed by addition of water (10 ml) and extraction into ether (3×15 ml). The combined organic layers were filtered, washed with water and brine, dried (MgSO$_4$) and the solvent evaporated. The residual oil was treated with ether/petroleum ether and filtered to remove the suspended dicyclohexylurea. The filtrate was evaporated to give an oil (414 mg) which was chromatographed on silica eluting with glacial acetic acid/methanol/ether 1:50:50. Following elution of the remaining dicyclohexylurea the eluent polarity was increased to glacial acetic acid/methanol/ether 1:75:25. The fractions containing the acetate salt of the ketone were combined and the solvent evaporated. Sodium bicarbonate solution (15 ml) was added and the ketone extracted into ether (3×15 ml). The combined organic portions were washed with water and brine, dried (MgSO$_4$) and evaporated to give an oil (162 mg). A saturated solution of maleic acid in ether was added to a solution of the oil in ether (3 ml) until precipitation of the maleate salt ceased. The mixture was filtered and the solid (186 mg) was purified from ethyl acetate/ether to give the title compound as a white solid (136 mg) m.p. 102°-3°.

Analysis Found: C, 63.6; H, 7.1; N, 5.2; $C_{25}H_{36}N_2O_4 \cdot C_4H_4O_4$ requires C, 64.0; H, 7.35; N, 5.2%.

EXAMPLE 182

(1α,2β,5α)-(±)-3-Oxo-5-(Phenylmethoxy)-2-(4-thiomorpholinyl) cyclopentane heptanoic acid, methyl ester, S-dioxide A solution of the product of Example 118 (1.8 g) and dicyclohexylcarbodiimide (4 g) in dry dimethylsulphoxide (30 ml) was stirred at room temperature whilst pyridinium trifluoroacetate (1.12 g) was added in one portion. The reaction was stirred at room temperature for 5 days. The reaction mixture was poured into water (300 ml) and ether (100 ml) and stirred for 10 min. The precipitated urea was filtered off and the layers were separated. The aqueous layer was extracted with ether (×3). The combined organic layers were washed with water, dried and evaporated to give an oil which was purified by chromatography on silica. Elution with ether gave a solid (1.4 g) which was purified from ethyl acetate-petrol (40°-60°, 1:1) to give the title compound as white prisms (0.96 g) m.p. 81°-3°.

Analysis Found: C, 62.0; H, 8.0; N, 3.05; $C_{24}H_{35}SNO_6$ requires: C, 61.9; H, 7.6; N, 3.0%.

EXAMPLE 183

[1α,2β,5α]-(±)-2-[N-(2-Chloroacetyloxyethyl)-N-methylamino]-3-oxo-5-(phenylmethoxy)cyclopentane heptanoic acid, methyl ester Pyridinium trifluoroacetate (1.07 g) was added to a mixture of the product of Example 122 (1.78 g) and dicyclohexylcarbodiimide (3.03 g) in dry dimethyl sulphoxide (25 ml). After stirring for 30 min. the mixture was poured into water (150 ml) and extracted into ether (3×100 ml). The combined extracts were dried (MgSO$_4$), filtered and evaporated to afford a viscous oil (2.6 g). Column chromatography on silica gel with 1:3 petroleum ether/ether as eluent gave the title compound (1.12 g) as a yellow oil.

I.R. (CHBr$_3$) 1730 cm$^{-1}$

Analysis Found: C, 61.8; H, 77; N, 3.1. $C_{25}H_{36}ClNO_6$ requires: C, 62.3; H, 7.5; N, 2.9%.

EXAMPLE 184

[1α,2β,5α]-(±)-2-[N-(2-Hydroxyethyl)-N-methylamino]-3-oxo-5-(phenylmethoxy)cyclopentane heptanoic acid, methyl ester Potassium bicarbonate (0.265 g) was added to a solution of the product of Example 183 (0.85 g) in aqueous methanol (10 ml). After stirring for 6 hr. the mixture was poured into a saturated solution of ammonium chloride (75 ml) and extracted into ether (3×50 ml). The combined extracts were dried (MgSO$_4$), filtered and evaporated to afford an oil (0.73 g). Column chromatography on silica gel with 10% methanol in ether as eluent gave the title compound (0.64 g) as a yellow oil. I.R. (CHBr$_3$) 3560,3440(br), 1738 cm$^{-1}$ Analysis Found: C, 68.4; H, 8.9; N, 3.4; $C_{23}H_{35}NO_5$ requires C, 68.1; H, 8.7; N, 3.4%.

EXAMPLES 185-198

7-(2,5-Disubstituted-3-oxocyclopentyl)heptanoic acimethyl esters

Table 13 summarises the preparation of the title compounds by the following method:

To a cold (−60°) solution of acetyl bromide in dry dichloromethane under nitrogen was added dimethylsulphoxide in dichloromethane. After 10 min. a solution of the appropriate alcohol in dichloromethane was added to the activated complex. The mixture was stirred for approximately half the specified time whereupon triethylamine was added. The mixture was allowed to reach ambient temperature when stirring was continued for the remaining time specified. The solution was poured into water, the phases separated, and the aqueous phase extracted with dichloromethane. The remaining work-up is as described in Method A, Table 11.

TABLE 13

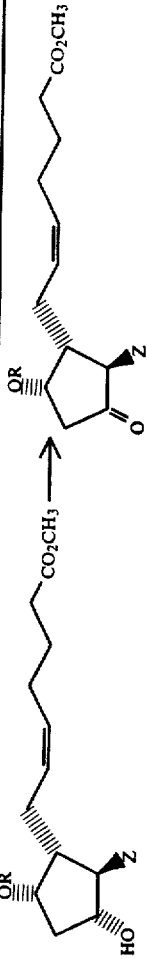

| Ex. No. | Starting Material Z | R | Wt (g) | DMSO Vol. (ml) | CH₃COBr Vol. (ml) | CH₂Cl₂ Total/Vol (ml) | Et₃N Vol. (ml) | Time hr | Chromatography System ether-petroleum ether | Yield (g) | I.R. (CHBr₃) cm⁻¹ | Tlc (Silica) Rf (Solvent)* |
|---|---|---|---|---|---|---|---|---|---|---|---|---|
| 185 | morpholino | —CH₂—C₆H₄—CONH₂ | 0.4 | 0.23 | 0.213 | 10 | 1.2 | 2.5 | 9:1 ether-methanol | 0.19 | 3530/3410, 1740,/1678 | 0.53 |
| 186 | morpholino | —CH₂—C₆H₄—CH₂N(CH₃)₂ | 0.51 | 0.37 | 0.39 | 25 | 1.5 | 1.25 | 1:1 ether-methanol | 0.23 | 1740 | 0.35 |
| 187 | morpholino | —CH₂—C₆H₄—CF₃ | 0.9 | 0.46 | 0.41 | 28 | 3.9 | 1 | 3:2 | 0.64 | 1738 | 0.16 (m.p. 47.5–48.5° from ether-petroleum/ether) |
| 188 | morpholino | —CH₂—C₆H₄—Ph (ortho) | 0.5 | 0.35 | 0.36 | 25 | 1.45 | 1.5 | 4:1 | 0.39 | 1740 | 0.39 |
| 189 | N(CH₃)(CH₂Ph) | —CH₂Ph | 1.5 | 0.6 | 0.6 | 25 | 4.6 | 2.25 | 7:3 | 0.7 | 1730 | 0.32 |
| 190 | morpholino | —(CH₂)₃Ph | 0.68 | 0.41 | 0.34 | 25 | 3.2 | 1.25 | 3:2 | 0.4 | 1737 | 0.24 |
| 191 | morpholino | —CH₂—C₆H₄—O(CH₂)₃CH₃ | 1.0 | 0.7 | 0.72 | 35 | 2.9 | 1.5 | 4:1 | 0.74 | 1738 | 0.32 |

TABLE 13-continued

Starting Material: [cyclopentane with OR, HO, Z substituents and CO₂CH₃ chain] → [cyclopentanone with OR, Z substituents and CO₂CH₃ chain]

| Ex. No. | Z | R | Wt (g) | DMSO Vol. (ml) | CH₃COBr Vol. (ml) | CH₂Cl₂ Total/Vol (ml) | Et₃N Vol. (ml) | Time hr | Chromatography System ether-petroleum ether | Yield (g) | I.R. (CHBr₃) cm⁻¹ | Tlc (Silica) Rf (Solvent)* |
|---|---|---|---|---|---|---|---|---|---|---|---|---|
| 192 | [morpholine] | —CH₂—(3-OPh-phenyl) | 0.9 | 0.6 | 0.63 | 35 | 2.5 | 1.5 | 4:1 | 0.59 | 1738 | 0.35 |
| 193 | [2-CH₃-morpholine] | —CH₂Ph | 1.2 | 0.67 | 0.6 | 41 | 5.6 | 1.5 | 1:3 | 0.53 | 1735 | 0.46 (ether) |
| 194 | [morpholine] | —CH₂—(2-OPh-phenyl) | 0.9 | 0.6 | 0.63 | 35 | 2.5 | 1.5 | 4:1 | 0.46 | 1735 | 0.38 |
| 195 | [2-CH₃-morpholine] | —CH₂—(4-OPh-phenyl) | 0.75 | 0.51 | 0.53 | 35 | 2.1 | 1.5 | 4:1 | 0.63 | 1735 | 0.39 |
| 196 | [2-CH₃-morpholine] | —CH₂Ph | 0.17 | 0.093 | 0.083 | 6 | 0.78 | 1.5 | 1:3 | 0.13 | 1735 | 0.61 (95:5 ether-methanol) |

TABLE 13-continued
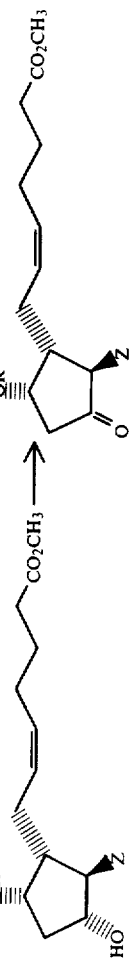
| Ex. No. | Starting Material R | Z | $W_1$ (g) | DMSO Vol. (ml) | $CH_3COBr$ Vol. (ml) | $CH_2Cl_2$ Total/Vol (ml) | $Et_3N$ Vol. (ml) | Time hr | Chromatography System ether-petroleum ether | Yield (g) | I.R. $(CHBr)_3$ $cm^{-1}$ | Tlc (Silica) Rf (Solvent)* |
|---|---|---|---|---|---|---|---|---|---|---|---|---|
| 197 | —CH(Me)₂ | [piperidine] | 0.65 | 0.31 | 0.39 | 68 | 2.5 | 1.5 | 1:4 | 0.37 | 1730 | 0.14 |
| 198 | —CH₂CH₂Ph | [piperidine] | 0.65 | 0.26 | 0.26 | 60 | 2.1 | 1.5 | 3:7 | 0.24 | 1735 | 0.27 |
*Solvent is as described for column chromatography.

EXAMPLE 199

[1α(Z),2β,5α]-(±)-7-[5-[4-(1,1-Dimethylethyl)phenyl-methoxy]2-(4-morpholinyl)-3-oxocyclopentyl]-5-heptenoic acid, methyl ester Dry dimethylsulphoxide (0.92 ml) in dry dichloromethane (10 ml) was added under nitrogen to a cold (−60°) solution of acetyl bromide (0.96 ml) in dry dichloromethane (5 ml). The resultant yellow activated complex was stirred for 10 min. whereupon the product of Example 83 (1.3 g) in dry dichloromethane (10 ml) was slowly introduced. After 40 min. triethylamine (3.8 ml) in dry dichloromethane (10 ml) was added. The solution was stirred at room temperature for a further 45 min. then poured into water (200 ml) and extracted into dichloromethane (3 × 100 ml). The combined extracts were dried (MgSO$_4$), filtered and evaporated to afford an oil (1.6 g). Chromatography on silica with 20% petroleum ether in ether as the eluent gave the title compound as an orange oil (0.575 g). I.R. (CHBr$_3$) 1737 cm$^{-1}$ Analysis Found C, 71.1; H, 9.0; N, 3.0; C$_{28}$H$_{41}$NO$_5$ requires C, 71.3; H, 8.8; N, 3.0%.

EXAMPLE 200

[1α,2β(2±),5α]-(±)-2-[N-(2-Chloroacetyloxyheptyl)N-methylamino]-3-oxo-5-(phenylmethoxy)cyclopentane heptanoic acid, methyl ester Dimethylsulphoxide (0.75 ml) in dry dichloromethane (5 ml) was added dropwise to a cold (−70°) solution of acetyl bromide (0.69 ml) in dry dichloromethane (5 ml) under nitrogen. After 15 min. the product of Example 121 (2.33 g) in dry dichloromethane (5 ml) was added dropwise to the yellow suspension. After 40 min. triethylamine (5.8 ml) in dichloromethane (4 ml) was added and the mixture stirred at room temperature for 1 hr. The suspension was poured into 8% sodium bicarbonate solution (100 ml) and extracted with dichloromethane (3 × 100 ml). The combined organic extracts were washed with brine, dried (MgSO$_4$) and concentrated to afford a dark red oil. The product was purified by chromatography on silica. Elution with petroleum ether in ether 1:1 gave the title compound as a yellow oil (1.47 g). I.R. (CHBr$_3$) 3600, 3500 (br), 1730 cm$^{-1}$ Analysis Found: C, 65.7; H, 8.6; N, 2.6. C$_{30}$H$_{46}$ClNO$_6$ requires: C, 65.3; H, 8.4; N, 2.5%.

EXAMPLE 201

[1α,2β(2±)]-(±)-2-[N-(2-Hydroxyheptyl)-N-methylamino]-3-oxo-cyclopent-4-ene, heptanoic acid, methyl ester Potassium bicarbonate (0.34 g) was added to a cold (0°) solution of the product of Example 200 (0.61 g) in methanol (5 ml) and water (0.5 ml). The mixture was stirred rapidly at room temperature for 38 hr., poured into saturated ammonium chloride solution (50 ml) and extracted into dichloromethane (3 × 100 ml). The combined organic extracts were washed with brine, dried (MgSO$_4$) and concentrated. The product was combined with material from three further reactions (780 mg) and subjected to short path column chromatography on silica gel. Eluting with 3% methanol in dichloromethane gave the title compound (340 mg). The title compound was further purified by column chromatography on silica using 15% petroleum ether (40°–60°) in ether as eluent and obtained as a yellow oil (182 mg). I.R. (Neat) 3440 (br), 1740, 1710 cm$^{-1}$ Analysis Found: C, 68.2; H, 10.4; N, 3.8; C$_{21}$H$_{37}$NO$_4$ requires C, 68.6; H, 10.2; N, 3.8%.

EXAMPLE 202

[1α,2β(2±),5α]-(±)-2-[N-(2-Hydroxyheptyl)-N-methylamino]-3-oxo-5-(phenylmethoxy)cyclopentane heptanoic acid, methyl ester The title compound (110 mg) was obtained from the experiment described in Example 201 by further elution of the short path silica column with 3% methanol in dichloromethane. I.R. (Neat) 3450, 1740 cm$^{-1}$ Analysis Found: C, 70.2; H, 9.8; N, 3.1; C$_{28}$H$_{45}$NO$_5$ requires: C, 70.7; H, 9.5; N, 3.0%.

EXAMPLES 203–207

(1α,2β,5α)-(±)-2,5-Disubstituted-3-oxocyclopentane heptanoic acid, methyl esters Table 14 summarises the preparation of the title compounds by the following method:

A solution of the appropriate alkene in ethyl acetate or methanol was hydrogenated over pre-reduced 10% palladium on charcoal at atmospheric pressure. When the hydrogen uptake ceased after the time specified, the mixture was filtered through hyflo and evaporated. The residue when necessary was chromatographed on silica gel with the solvent specified to give the title compound.

TABLE 14

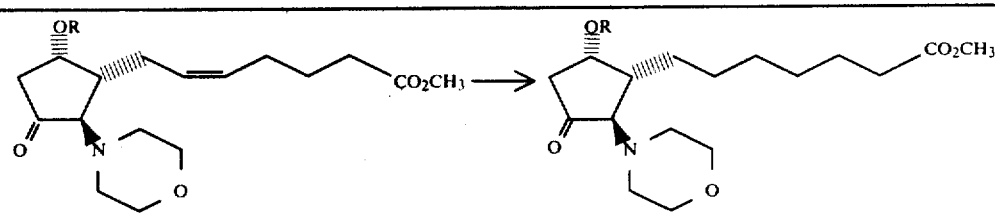

| Ex. No. | Starting Material R | Wt (g) | Product R | PdO Wt. (g) | EtoAc Vol. (ml) | MeoH Vol. (ml) | Time hr | Chromatography System | Yield (g) | I.R. (CHBr$_3$) cm$^{-1}$ | Tlc (Silica) Rf (Ether) |
|---|---|---|---|---|---|---|---|---|---|---|---|
| 203 | —CH$_2$Ph | 0.5 | —CH$_2$Ph | 0.1 | — | 25 | 3 | — | 0.43 | 1735 | 0.6 |
| 204 | —CH(Ph)$_2$ | 0.565 | —CH(Ph)$_2$ | 0.1 | — | 50 | 0.5 | 4:1 Ether-petroleum ether | 0.37 | 1732 | 0.51 |
| 205 | —CH$_2$CH$_2$Ph | 0.82 | —CH$_2$CH$_2$Ph | 0.1 | — | 70 | 0.5 | 3:2 Ether-petroleum | 0.59 | 1735 | 0.5 (m.p. 39–40°) |

TABLE 14-continued

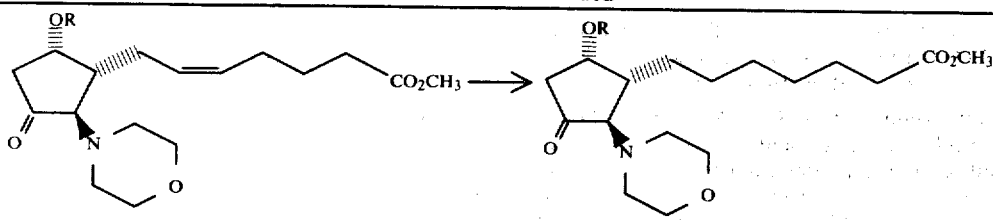

| Ex. No. | Starting Material R | Wt (g) | Product R | PdO Wt. (g) | EtoAc Vol. (ml) | MeoH Vol. (ml) | Time hr | Chromatography System | Yield (g) | I.R. (CHBr₃) cm⁻¹ | Tlc (Silica) Rf (Ether) |
|---|---|---|---|---|---|---|---|---|---|---|---|
| 206 | —CH(Me)₂ | 0.2 | —CH(Me)₂ | 0.05 | 15 | — | 0.5 | ether Ether | 0.195 | 1730 | 0.48 |
| 207 | —CH₂—⟨⟩—N₃ | 0.86 | CH₂—⟨⟩—NH₂ | 0.43 | 15 | 0 | 0.25 | Ether | 0.5 | 3450, 3380, 1738 | 0.2 |

EXAMPLE 208

[1α,2β,5α]-(±)-5-[[(1,1'-Biphenyl)-4-yl]methoxy]-2-(4-morpholinyl)-3-oxocyclopentane heptanoic acid, methyl ester A solution of the product of Example 175 (0.5 g) in ethyl acetate (15 ml) was hydrogenated over pre-reduced 10 palladium oxide on charcoal (200 mg) in ethyl acetate (5 ml). Uptake of hydrogen was complete after 1 hr. (21.5 ml, cf. theoretical 26.9 ml). The mixture was filtered and the ethyl acetate evaporated in vacuo. The resulting solid (500 mg) was chromatographed on silica, eluting with ether to give the title compound as white solid (0.4 g) m.p. 56°-7°.

Analysis Found C, 73.4; H, 8.15; N, 3.0; $C_{30}H_{39}NO_5$ requires C, 73.0; H, 7.9; N, 2.8%.

EXAMPLE 209

(1α,2β,5α)-(±)-[2-(2,6-cis-Dimethyl-4-morpholinyl)-3-oxo-5-(phenyl-methoxy)cyclopentane]heptanoic acid, methyl ester A solution of the product of Example 193 Table 13 (0.55 g) in ethanol (39 ml) was treated according to the method of Examples 203-207, Table 14. Chromatography on silica eluting with ether-petroleum ether 1:4 gave the title compound as an oil (0.17 g).

I.R. (CHBr₃) 1735 cm⁻¹.

Analysis Found: C, 69.7; H, 9.15; N, 3.15; $C_{26}H_{39}NO_5$ requires: C, 70.1; H, 8.8; N, 3.15%.

EXAMPLE 210

[1α(Z),2β,5α]-(±)-7-[5-[4-Formyl(phenylmethoxy]-2-(4-morpholinyl)-3-oxo-cyclopentyl]-5-heptenoic acid, methyl ester The title compound (0.49 g) was prepared from the product of Example 50 (0.7 g) using the procedure described for Examples 148-170 Table 12. Chromatography on silica, eluting with ether, gave an oil. I.R. (Neat) 1740, 1700 cm⁻¹.

Analysis Found: C, 67.5; H, 7.6; N, 3.6. $C_{25}H_{33}NO_6$ requires: C, 67.7; H, 7.5; N, 3.2%.

EXAMPLE 211

[1α(Z),2β,3α,5α]-(±)-7-[5-[2-Azido(phenylmethoxy)]-3-hydroxy-2-(4-morpholinyl)cyclopentyl]-5-heptenoic acid, methyl ester The title compound (4.9 g) was prepared from the product of Preparation 100 (5 g) and -2-oxidobenzyl bromide (14 g) according to Method A1 described for Tables 7-9. Chromatography on silica, eluting with ether-petroleum ether (3:1), then (1:1), gave the product as an oil. I.R. (Neat) 3460, 2140, 1740 cm⁻¹.

T.l.c. (Silica) Rf. 0.47 (4:1 ether-acetone).

EXAMPLE 212

[1α(Z),2β,5α]-(±)-7-[5-[2-Azido(phenylmethoxy]-2-(4-morpholinyl)-3-oxocyclopentyl]-5-heptenoic acid, methy ester The title compound (1.19 g) was prepared from the product of Example 211 (2.4 g) using the procedure described for Examples 185-198. Table 13. Chromatography on silica, eluting with ether-petroleum ether (1:1), gave the product as an orange oil. I.R. (Neat) 2115, 1740 cm⁻¹.

T.l.c. (Silica) Rf. 0.59 (Ether-acetone, 2:1).

EXAMPLE 213

[1α(Z),2β,5α]-(±)-7-[5-[2-Amino(phenylmethoxy)]-2-(4-morpholinyl)-3-oxocyclopentyl]-5-heptenoic acid, methyl ester The title compound (0.66 g) was prepared from the product of Example 212 (1.1 g) using the procedure described for Example 179. Chromatography on silica, eluting with ether-petroleum ether (1:1), gave the product as a yellow oil.

I.R. (Neat) 3455, 3370, 1738 cm⁻¹.

Analysis Found: C, 66.5; H, 8.2; N, 6.7. $C_{24}H_{34}N_2O_5$ requires: C, 67.0; H, 7.9; N, 6.5%.

EXAMPLE 214

[1α(Z),2β,3α,5α]-(±)-7-[5-[4-Amino(phenylmethoxy)]-3-hydroxy-2-(4-morpholinyl)cyclopentyl]-5-heptenoic acid, methyl ester The title compound (3.95 g) was prepared from the product of Example 82 (4.4 g) using the procedure described for Example 179.

I.R. (Neat) 3450, 3360, 1738 cm⁻¹.

T.l.c. (Silica) Rf. 0.45 (9:1, ether-methanol)

EXAMPLE 215

[1α(Z),2β,3α,5α]-(±)-7-[3-Hydroxy-2-(4-morpholinyl)-5-[4-pyrrolidinyl (phenylmethoxy)]cyclopentyl]-5-heptenoic acid, methyl ester A mixture of the product of Example 214 (1.5 g), 1,4-dibromobutane (0.99 g) and potassium carbonate (0.72 g) in acetonitrile (20 ml) was heated at 85° when stirring for 24 hr. 8% Sodium bicarbonate solution (100 ml) was added and the mixture was extracted with ether. The combined extracts were worked up with brine, dried (MgSO$_4$) and evaporated to give an oil (1.86 g). Chromatography on silica, eluting with ether-methanol (95:5), gave the title compound as a straw coloured oil (1.2 g). I.R. (Neat) 3450, 1740 cm$^{-1}$.

Analysis Found: C, 69.1; H, 9.15; N, 5.6. $C_{28}H_{42}N_2O_5$ requires: C, 69.1; H, 8.7; N, 5.8%.

EXAMPLE 216

[1α(Z),2β,5α]-(±)-7-[2-(4-Morpholinyl)-3-oxo-5-[4-pyrrolidinyl (phenylmethoxy)]cyclopentyl]-5-heptenoic acid, methyl ester The title compound (0.3 g) was prepared from the product of Example 215 (0.55 g) using the procedure described for Examples 148-170, Table 12. Chromatography on silica, eluting with ether-petroleum ether (2:1), afforded the product as an oil. I.R. (Neat) 1740 cm$^{-1}$.

Analysis Found: C, 69.05; H, 8.5; N, 5.7. $C_{28}H_{40}N_2O_5$ requires: C, 69.4; H, 8.3; N, 5.8%.

EXAMPLE 217

[1α(Z),2β,3α,5α]-(±)-7-[3-Hydroxy-2-(4-Morpholinyl)-5-[4-dipropylamino(phenylmethoxy)cyclopentyl]-5-heptenoic acid, methyl ester A mixture of the product of Example 214, (0.5 g), propanol (0.67 g) and sodium cyanoborohydride (0.22 g) in acetonitrile (4 ml) and water (1.8 ml) was cooled at 0° with stirring whilst glacial acetic acid (0.15 ml) was added over ca. 2 minutes. The reaction mixture was allowed to warm to room temperature and stirred for a further 2 hr. The reaction mixture was diluted with ether and washed with 1 N sodium hydroxide solution and brine. The organic layer was dried and evaporated to give an oil which was chromatographed on silica. Eluting with ether-methanol (98:2) gave the title compound as a straw coloured oil (0.29 g).

I.R. (Neat) 3450, 1740 cm$^{-1}$.

Analysis Found: C, 69.8; H, 9.8; N, 5.45. $C_{30}H_{48}N_2O_5$ requires: C, 69.7; H, 9.4; N, 5.4%.

EXAMPLE 218

[1α(Z),2β,5α]-(±)-7-[2-(4-Morpholinyl)-3-oxo-5-[dipropylamino (phenylmethoxy)]cyclopentyl]-5-heptenoic acid, methyl ester The title compound (0.34 g) was prepared from the product of Example 217 (0.52 g) using the procedure described for Examples 148-170 (Table 12). Chromatography on silica, eluting with ether-petroleum ether (2:1), gave a colourless oil.

I.R. (Neat) 1740 cm$^{-1}$.

Analysis Found: C, 69.6; H, 9.0; N, 5.5. $C_{30}H_{46}N_2O_5$ requires: C, 70.0; H, 9.0; N, 5.4%.

EXAMPLE 219

(1α,2β,5α)-(±)-5-[[(1,1'-Biphenyl)-4-yl]methyloxy]-3-oxo-2-(1-piperidinyl)cyclopentane heptanoic acid, methyl ester The title compound (0.04 g) was prepared from the product of Example 137 (0.18 g) using the procedure described for Examples 203-207 (Table 14). Chromatography on silica, eluting with ether, gave the product as a colourless oil.

I.R. (Neat) 1740 cm$^{-1}$.

Analysis Found: C, 75.5; H, 8.8 N, 2.8. $C_{31}H_{41}NO_4$ requires: C, 75.7; H, 8.4; N, 2.85%.

EXAMPLE 220

[1α(Z),2β,3α,5α]-(±)-7-[5-[4-Azido(phenylmethoxy)]-2-(1-piperidinyl)-3-[(tetrahydro-2H-pyran-2-yl)oxy]cyclopentyl]5-heptenoic acid, methyl ester.

The title compound (2.55 g) was prepared from the product of Preparation 98 (3.3 g) and 4-azidobenzyl bromide (10.4 g) according to Method B described for Tables 7-9. Chromatography on silica, eluting with ether, gave a dark orange oil I.R. (Neat) 2100, 1740 cm$^{-1}$.

T.l.c. (Silica) Rf 0.5 (ether)

EXAMPLE 221

[1α(Z),2β,3α,5α]-(±)-7-[5-[4-Azido(phenylmethoxy)]-3-hydroxy-2-(1-piperidinyl)cyclopentyl]-5-heptenoic acid, methyl ester.

The title compound (1.2 g) was prepared from the product of Example 220 (2.0 g) according to Method C2 described for Tables 7-9. Chromatography on silica, eluting with ethermethanol (95:5), gave a yellow oil. I.R. (Neat) 3440, 2110, 1738 cm$^{-1}$.

Analysis Found: C, 65.5; H, 7.6; N, 12.0. $C_{25}H_{36}N_4O_4$ requires: C, 65.8; H, 8.0; N, 12.3%.

EXAMPLE 222

[1α(Z),2β,5α]-(±)-7-[5-[4-Azido(phenylmethoxy)]-3-oxo-2-(1-piperidinyl)cyclopentyl]-5-heptenoic acid, methyl ester The title compound (0.79 g) was prepared from the product of Example 221 (1.21 g) using the procedure described for Examples 148-170 (Table 12). Chromatography on silica, eluting with ether-petroleum ether (1:2), gave an oil.

I.R. (Neat) 2120, 1740 cm$^{-1}$.

T.l.c. (Silican) Rf. 0.8 (Ether-methanol, 95:5).

EXAMPLE 223

[1α(Z),2β,5α]-(±)-7-[5-[4-Amino(phenylmethoxy)]-3-oxo-2-(1-piperidinyl)cyclopentyl]-5-heptenoic acid, methyl ester.

The title compound (0.25 g) was prepared from the product of Example 222 (0.39 g) using the procedure described for Example 179. Chromatography on silica, eluting with ether, gave the product as an oil. I.R. (Neat) 2460, 2375, 1740 cm$^{-1}$.

T.l.c. (Silica) Rf. 0.4 (Ether).

EXAMPLE 224

[1α(Z),2β,3α,5α]-(±)-7-[3-Hydroxy-2-(4-morpholinyl)-5-(1-(naphthalenylmethoxy)cyclopentyl]-5-heptenoic acid, methyl ester The title compound (1.6 g) was prepared from the product of Preparation 100 (2.06 g), 1-chloromethylnaphthalene (5.3 g) and sodium bromide (3.1 g) according to Method A1 described for Tables 7-9. Chromatography on silica, eluting with ether-methanol (97:3), gave the product as an oil.

I.R. (Neat) 3450 (br), 1740 cm$^{-1}$.
T.l.c. (Silica) Rf. 0.26 (Ether-methanol, 97:3)

EXAMPLE 225

[1α(Z),2β,5α]-(±)-7-[2-(4-Morpholinyl)-5α(1-naphthalenylmethoxy)-3-oxocyclopentyl]-5-heptenoic acid, methyl ester.

The title compound (0.5 g) was prepared from the product of Example 224 (0.7 g) using the procedure described for Examples 148-170 Table 12. Chromatography on silica, eluting with ether-petroleum ether (4:1), gave an oil.

I.R. (Neat) 1740 cm$^{-1}$.
T.l.c. (Silica) Rf. 0.4 (ether-petroleum ether, 4:1).

EXAMPLE 226

[1α(Z),2β,5α]-(±)-7-[2-[N-methyl-N-(phenylmethyl)amino]-5-(phenylmethoxy)-3-cyclopenten-1-yl]-5-heptenoic acid, methyl ester The title compound (0.52 g) was prepared from the product of Example 32 (0.8 g) according to Method B described for Tables 7-9. Chromatography on silica, eluting with ether-petroleum ether (1:3) ether (2:3), gave an oil. I.R. (Neat) 1740 cm$^{-1}$.
T.l.c. (Silica) Rf. 0.55 (Ether-petroleum, ether, 3:2).

EXAMPLE 227

[1α(Z),2β,3α,5α]-(±)-7-[3-Hydroxy-2-[N-methyl-N-[2-(phenylmethoxy)ethyl]amino]-5-(phenylmethoxy)cyclopentyl-5]heptenoic acid, methyl ester The title compound (0.55 g) was prepared from the product of Preparation 116 (1.44 g) according to Method C2 described for Tables 7-9. Chromatography on silica, eluting with ether-petroleum ether (1:1) then ether, gave the product as an oil.

I.R. (CHBr$_3$) 3540, 1730 cm$^{-1}$.
Analysis Found: C, 72.6; H, 8.55; N, 2.85. C$_{30}$H$_{41}$NO$_5$ requires: C, 72.75; H, 8.3; N, 2.85%.

EXAMPLE 228

[1α(Z),2β,3α,5α]-(±)-7-[3-Hydroxy-2-[N-methyl-N-(4-phenoxybutyl)amino]-5-(phenylmethoxy)cyclopentyl]-5-heptenoic acid, methyl ester The title compound (0.48 g) was prepared from the product of Preparation 117 (1.37 g) according to Method C2 described for Tables 7-9. Chromatography on silica, eluting with ether-petroleum ether (1:1), then (2:1), gave the product as an amber oil.

I.R. (CHBr$_3$) 3540, 1730 cm$^{-1}$.
T.l.c. (Silica) Rf. 0.57 (ether-methanol, 9:1)

EXAMPLE 229

[1α(Z),2β,3α,5α]-(±)-7-[3-Hydroxy-2-[N-methyl-N-(5-phenylpentyl)amino]-5-(phenylmethoxy)cyclopentyl]-5-heptenoic acid, methyl ester The title compound (0.7 g) was prepared from the product of Preparation 118 (15 g) according to Method C2 described for Tables 7-9. Chromatography on silica, eluting with benzene-ethyl acetate (3:1), then (1:1), gave the product as a pale-yellow oil.

I.R. (CMBr$_3$) 3540, 1730 cm$^{-1}$.
Analysis Found: C, 75.5; H, 9.0; N, 2.8. C$_{32}$H$_{45}$NO$_4$ requires: C, 75.7; H, 8.9; N, 2.8%.

EXAMPLE 230

[1α(Z),2β,5α]-(±)-7-[2-N-Methyl-N-[2-(phenylmethoxy)ethyl]amino]-3-oxo-5-(phenylmethoxy)cyclopentyl]-5-heptenoic acid, methyl ester.

The title compound (0.06 g) was prepared from the product of Example 227 (0.43 g) using the procedure described for Examples 185-198 (Table 13). Repeated chromatography on silica, eluting with benzene-ethyl acetate (20:1), gave the product as a pale yellow oil.

Analysis Found: C, 72.8; H, 8.2; N, 2.9. C$_{30}$H$_{34}$NO$_5$ requires: C, 73.0; H, 7.9; N, 2.8%.

EXAMPLE 231

[1α(Z),2β,5α]-(±)-7-[2-[N-Methyl-N-(4-phenoxybutyl)amino]3-oxo-5-(phenylmethoxy)cyclopentyl]-5-heptenoic acid, methyl ester The title compound (0.046 g) was prepared from the product of Example 228 (0.31 g) using the procedure described for Examples 185-198 (Table 13). Repeated chromatography on silica, eluting with benzene-ethyl acetate (20:1), gave the product as a colourless oil.

I.R. (Neat) 1740 cm$^{-1}$.
Analysis Found: C, 72.4; H, 8.1; N, 2.7. C$_3$H$_{41}$NO$_5$ requires: C, 73.35; H, 8.1; N, 2.75%.

EXAMPLE 232

[1α(Z),2β,5α]-(±)-7-[2-[N-Methyl-N-(5-phenylpentyl)amino]3-oxo-5-(phenylmethoxy)cyclopentyl]-5-heptenoic acid, methyl ester The title compound (0.15 g) was prepared from the product of Preparation 229 (0.59 g) using the procedure described for Examples 148-170 (Table 12). Chromatography on silica, eluting with benzene-ethyl acetate (25.1), gave an oil.

I.R. (Neat) 1740 cm$^{-1}$.
T.l.c. (Silica) Rf. 0.3 (benzene-ethyl acetate, 5:1).

EXAMPLE 233

[1α(Z),2β,5α]-(±)-7-[2-[N-(2-Hydroxyheptyl)-N-methylamino]5-(phenylmethoxy)-3-cyclopenten-1-yl]-5-heptenoic acid, methyl ester The title compound (0.1 g) was prepared from the product of Preparation 121 (1.4 g) according to Method A1 described for Tables 7-9. Chromatography on silica, eluting with ether-petroleum ether (3:2), gave the product as an oil.

I.R. (Neat) 3450, 1740 cm$^{-1}$.
T.l.c. (Silica) Rf. 0.19 (Ether-petroleum ether, 3:2).

PHARMACEUTICAL EXAMPLES

Tablets

These may be prepared by direct compression or wet granulation. The direct compression method is preferred but may not be suitable in all cases as it is dependent upon the dose level and physical characteristics of the active ingredient.

| A. Direct Compression | mg/tablet |
|---|---|
| Active ingredient | 100.00 |
| Microcrystalline Cellulose B.P.C. | 298.00 |
| Magnesium Stearate | 2.00 |
| Compression Weight | 400.00 |

The active ingredient is sieved through a 250 μm sieve, blended with the excipients and compressed using 10.0 mm punches. Tablets of other strengths may be prepared by altering the compression weight and using punches to suit.

| B. Wet Granulation | mg/tablet |
|---|---|
| Active ingredient | 100.00 |
| Lactose B.P. | 238.00 |
| Starch B.P. | 40.00 |
| Pregelatinised Maize Starch B.P. | 20.00 |
| Magnesium Stearate B.P. | 2.00 |
| Compression Weight | 400.00 |

The active ingredient is sieved through a 250 μm sieve and blended with the lactose, starch and pregelatinised starch. The mixed powders are moistened with purified water, granules are made, dried, screened and blended with the Magnesium Stearate. The lubricated granules are compressed into tablets as described for the direct compression formulae.

The tablets may be film coated with suitable film forming materials, e.g. methyl cellulose or hydroxypropyl methyl cellulose using standard techniques. Alternatively the tablets may be sugar coated.

| Capsules | mg/capsule |
|---|---|
| Active ingredient | 100.00 |
| *STA-RX 1500 | 99.00 |
| Magnesium Stearate B.P. | 1.00 |
| Fill Weight | 200.00 mg |

The active ingredient is sieved through a 250 μm sieve and blended with the other materials. The mix is filled into No. 2 hard gelatin capsules using a suitable filling machine. Other doses may be prepared by altering the fill weight and if necessary changing the capsule size to suit.

| Syrup | mg/5 ml dose |
|---|---|
| Active ingredient | 100.00 |
| Sucrose B.P. | 2750.00 |
| Glycerine B.P. | 500.00 |
| Buffer | |
| Flavour | as required |
| Colour | |
| Preservative | |
| Distilled Water | 5.00 ml |

The active ingredient, buffer, flavour, colour and preservative are dissolved in some of the water, and the glycerine is added. The remainder of the water is heated to 80° C. and the sucrose is dissolved in this and cooled. The two solutions are combined, adjusted to volume and mixed. The syrup produced is clarified by filtration.

| Injection for Intravenous Administration | % w/v |
|---|---|
| Active ingredient | 0.50 |
| Water for injections B.P. to | 100.00 |

Sodium chloride may be added to adjust the toxicity of the solution and the pH may be adjusted to that of maximum stability and/or to facilitate solution of the active ingredient using either dilute acid or alkali.

The solution is prepared, clarified and filled into appropriate sized ampoules sealed by fusion of the glass. The injection is sterilised by heating in an autoclave using one of the acceptable cycles. Alternatively the solution may be sterilised by filtration and filled into sterile ampoules under aseptic conditions. The solution may be packed under an inert atmosphere of nitrogen.

| Inhalation Cartridges | /cartridge |
|---|---|
| Active ingredient (micronised) | 3 mg |
| Lactose B.P. to | 25 mg |

The active ingredient is micronised so that the majority of the particles are between 1 μm and 5 μm in longest dimension and none are greater than 10 μm. The active ingredient is then blended with the lactose and the mix is filled into No. 3 hard gelatin capsules using a suitable filling machine.

We claim:

1. Prostanoids of the general formula (1)

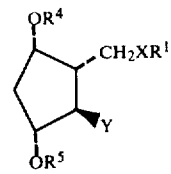

X is cis or trans —CH=CH— or $(CH_2)_2$—;

$R^1$ is straight or branched $C_{1-7}$ alkyl bearing as a terminal substituent —$COOR^{10}$ where $R^{10}$ is a hydrogen atom, $C_{1-6}$ alkyl or $C_{7-10}$ phenalkyl;

Y represents (i) —$NR^2R^3$ where $R^2$ and $R^3$ are the same or different and are each a hydrogen atom, phenalkyl having $C_{1-7}$ alkyl portion or $C_{1-10}$ alkyl, both alkyls being optionally substituted by one or more substituents —$OR^7$ (where $R^7$ is a hydrogen atom, $C_{1-7}$ alkyl, phenyl or phenyalkyl having a $C_{1-4}$ alkyl portion) or —$NR^8R^9$ (where $R^8$ and $R^9$ are the same or different and are each a hydrogen atom or $C_{1-4}$ alkyl, or where —$NR^8R^9$ is a saturated heterocyclic amino group as defined below for Y); any phenyl group in $R^2$ or $R^3$ being optionally substituted by one or more $C_{1-4}$ alkyl or trifluoromethyl groups; always provided that the total numbers of carbon atoms in the group —$NR^2R^3$ does not exceed 15;

or (ii) a saturated heterocyclic amino group selected from the group consisting of pyrrolidino, piperdino, morpholino, piperazino, thiamorpholino, 1-dioxothiamorpholino, homomorpholino, hexamethyleneimino, piperazino substituted at the second nitrogen atom by $C_{1-7}$ alkyl or phenalkyl having a $C_{1-4}$ alkyl portion, and piperidino which contains in the ring the group $C(OH)R^6$ (where $R^6$ is a hydrogen atom, $C_{1-7}$ alkyl, phenyl, or phenalkyl having a $C_{1-4}$ alkyl portion) and any of said groups substituted on the ring by one or more $C_{1-4}$ alkyl groups;

$R^4$ is a hydrogen atom, $C_{1-6}$ alkyl (optionally interrupted by one or two oxygen atoms), $C_{3-6}$ alkenyl, $C_{2-4}$ alkanoyl, phenalkanoyl having a $C_{2-4}$ alkanoyl portion, phenyl or aralkyl selected from the group consisting of benzyhydryl, naphthyl ($C_{1-3}$) alkyl and phen($C_{1-3}$) alkyl and any one of said aryl groups substituted by one or more halogen, hydroxy, $C_{1-6}$ alkyl $C_{1-6}$ alkoxy, $C_{1-4}$ hydroxyalkoxy, trifluoromethyl, cyano, phenyl, phenoxy, $C_{5-7}$ cycloalkyl, phenalkoxy dimethylaminomethyl, carboxamido (—CONH$_2$), thiocarboxamido (—CSNH$_2$), $C_{1-4}$ alkanoyl or —NR$^8$R$^9$ groups as defined above);

$R^5$ is as defined above for $R^4$, excluding phenyl;

and the physiologically acceptable salts thereof; provided that when both $R^4$ and $R^5$ are hydrogen atoms and Y is the group —NR$^2$R$^3$ in which $R^2$ is a hydrogen atom or $C_{1-4}$ alkyl, $R^3$ is not an alkyl group which is only substituted by a hydroxy group.

2. Compounds as claimed in claim 1, wherein $R^1$ is —(CH$_2$)$_3$ COOR$^{10}$ where $R^{10}$ is a hydrogen atom or a $C_{1-3}$ alkyl group.

3. Compounds as claimed in claim 1, wherein Y is pyrrolindino, piperidino, piperidino substituted by hydroxy, morpholino, thiamorpholino, 1-dioxothiamorpholino, piperazino, homomorpholino or hexamethyleneimino, or any of said groups substituted by one or more $C_{1-4}$ alkyl groups.

4. Compounds as claimed in claim 1, wherein Y is a morpholino group or such a group substituted by one or more methyl groups.

5. Compounds as claimed in claim 1, wherein $R^4$ is $C_{1-6}$ alkyl, $C_{1-6}$ alkyl interrupted by one or two oxygen atoms, benzyl or phenethyl, said benzyl and phenethyl groups being optionally substituted by one or more halogen atoms or $C_{1-6}$ alkyl, $C_{1-6}$ alkoxy, trifluoromethyl, cyano, phenyl, $C_{5-7}$ cycloalkyl, amino, dialkylamino, carboxamido, thiocarboxamido, dimethylaminomethyl or formyl groups.

6. Compounds as claimed in claim 1, wherein $R^4$ is other than aralkyl substituted by dimethylaminomethyl, carboxamido, thiocarboxamido or $C_{1-4}$ alkanoyl.

7. A pharmaceutical composition comprising bronchodilating or blood platelet aggregation-inhibiting effective amount of a compound as claimed in claim 1 and one or more pharmaceutical carriers.

* * * * *